United States Patent
Miyake et al.

(10) Patent No.: US 11,716,901 B2
(45) Date of Patent: *Aug. 1, 2023

(54) ORGANIC ELECTROLUMINESCENCE DEVICE AND AMINE COMPOUND FOR ORGANIC ELECTROLUMINESCENCE DEVICE

(71) Applicant: SAMSUNG DISPLAY CO., LTD., Yongin-si (KR)

(72) Inventors: Hideo Miyake, Yokohama (JP); Hiroaki Itoi, Yokohama (JP); Takuya Uno, Yokohama (JP); Masatsugu Ueno, Yokohama (JP); Xiulan Jin, Yokohama (JP); Ichinori Takada, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 303 days.

This patent is subject to a terminal disclaimer.

(21) Appl. No.: 17/095,703

(22) Filed: Nov. 11, 2020

(65) Prior Publication Data

US 2021/0066597 A1    Mar. 4, 2021

Related U.S. Application Data

(63) Continuation of application No. 15/928,609, filed on Mar. 22, 2018, now Pat. No. 10,879,471.

(30) Foreign Application Priority Data

May 10, 2017  (KR) .......... 10-2017-0058268
Dec. 22, 2017 (KR) .......... 10-2017-0178637

(51) Int. Cl.
*C09K 11/06* (2006.01)
*H10K 85/60* (2023.01)
(Continued)

(52) U.S. Cl.
CPC ......... *H10K 85/633* (2023.02); *C07B 59/001* (2013.01); *C07C 211/54* (2013.01);
(Continued)

(58) Field of Classification Search
None
See application file for complete search history.

(56) References Cited

U.S. PATENT DOCUMENTS 8,182,933 B2   5/2012  Osaka et al.
10,079,348 B2  9/2018  Jin et al.
(Continued)

FOREIGN PATENT DOCUMENTS

CN   105601613 A   5/2016
CN   107739607 A   2/2018
(Continued)

OTHER PUBLICATIONS

Liu, et al. "Charge-Transfer Emission in Nonplanar Three Coordinate Organoboron Compounds for Fluorescent Sensing of Fluoride", Angew Chem Int. Ed 2006, 45, p. 5475-5478.
(Continued)

*Primary Examiner* — Robert S Loewe
(74) *Attorney, Agent, or Firm* — Lewis Roca Rothgerber Christie LLP

(57) ABSTRACT

An organic electroluminescence device comprising an amine compound is represented by Formula 1 as a hole transport material.

(Continued)

[Formula 1]

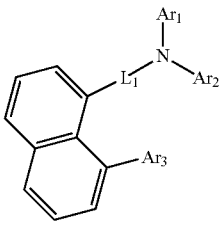

where $Ar_1$, $Ar_2$, $Ar_3$, and $L_1$ are as defined in the specification.

14 Claims, 2 Drawing Sheets

(51) Int. Cl.
C07D 333/76 (2006.01)
C07C 211/54 (2006.01)
C07F 7/08 (2006.01)
C07D 307/91 (2006.01)
C07C 211/58 (2006.01)
C07B 59/00 (2006.01)
C07D 409/12 (2006.01)
C07C 211/61 (2006.01)
H10K 85/40 (2023.01)
H10K 50/15 (2023.01)

(52) U.S. Cl.
CPC .......... *C07C 211/58* (2013.01); *C07C 211/61* (2013.01); *C07D 307/91* (2013.01); *C07D 333/76* (2013.01); *C07D 409/12* (2013.01); *C07F 7/081* (2013.01); *C09K 11/06* (2013.01); *H10K 85/40* (2023.02); *H10K 85/636* (2023.02); *C07C 2603/18* (2017.05); *C09K 2211/1014* (2013.01); *C09K 2211/1022* (2013.01); *H10K 50/15* (2023.02); *H10K 50/156* (2023.02); *H10K 85/626* (2023.02); *H10K 85/6572* (2023.02); *H10K 85/6574* (2023.02); *H10K 85/6576* (2023.02)

(56) References Cited

U.S. PATENT DOCUMENTS

| 10,454,041 | B2 | 10/2019 | Mujia-Fernaud et al. |
| 10,505,122 | B2 | 12/2019 | Lee et al. |
| 10,923,663 | B2 | 2/2021 | Takada et al. |
| 2016/0111650 | A1 | 4/2016 | Noh et al. |
| 2016/0141514 | A1 | 5/2016 | Lee et al. |
| 2016/0248023 | A1 | 8/2016 | Parham et al. |
| 2018/0114907 | A1 | 4/2018 | Takada et al. |

FOREIGN PATENT DOCUMENTS

| EP | 3 010 064 A1 | 4/2016 | |
| EP | 3 312 166 A1 | 4/2018 | |
| JP | 2003-197375 A | 7/2003 | |
| JP | 2009-029726 A | 2/2009 | |
| JP | 2009-267255 A | 11/2009 | |
| JP | 2012167058 A * | 2/2011 | ............. C07C 15/38 |
| JP | 4951829 B2 | 6/2012 | |
| JP | 2014-139156 A | 7/2014 | |
| JP | 5783749 B2 | 9/2015 | |
| JP | 5963467 B2 | 8/2016 | |
| JP | 2016-529211 A | 9/2016 | |
| JP | 2017-22194 A | 1/2017 | |
| JP | 2017-22196 A | 1/2017 | |
| JP | 6081210 B2 | 2/2017 | |
| JP | 2018-65806 A | 4/2018 | |
| KR | 10-2015-0006374 A | 1/2015 | |
| KR | 10-2016-0045567 A | 4/2016 | |
| KR | 10-2018-0112896 A | 10/2018 | |
| KR | 10-2018-0116342 A | 10/2018 | |
| WO | WO 2014/208829 A1 | 12/2014 | |

OTHER PUBLICATIONS

Li, et al., "Double-coupling of dibromo arenes with aryltriol borates for synthesis of diaryl-substituted planar frameworks", Tetrahedron 67, 2011, p. 6804-6811.

Examination report dated Jul. 27, 2018 from the European Patent Office in respect of the European Patent Application 18170465.1.

Bai, et al., Charge-Transfer Emission Involving Three-Coordinate Organoboron: V-Shape versus U-Shape andImpa ct of the Spacer on Dual Emission and Fluorescent Sensing, Chem. Eur. J., 2007, 13, 5713-5723.

Schmidt, et al. Charge Transfer Pathways in Three Isomers of Naphthalene-Bridged Organic Mixed Valence Compounds, J. Org. Chem., 81(2), 595-602, 2016.

Machine translation of KR-2015006374, 37 pages, translation generated Mar. 2020. (Year: 2020).

* cited by examiner

ORGANIC ELECTROLUMINESCENCE DEVICE AND AMINE COMPOUND FOR ORGANIC ELECTROLUMINESCENCE DEVICE

CROSS-REFERENCE TO RELATED APPLICATIONS

This application is a continuation of U.S. patent application Ser. No. 15/928,609, filed on Mar. 22, 2018, which claims priority to and the benefit of Korean Patent Application Nos. 10-2017-0058268, filed on May 10, 2017, entitled: "Amine Compound and Organic Electroluminescence Device Including the Same," and 10-2017-0178637, filed on Dec. 22, 2017, in the Korean Intellectual Property Office, entitled: "Organic Electroluminescence Device and Amine Compound For Organic Electroluminescence Device," the contents of all of which are incorporated herein by reference in their entireties.

BACKGROUND

1. Field

Embodiments relate to an organic electroluminescence device and an amine compound for an organic electroluminescence device.

2. Description of the Related Art

Development on an organic electroluminescence display as an image display is being actively conducted. An organic electroluminescence display differs from a liquid crystal display and is so called a self-luminescent display that accomplishes display by recombining holes and electrons injected from a first electrode and a second electrode in an emission layer and emitting light from a luminescent material which is an organic compound included in the emission layer.

A general organic electroluminescence device may be composed of a first electrode, a hole transport layer disposed on the first electrode, an emission layer disposed on the hole transport layer, an electron transport layer disposed on the emission layer, and a second electrode disposed on the electron transport layer. Holes are injected from the first electrode, and the injected holes move via the hole transport layer and injected into the emission layer. Electrons are injected from the second electrode, and the injected electrons move via the electron transport layer and injected into the emission layer. By recombining the injected holes and electrons into the emission layer, excitons are generated in the emission layer. The organic electroluminescence device emits light using light emitted during the transition of the excitons back to a ground state. In addition, the configuration of an organic electroluminescence device is not limited thereto, and various modifications may be possible. For applying an organic electroluminescence device in a display, the decrease of a driving voltage and the increase of life of the organic electroluminescence device are required.

SUMMARY

Embodiments are directed to an amine compound represented by the following Formula 1:

[Formula 1]

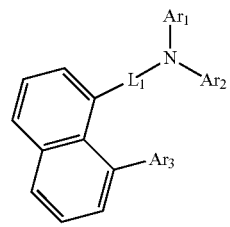

where $Ar_1$ and $Ar_2$ are each independently a substituted or unsubstituted aryl group having 6 to 30 ring carbon atoms, or a substituted or unsubstituted heteroaryl group having 2 to 30 ring carbon atoms, $Ar_3$ is a substituted or unsubstituted aryl group having 6 to 20 ring carbon atoms, and $L_1$ is a substituted or unsubstituted arylene group having 6 to 30 ring carbon atoms, or a substituted or unsubstituted heteroarylene group having 2 to 30 ring carbon atoms.

$Ar_3$ may be a substituted or unsubstituted phenyl group, a substituted or unsubstituted naphthyl group, or a substituted or unsubstituted phenanthryl group.

$L_1$ may be a substituted or unsubstituted phenylene group, a substituted or unsubstituted divalent biphenyl group, a substituted or unsubstituted dibenzofuranylene group, or substituted or unsubstituted dibenzothiophenylene group.

$L_1$ may be represented by the following Formula 2-1 or 2-2:

[Formula 2-1]

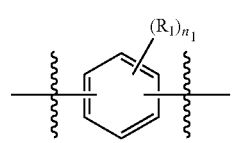

[Formula 2-2]

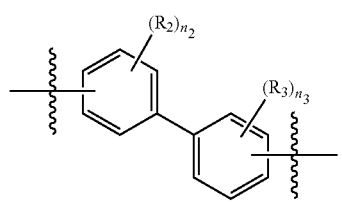

where $R_1$ to $R_3$ are each independently a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, and $n_1$ to $n_3$ are each independently an integer of 0 to 4.

$L_1$ may be represented by the following Formula 2-3 or 2-4:

[Formula 2-3]

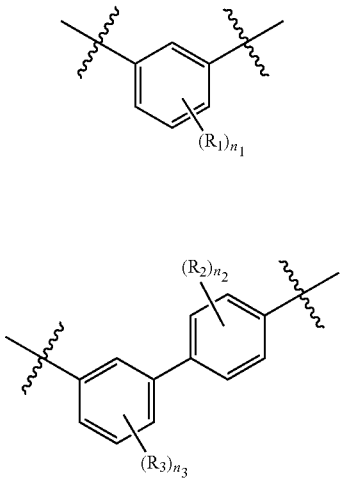

[Formula 2-4]

where $R_1$ to $R_3$, and $n_1$ to $n_3$ are as further defined.

$L_1$ may be represented by the following Formula 2-5 or 2-6:

[Formula 2-5]

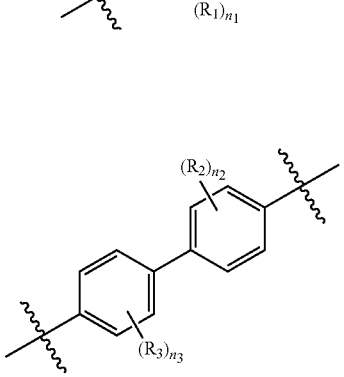

[Formula 2-6]

where $R_1$ to $R_3$, and $n_1$ to $n_3$ are the same further defined.

$Ar_1$ and $Ar_2$ may each independently be a substituted or unsubstituted phenyl group, a substituted or unsubstituted naphthyl group, a substituted or unsubstituted biphenyl group, a substituted or unsubstituted terphenyl group, a substituted or unsubstituted phenanthryl group, a substituted or unsubstituted fluorenyl group, a substituted or unsubstituted dibenzofuranyl group, or a substituted or unsubstituted dibenzothiophenyl group.

When $Ar_3$ is substituted, a substituent may be at least one of deuterium, a silyl group, an alkyl group, or an aryl group.

At least one of $Ar_1$ or $Ar_2$ may be the heteroaryl group, or at least one of $Ar_1$ or $Ar_2$ may include a polycyclic ring.

At least one of $Ar_1$ or $Ar_2$ may be a substituted or unsubstituted naphthylphenyl group, a substituted or unsubstituted phenanthryl group, a substituted or unsubstituted fluorenyl group, a substituted or unsubstituted dibenzofuranyl group, or a substituted or unsubstituted dibenzothiophenyl group.

Formula 1 may be represented by one of the following Formula 1-1 to Formula 1-4:

[Formula 1-1]

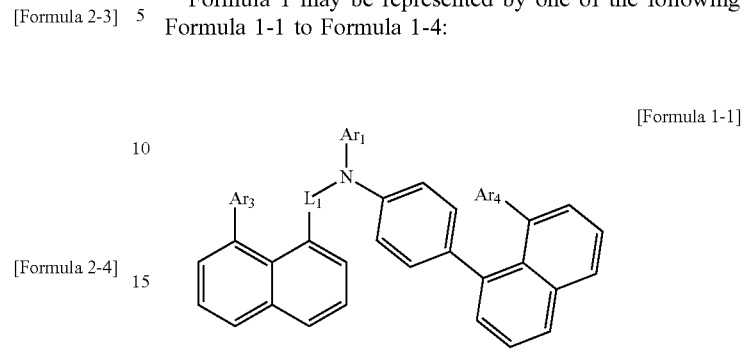

In Formula 1-1, $Ar_4$ is a substituted or unsubstituted aryl group having 6 to 20 ring carbon atoms, and $Ar_1$, $Ar_3$, and $L_1$ are the same as described above.

[Formula 1-2]

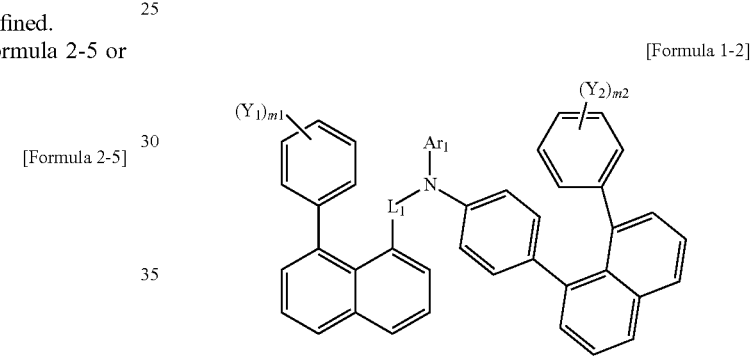

In Formula 1-2, $Y_1$ and $Y_2$ are each independently a hydrogen atom, a deuterium atom, a halogen atom, an alkyl group, or an aryl group, or may be combined with an adjacent group to form a ring, m1 and m2 are each independently an integer of 0 to 5, and $Ar_1$ and $L_1$ are the same as described above.

[Formula 1-3]

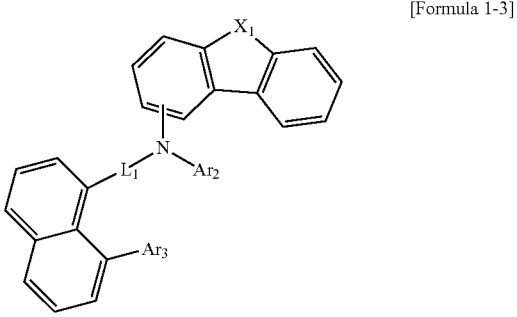

In Formula 1-3, $X_1$ is O or S, and $Ar_2$, $Ar_3$, and $L_1$ are the same as described above.

[Formula 1-4]

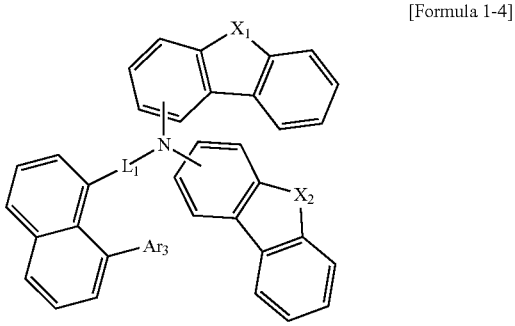

In Formula 1-4, $X_1$ and $X_2$ are each independently O or S, and $Ar_3$, and $L_1$ are the same as described above.

Embodiments are also directed to an organic electroluminescence device including a first electrode, a hole transport region disposed on the first electrode, an emission layer disposed on the hole transport region, an electron transport region disposed on the emission layer, and a second electrode disposed on the electron transport region. The hole transport region includes an amine compound represented by Formula 1.

The hole transport region may include a hole injection layer disposed on the first electrode, and a hole transport layer disposed on the hole injection layer. The hole transport layer may include the amine compound represented by Formula 1.

The hole transport layer may contact the emission layer.

The hole transport region may include a hole injection layer disposed on the first electrode, a first hole transport layer disposed on the hole injection layer, and a second hole transport layer disposed on the first hole transport layer and adjacent to the emission layer. The second hole transport layer may include the amine compound represented by Formula 1.

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
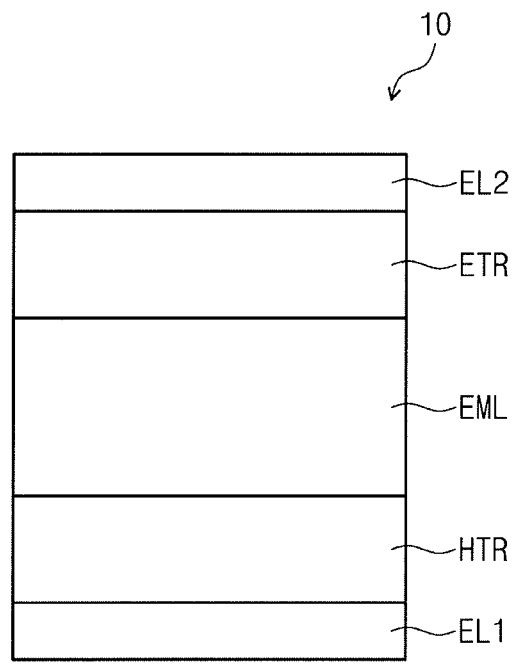
FIG. 1 illustrates a schematic cross-sectional view of an organic electroluminescence device according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "between" two layers, it can be the only layer between the two layers, or one or more intervening layers may also be present. Like reference characters refer to like elements throughout.

In the present disclosure,

in a reproduced portion of a formula represents a connection to a remaining portion of the formula.

In the present disclosure, "substituted" may refer to substituted with at least one substituent selected from deuterium, halogen, cyano, nitro, amino, silyl, boron, aryl amine, phosphine oxide, phosphine sulfide, alkyl, alkenyl, aryl, and heterocycle. In addition, each of the substituents illustrated above may be substituted or unsubstituted. For example, biphenyl may be interpreted as aryl, or phenyl substituted with phenyl.

In the present disclosure, the term "forming a ring by combining adjacent groups with each other" may refer to forming a substituted or unsubstituted hydrocarbon ring or a substituted or unsubstituted heterocyclic ring by combining adjacent groups with each other. The hydrocarbon ring may be an aliphatic hydrocarbon ring or an aromatic hydrocarbon ring. The heterocyclic ring may include an aliphatic heterocyclic ring or an aromatic heterocyclic ring. The hydrocarbon ring and heterocyclic ring may be a monocyclic ring or polycyclic ring. In addition, the ring formed by combining adjacent groups may be connected with another ring to form a spiro structure.

In the present disclosure, the term "an adjacent group" may refer to a substituent at an atom that is directly connected with another atom at which a corresponding substituent is substituted, another substituent at an atom at which a corresponding substituent is substituted, or a substituent stereoscopically disposed at the nearest position to a corresponding substituent. For example, two methyl groups in 1,2-dimethylbenzene may be interpreted as "adjacent groups", and two ethyl groups in 1,1-diethylcyclopentene may be interpreted as "adjacent groups".

In the present disclosure, the term "direct linkage" may refer to a single bond.

In the present disclosure, a halogen atom may include a fluorine atom, a chlorine atom, a bromine atom, or an iodine atom.

In the present disclosure, an alkyl group may have a linear, branched or cyclic shape. The carbon number of the alkyl group may be, for example, 1 to 30, 1 to 20, 1 to 15, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., groups.

In the present disclosure, the term "aryl" may refer to an optional functional group or substituent derived from an aromatic hydrocarbon ring. The aryl group may be a monocyclic aryl group or a polycyclic aryl group. The ring carbon number of the aryl group may be, for example, 6 to 30, 6 to 20, or 6 to 15. Examples of aryl groups may include phenyl, naphthyl, fluorenyl, anthracenyl, phenanthryl, biphenyl, terphenyl, quaterphenyl, quinquephenyl, sexiphenyl, triphenylene, pyrenyl, benzofluoranthenyl, or chrysenyl, etc. groups.

In the present disclosure, a fluorenyl group may be substituted, or two substituents may be combined with each other to form a spiro structure. For example, a fluorenyl group may be a 9,9'-spirofluorenyl group.

In the present disclosure, the term "heteroaryl" may refer to a heteroaryl group including at least one of O, N, P, S, or Si as a heteroatom. The heteroaryl group may be a monocyclic heteroaryl group or a polycyclic heteroaryl group. The ring carbon number of the heteroaryl group may be, for example, 2 to 30, or 2 to 20. Examples of the heteroaryl group may include thiophenyl, furanyl, pyrrolyl, imidazolyl, thiazolyl, oxazolyl, oxadiazolyl, triazolyl, pyridyl, bipyridyl, pyrimidyl, triazinyl, triazolyl, acridyl, pyridazinyl, pyrazinyl, quinolinyl, quinazolinyl, quinoxalinyl, phenoxazyl, phthalazinyl, pyrido pyrimidinyl, pyrido pyrazinyl, pyrazino pyrazinyl, isoquinolinyl, indolyl, carbazolyl, N-arylcarbazolyl, N-heteroaryl carbazolyl, N-alkyl carbazolyl, benzoxazolyl, benzoimidazolyl, benzothiazolyl, benzocarbazolyl, benzothiophenyl, dibenzothiophenyl, thienothiophenyl, benzofuranyl, phenanthrolinyl, thiazolyl, isoxazolyl, oxadiazolyl, thiadiazolyl, benzothiazolyl, phenothiazinyl, dibenzosilolyl, dibenzofuranyl, etc., groups.

In the present disclosure, the definition of an aryl group may be applied to an arylene group, except that an arylene group is divalent. The definition of a heteroaryl may be applied to a heteroarylene group, except that a heteroarylene group is divalent.

In the present disclosure, the term "silyl" may refer to an alkyl silyl group or an aryl silyl group. Examples of a silyl group may include trimethylsilyl, triethylsilyl, t-butyl dimethylsilyl, vinyl dimethylsilyl, propyl dimethylsilyl, triphenylsilyl, diphenylsilyl, phenylsilyl, etc., groups.

In the present disclosure, the term "boron" may include alkyl boron and aryl boron. Examples encompassed by the term "boron" may include trimethyl boron, triethyl boron, t-butyl dimethyl boron, triphenyl boron, diphenyl boron, phenyl boron, etc.

In the present disclosure, an alkenyl group may be linear or branched. The carbon number of an alkenyl group may be, for example, 2 to 30, 2 to 20, or 2 to 10. Examples of an alkenyl group may include vinyl, 1-butenyl, 1-pentenyl, 1,3-butadienyl aryl, styrenyl, styrylvinyl, etc., groups.

In the present disclosure, the carbon number of an amine group may be, for example, 1 to 30. The term "amine" may include an alkyl amine and an aryl amine group. Examples of an amine group may include methylamine, dimethylamine, phenylamine, diphenylamine, naphthylamine, 9-methyl-anthracenylamine, triphenylamine, etc., groups Hereinafter, the amine compound according to an embodiment will be explained. The amine compound according to an embodiment may be a monoamine compound. Herein, the amine compound according to any of various disclosed embodiments will sometimes be briefly referred to as "the amine compound," instead of always repeating "the amine compound according to an embodiment."

The amine compound according to an embodiment is represented by the following Formula 1:

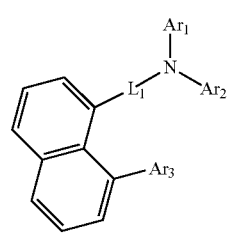

[Formula 1]

In Formula 1, $Ar_1$ and $Ar_2$ are each independently a substituted or unsubstituted aryl group having 6 to 30 ring carbon atoms, or a substituted or unsubstituted heteroaryl group having ring 2 to 30 carbon atoms. $Ar_1$ and $Ar_2$ may be each independently a substituted or unsubstituted aryl group having 6 to 20 ring carbon atoms, or a substituted or unsubstituted heteroaryl group having 2 to 20 ring carbon atoms. For example, $Ar_1$ and $Ar_2$ may be a substituted or unsubstituted phenyl group, a substituted or unsubstituted naphthylphenyl group, a substituted or unsubstituted naphthyl group, a substituted or unsubstituted biphenyl group, a substituted or unsubstituted terphenyl group, a substituted or unsubstituted phenanthryl group, a substituted or unsubstituted fluorenyl group, a substituted or unsubstituted dibenzofuranyl group, or a substituted or unsubstituted dibenzothiophenyl group. For example, $Ar_1$ and $Ar_2$ may be each independently a phenyl group, a naphthyl group, a biphenyl group, or an aryl group having 6 to 12 ring carbon atoms and substituted with an aryl silyl group. $Ar_1$ and $Ar_2$ may be the same or different from each other. For example $Ar_1$ and $Ar_2$ may be independently a substituted or unsubstituted phenyl group, a substituted or unsubstituted biphenyl group, or a substituted or unsubstituted dibenzofuranyl group. In some implementations, $Ar_1$ may be an unsubstituted phenyl group and $Ar_2$ may be a biphenyl group substituted with a triphenylsilyl group.

$Ar_3$ is a substituted or unsubstituted aryl group having 6 to 20 ring carbon atoms. $Ar_3$ may be, for example, a substituted or unsubstituted phenyl group, a substituted or unsubstituted naphthyl group, or a substituted or unsubstituted phenanthryl group. For example, $Ar_3$ may be an unsubstituted phenyl group.

If $Ar_3$ is substituted, a substituent may be at least one of deuterium, a silyl group, an alkyl group, or an aryl group.

$Ar_3$ may not include a heteroaryl group. For example, $Ar_3$ is a substituted or unsubstituted aryl group having 6 to 20 ring carbon atoms, and if substituted, $Ar_3$ may be substituted with a substituent other than a heteroaryl group. If $Ar_3$ is substituted with a heteroaryl group, stabilization effect of the relatively unstable heteroaryl group by nitrogen of arylamine is insignificant, and if applied to an organic electroluminescence device, efficiency may be reduced.

At least one of $Ar_1$ or $Ar_2$ may be a heteroaryl group, or at least one of $Ar_1$ or $Ar_2$ may include a polycyclic ring. The term "include a polycyclic ring" may include a case where $Ar_1$ and/or $Ar_2$ themselves are substituents having a polycyclic ring structure, and a case where $Ar_1$ and/or $Ar_2$ are substituted with a substituent having a polycyclic structure. Examples of the case where $Ar_1$ and/or $Ar_2$ are substituted with a substituent having a polycyclic structure may include a phenyl group substituted with a naphthyl group, a phenyl group substituted with a biphenyl group, etc. Examples of the case where $Ar_1$ and/or $Ar_2$ themselves are substituents having a polycyclic ring structure may include a substituted or unsubstituted anthracene group, a substituted or unsubstituted biphenyl group, a substituted or unsubstituted terphenyl group, a substituted or unsubstituted fluorenyl group, a substituted or unsubstituted dibenzofuran group, a substituted or unsubstituted dibenzothiophene group, etc.

At least one of $Ar_1$ or $Ar_2$ may be, though not limited to, a substituted or unsubstituted naphthylphenyl group, a substituted or unsubstituted phenanthryl group, a substituted or unsubstituted fluorenyl group, a substituted or unsubstituted dibenzofuranyl group, or a substituted or unsubstituted dibenzothiophenyl group.

$L_1$ is a substituted or unsubstituted arylene group having 6 to 30 ring carbon atoms, or a substituted or unsubstituted heteroarylene group having 2 to 30 ring carbon atoms. $L_1$ may be a substituted or unsubstituted arylene group having 6 to 15 ring carbon atoms, or a substituted or unsubstituted heteroarylene having 2 to 15 ring carbon atoms. $L_1$ may be a substituted or unsubstituted phenylene group, a substituted or unsubstituted divalent biphenyl group, a substituted or unsubstituted dibenzofuranylene group, or a substituted or unsubstituted dibenzothiophenylene group.

$L_1$ may be a substituted or unsubstituted arylene group having 6 to 30 ring carbon atoms, a substituted or unsubstituted heteroarylene group having 2 to 30 ring carbon atoms, or a connected group of the substituted or unsubstituted arylene group having 6 to 30 ring carbon atoms and the substituted or unsubstituted heteroarylene group having 2 to 30 ring carbon atoms. For example, $L_1$ may be a connected group of a substituted or unsubstituted phenylene group and a substituted or unsubstituted pyridylene group.

$L_1$ may be represented by the following Formula 2-1 or 2-2:

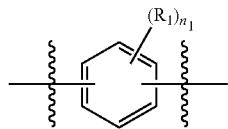

[Formula 2-1]

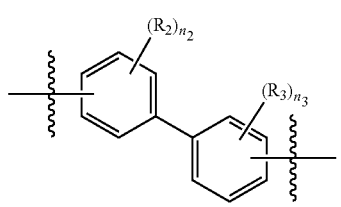

[Formula 2-2]

In Formulae 2-1 and 2-2, $R_1$ to $R_3$ may be each independently a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms.

In addition, $n_1$ to $n_3$ may be each independently an integer of 0 to 4. A case where n is 0 may indicate that the corresponding carbons have a hydrogen atom. In the case where $n_1$ is 0, $L_1$ represented by Formula 2-1 may be unsubstituted with $R_1$. In the case where $n_1$ is an integer of 2 or more, a plurality of $R_1$ may be the same or different. In the case where $n_2$ is 0, $L_1$ represented by Formula 2-1 may be unsubstituted with $R_2$. In the case where $n_2$ is an integer of 2 or more, a plurality of $R_2$ may be the same or different. In the case where $n_3$ is 0, $L_1$ represented by Formula 2-1 may be unsubstituted with $R_3$. In the case where $n_3$ is an integer of 2 or more, a plurality of $R_3$ may be the same or different.

$L_1$ may be represented by one of the following Formulae 2-3 to 2-6:

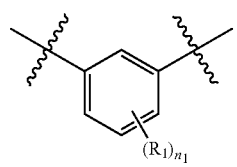

[Formula 2-3]

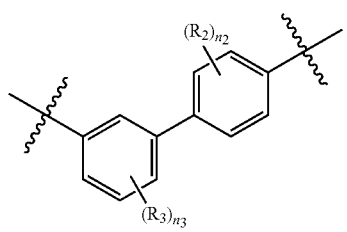

[Formula 2-4]

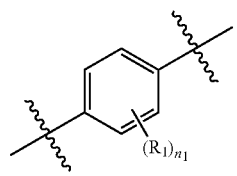

[Formula 2-5]

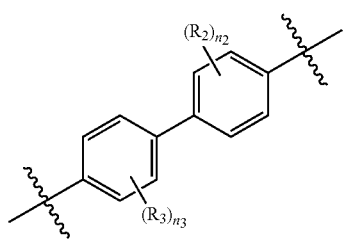

[Formula 2-6]

In Formulae 2-3 to 2-6, $R_1$ to $R_3$, and $n_1$ to $n_3$ may be the same as defined above.

Formula 1 may be represented by the following Formula 1-1:

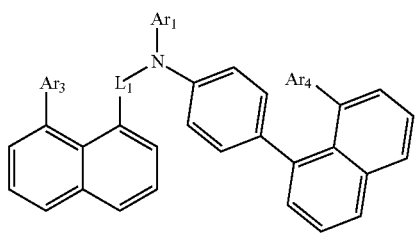

[Formula 1-1]

In Formula 1-1, $Ar_4$ is a substituted or unsubstituted aryl group having 6 to 20 ring carbon atoms, and $Ar_1$, $Ar_3$, and $L_1$ are the same as defined in Formula 1.

Formula 1 may be represented by the following Formula 1-2:

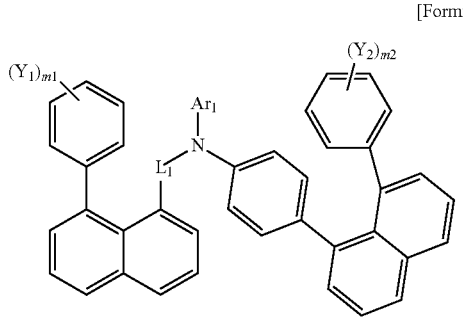

[Formula 1-2]

In Formula 1-2, $Y_1$ and $Y_2$ are each independently a hydrogen atom, a deuterium atom, a halogen atom, an alkyl group, or an aryl group, or may be combined with an adjacent group to form a ring, m1 and m2 are each independently an integer of 0 to 5, and $Ar_1$ and $L_1$ are the same as defined in Formula 1.

In Formula 1-2, if m1 is 2 or more, a plurality of $Y_1$ groups are the same or different, and if m2 is 2 or more, a plurality of $Y_2$ groups may be the same or different.

In Formula 1-2, if m1 is 1, $Y_1$ may be a substituent other than a hydrogen atom, and if m2 is 1, $Y_2$ may be a substituent other than a hydrogen atom.

Formula 1 may be represented by the following Formula 1-3:

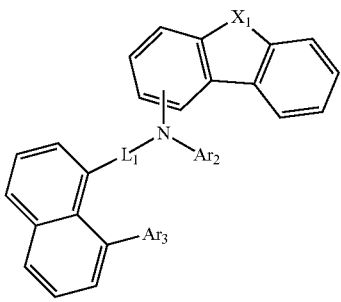

[Formula 1-3]

In Formula 1-3, $X_1$ is O or S, and $Ar_2$, $Ar_3$, and $L_1$ are the same as defined in Formula 1.

Formula 1 may be represented by the following Formula 1-4:

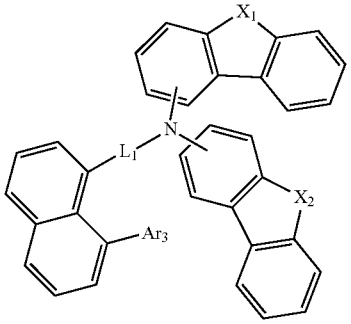

[Formula 1-4]

In Formula 1-4, $X_1$ and $X_2$ are each independently O or S, and $Ar_3$, and $L_1$ are the same as defined in Formula 1.

When the amine compound according to an embodiment has $L_1$ represented by Formula 2-3 or 2-4, a naphthyl group and an amine group may be respectively connected at meta positions of a substituted or unsubstituted phenylene group, which is at least a portion of a linker. When the amine compound according to an embodiment has $L_1$ represented by Formula 2-5 or 2-6, a naphthyl group and an amine group may be respectively connected at para positions of a substituted or unsubstituted phenylene group, which is at least a portion of a linker.

The amine compound represented by Formula 1 may be represented by the following Formula 3:

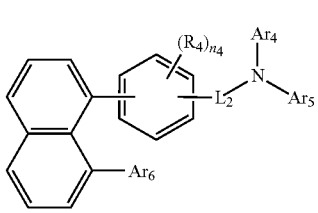

[Formula 3]

In Formula 3, $Ar_4$ and $Ar_5$ are each independently a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms. $Ar_4$ and $Ar_5$ may be each independently a substituted or unsubstituted aryl group having 6 to 20 ring carbon atoms, or a substituted or unsubstituted heteroaryl group having 2 to 20 ring carbon atoms. $Ar_4$ and $Ar_5$ may be each independently a substituted or unsubstituted phenyl group, a substituted or unsubstituted naphthyl group, a substituted or unsubstituted biphenyl group, a substituted or unsubstituted terphenyl group, a substituted or unsubstituted phenanthryl group, a substituted or unsubstituted fluorenyl group, a substituted or unsubstituted dibenzofuranyl group, or a substituted or unsubstituted dibenzothiophenyl group. $Ar_4$ and $Ar_5$ may be each independently a phenyl group, a naphthyl group, a biphenyl group, or an aryl group having 6 to 12 ring carbon atoms and substituted with an aryl silyl group. $Ar_4$ and $Ar_5$ may be the same or different. For example, $Ar_4$ and $Ar_5$ may be a substituted or unsubstituted phenyl group, a substituted or unsubstituted biphenyl group, or a substituted or unsubstituted dibenzofuranyl group at the same time. Alternatively, $Ar_4$ may be an unsubstituted phenyl group, and $Ar_5$ may be a biphenyl group substituted with a triphenylsilyl group.

$Ar_6$ is a substituted or unsubstituted aryl group having 6 to 20 ring carbon atoms. $Ar_6$ may be a substituted or unsubstituted phenyl group, a substituted or unsubstituted naphthyl group, or a substituted or unsubstituted phenanthryl group. For example, $Ar_6$ may be an unsubstituted phenyl group.

$L_2$ is a direct linkage, a substituted or unsubstituted arylene group having 6 to 20 ring carbon atoms, or a substituted or unsubstituted heteroarylene group having 2 to 20 ring carbon atoms. $L_2$ may be a direct linkage, or a substituted or unsubstituted phenylene group.

$R_4$ is a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms.

In addition, $n_4$ is an integer of 0 to 4. In the case where $n_4$ is 0, the amine compound represented by Formula 3 may be unsubstituted with $R_4$. In the case where $n_4$ is an integer of 2 or more, a plurality of $R_4$ may be the same or different.

The compound represented by Formula 3 may be represented by the following Formula 3-1:

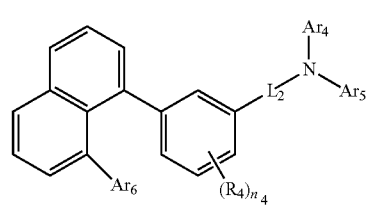

[Formula 3-1]

In Formula 3-1, $Ar_4$, $Ar_5$, $Ar_6$, $L_2$, $R_4$, and $n_4$ are the same as defined above.

The compound represented by Formula 3-1 may be represented by the following Formula 3-1-1 or 3-1-2:

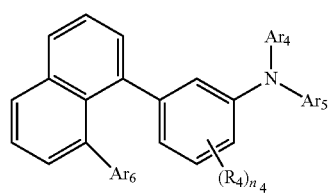

[Formula 3-1-1]

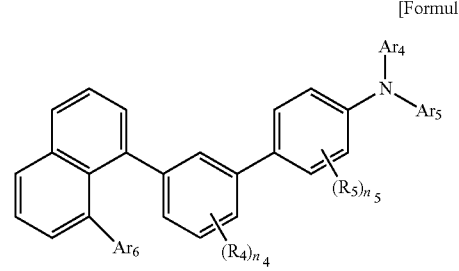

[Formula 3-1-2]

In Formulae 3-1-1 and 3-1-2, $Ar_4$, $Ar_5$, $Ar_6$, $R_4$, and $n_4$ are the same as defined above.

In Formula 3-1-2, $R_5$ may be a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms. $n_5$ may be an integer of 0 to 4. In the case where $n_5$ is 0, the amine compound represented by Formula 3-1-2 may be unsubstituted with $R_5$. In the case where $n_5$ is an integer of 2 or more, a plurality of $R_5$ may be the same or different.

The compound represented by Formula 3 may be represented by the following Formula 3-2:

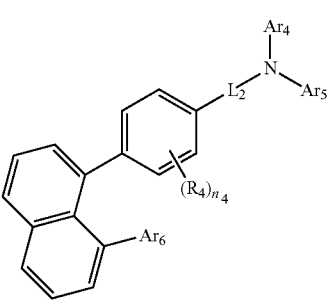

[Formula 3-2]

In Formula 3-2, $Ar_4$, $Ar_5$, $Ar_6$, $L_2$, $R_4$, and $n_4$ are the same as defined above.

The compound represented by Formula 3-2 may be represented by the following Formula 3-2-1 or 3-2-2:

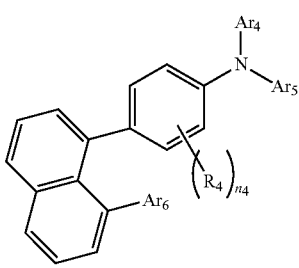

[Formula 3-2-1]

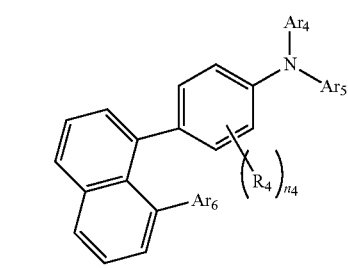

[Formula 3-2-2]

In Formulae 3-2-1 and 3-2-2, $Ar_4$, $Ar_5$, $Ar_6$, $R_4$, and $n_4$ are the same as defined above.

In Formula 3-2-2, $R_6$ may be a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms. $n_6$ may be an integer of 0 to 4. In the case where $n_6$ is 0, the amine compound represented by Formula 3-2-2 may be unsubstituted with $R_6$. In the case where $n_6$ is an integer of 2 or more, a plurality of $R_6$ may be the same or different.

The amine compound according to an embodiment of the present invention, represented by one of Formulae 3-1-1 to 3-2-2 corresponds to Formula 1 in which $L_1$ is a substituted or unsubstituted phenyl group, or a substituted or unsubstituted divalent biphenyl group.

In the case where the amine compound according to an embodiment of the present invention is represented by Formula 3-1, at the meta positions of a substituted or unsubstituted phenylene group, which is at least a portion of a linker, a naphthyl group and an amine group may be respectively connected. In the case where the amine compound according to an embodiment of the present invention is represented by Formula 3-2, at the para positions of a substituted or unsubstituted phenylene group, which is at least a portion of a linker, a naphthyl group and an amine group may be respectively connected.

The amine compound represented by Formula 1 may be, for example, any one selected from the compounds represented in the following Compound Group 1.

[Compound Group 1]

1

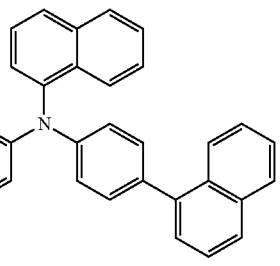

2

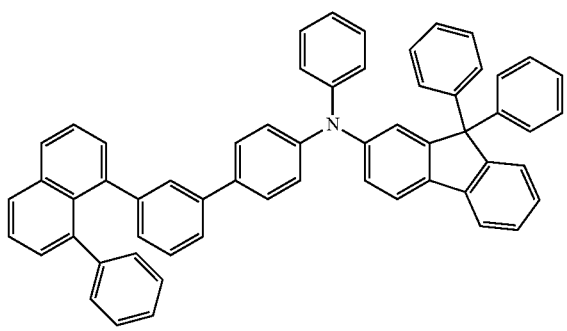

3

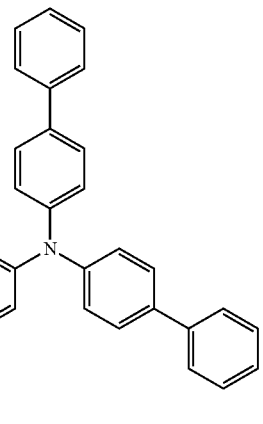

4

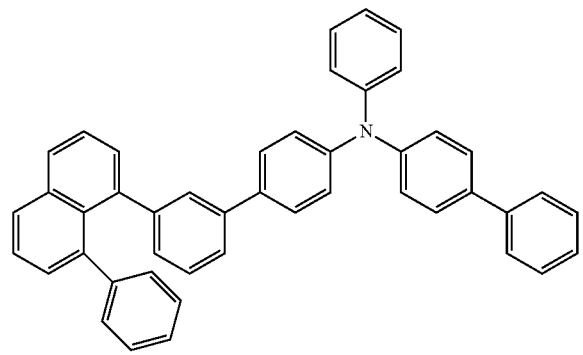

5

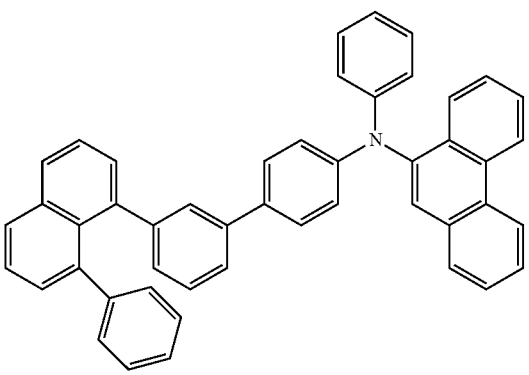

6

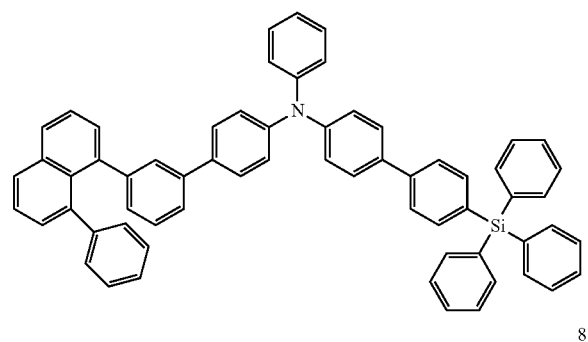
7
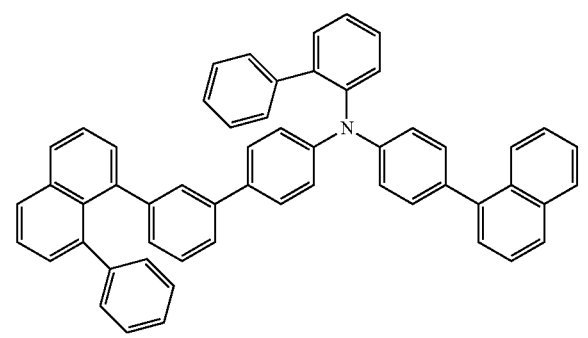
8
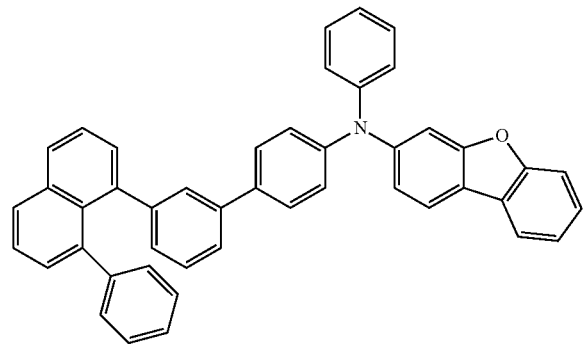
9
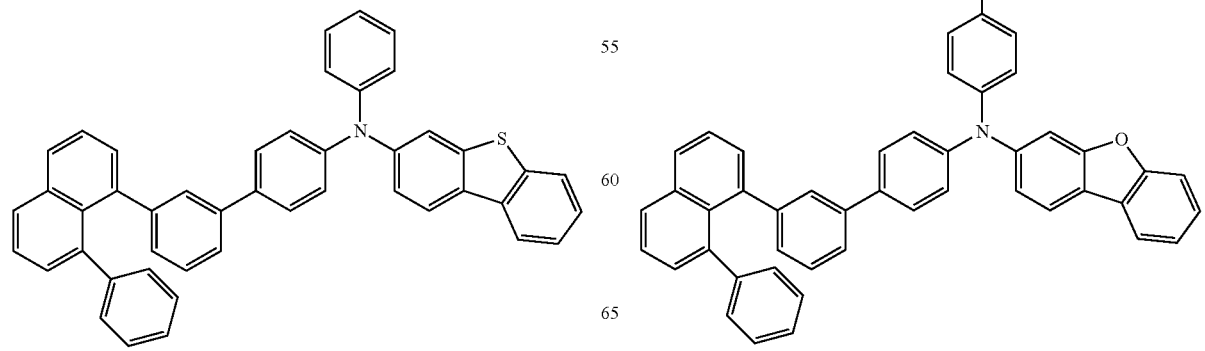
10
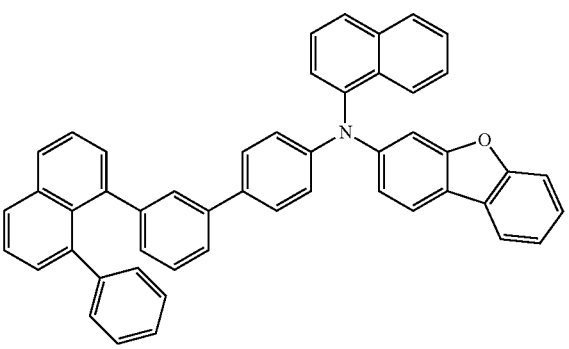
11
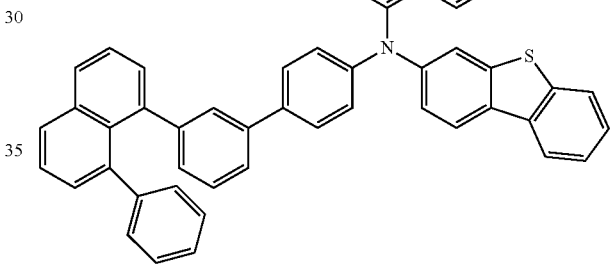
12
13

14
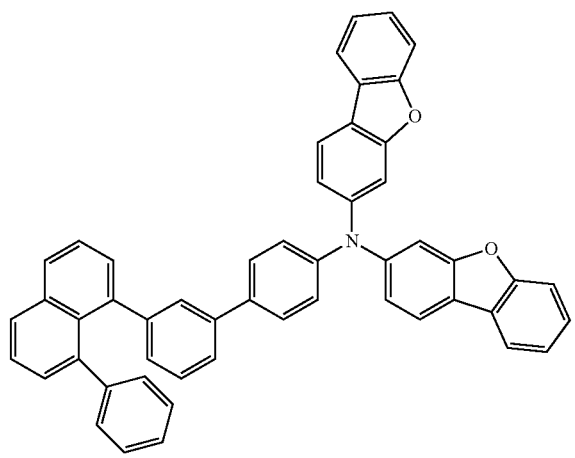
15
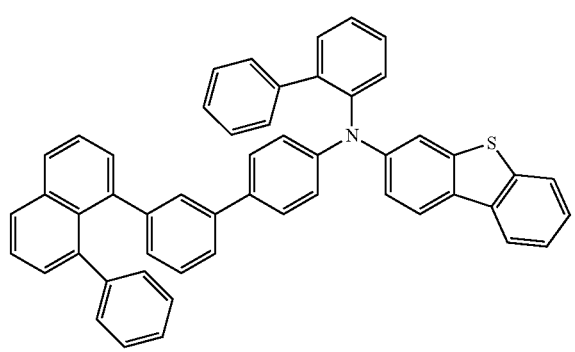
16
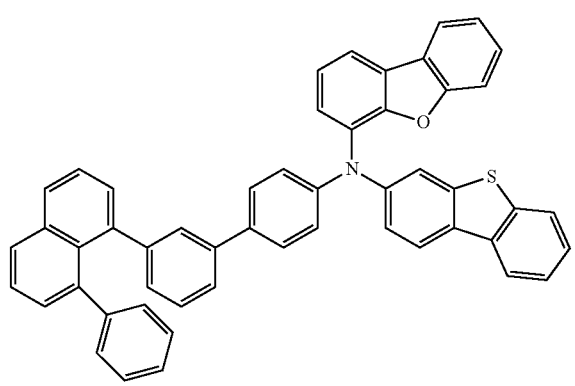
17
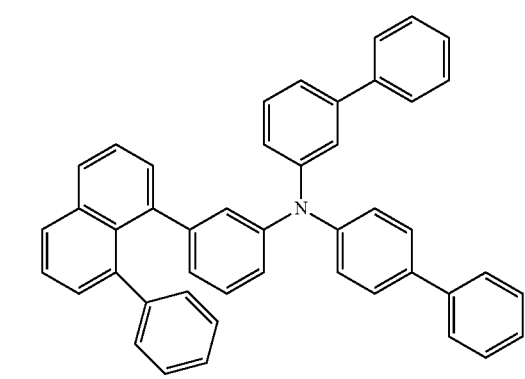
18
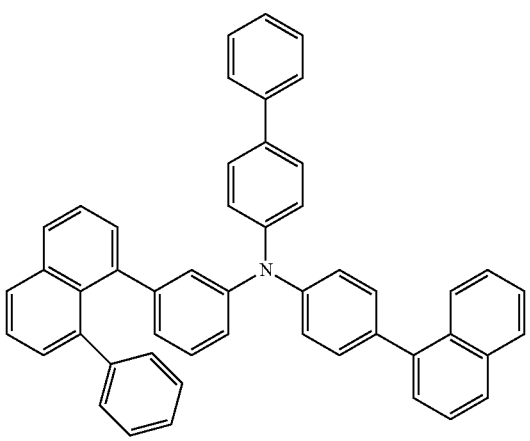
19
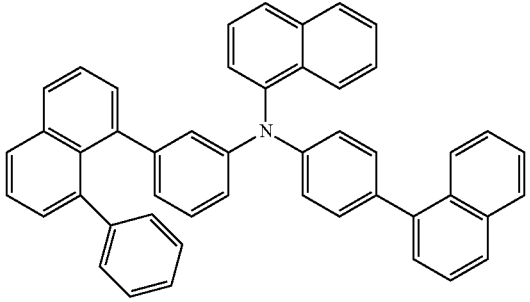
20
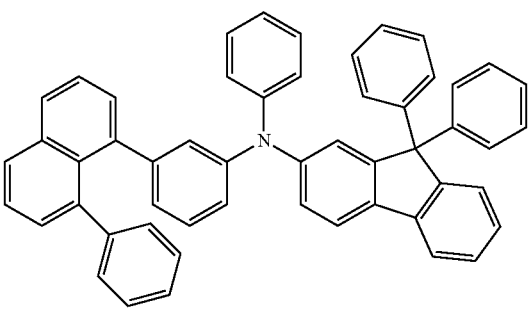
21
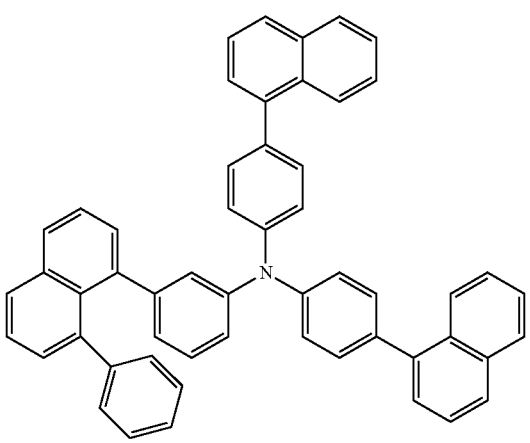

22
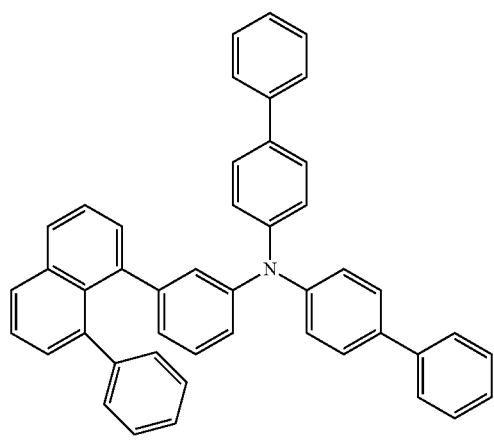
23
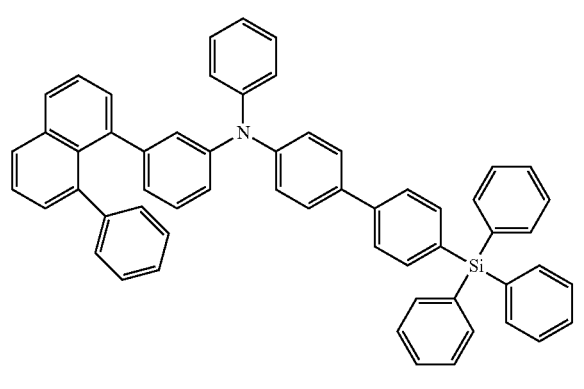
24
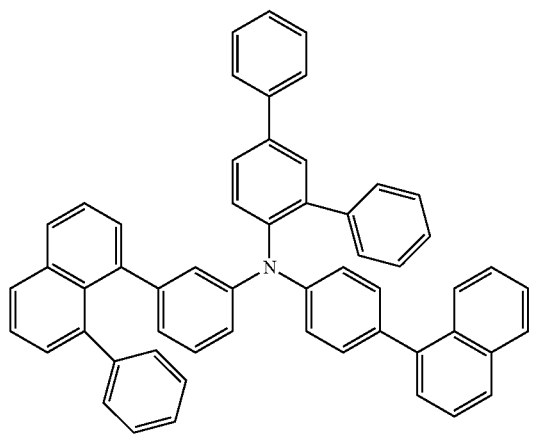
25
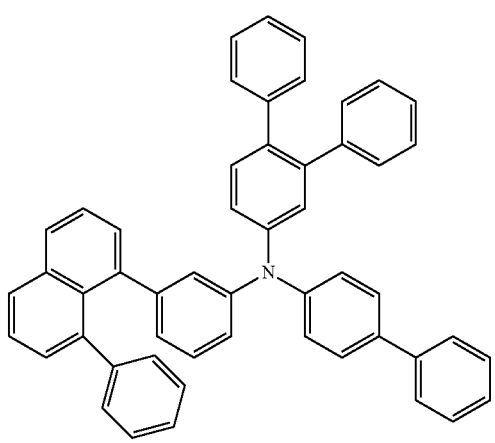
26
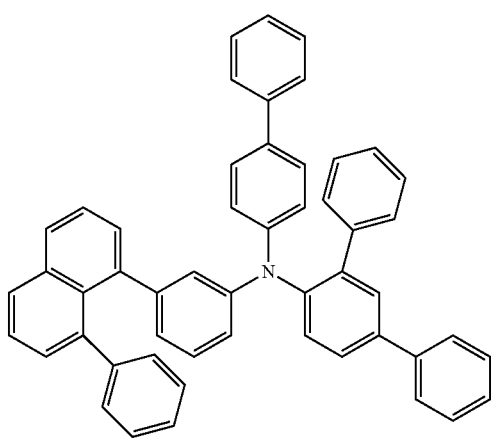
27
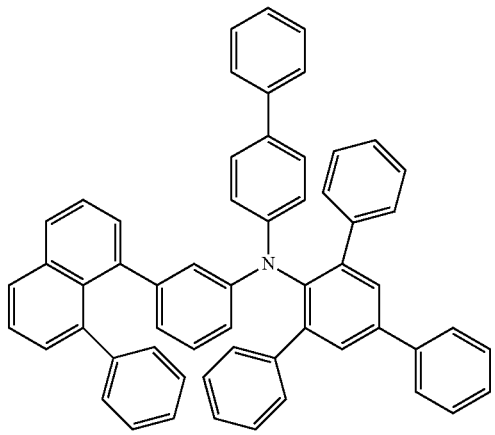

28
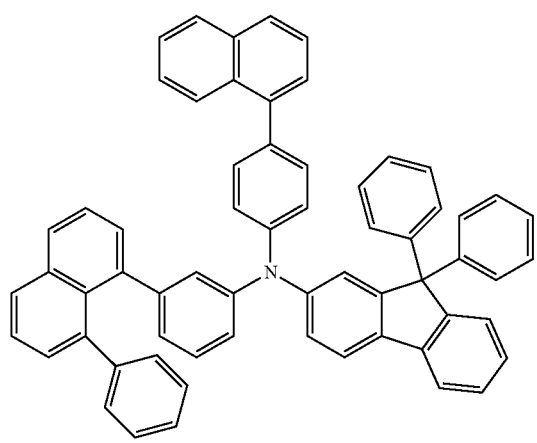
29
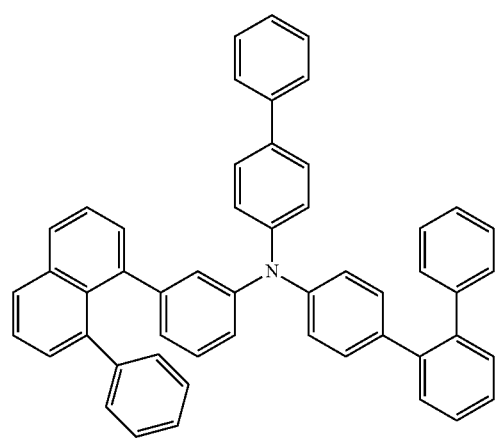
30
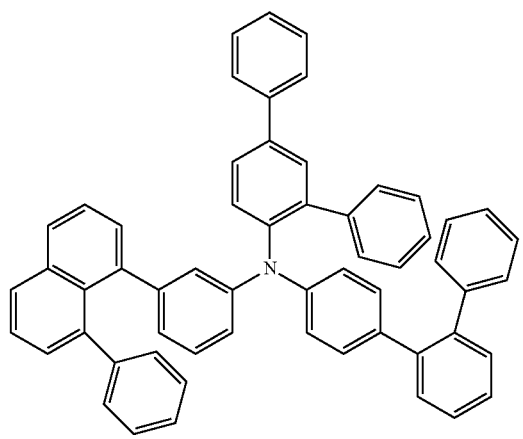
31
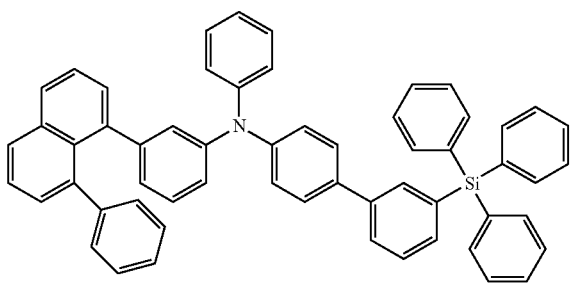
32
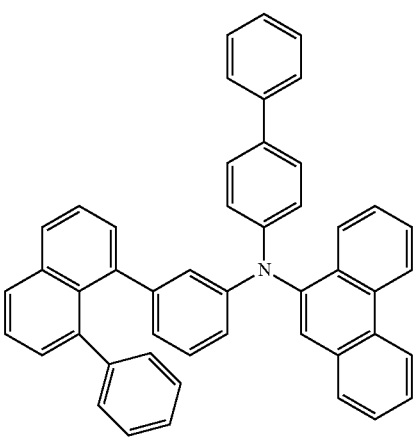
33
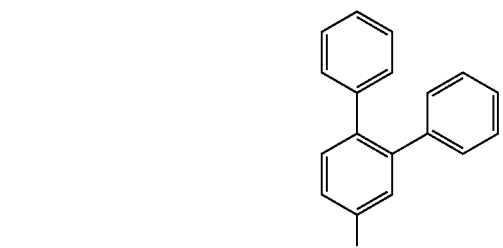
34
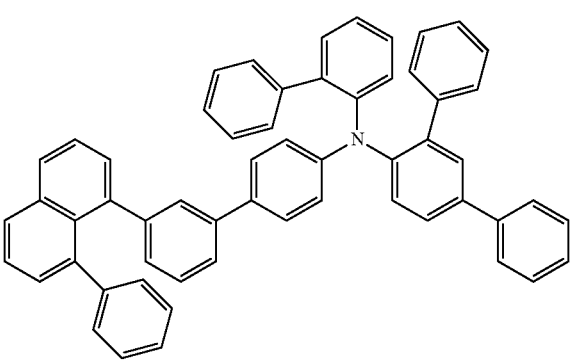

35
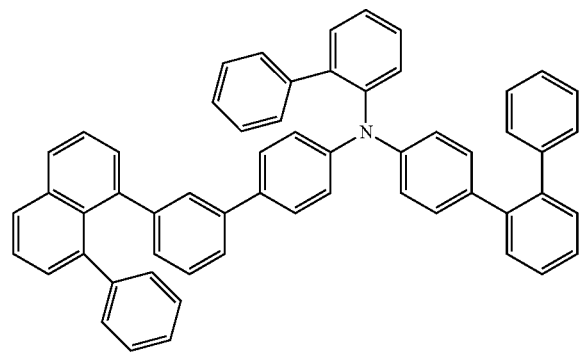
36
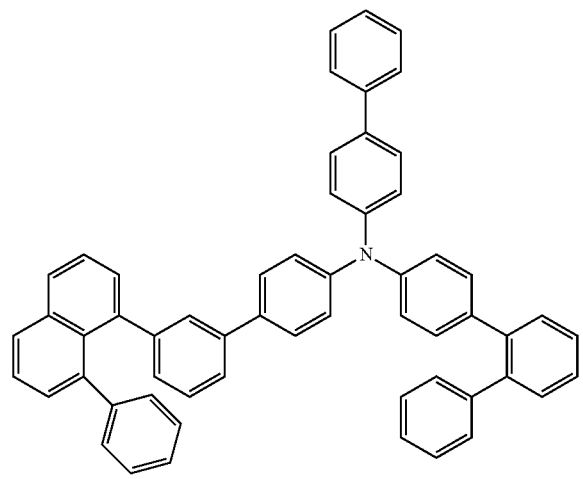
37
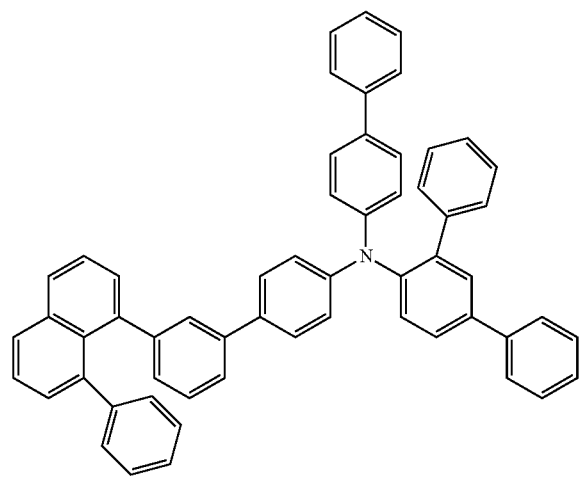
38
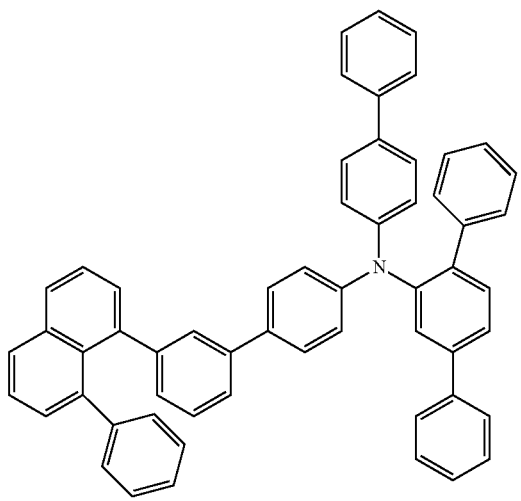
39
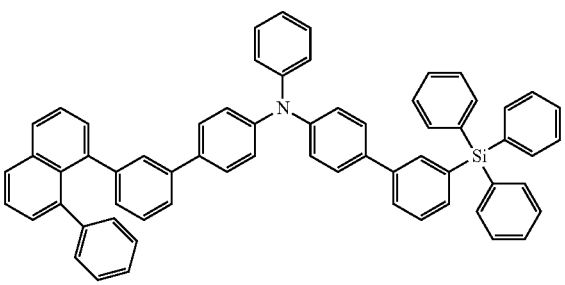
40
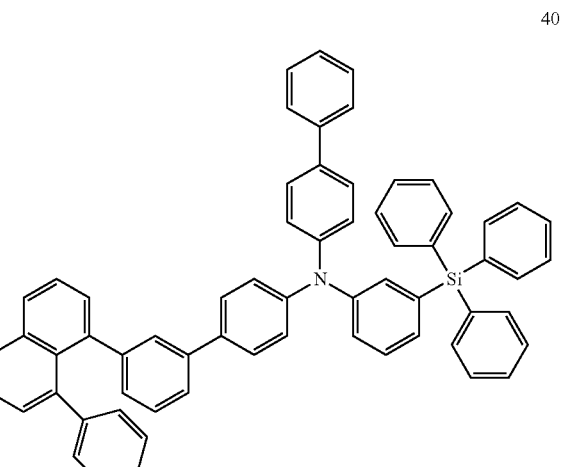

41
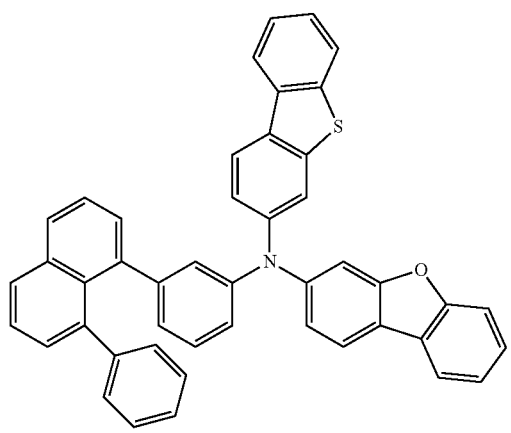
42
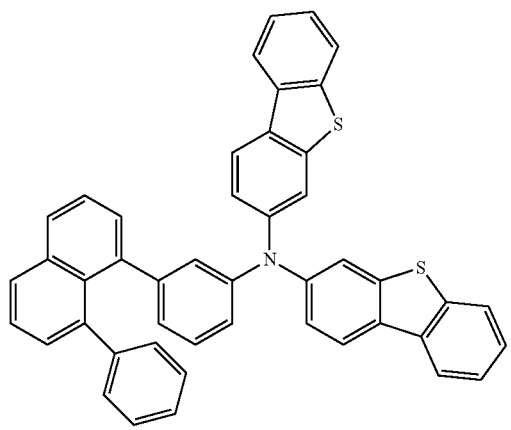
43
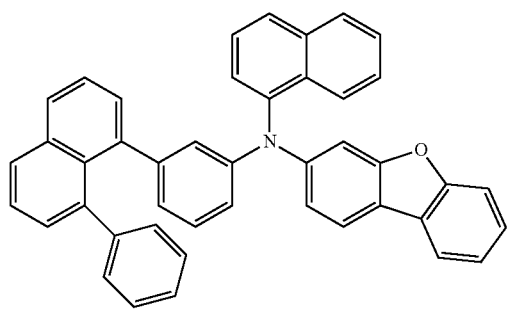
44
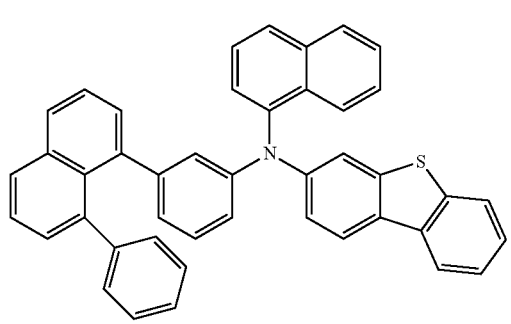
45
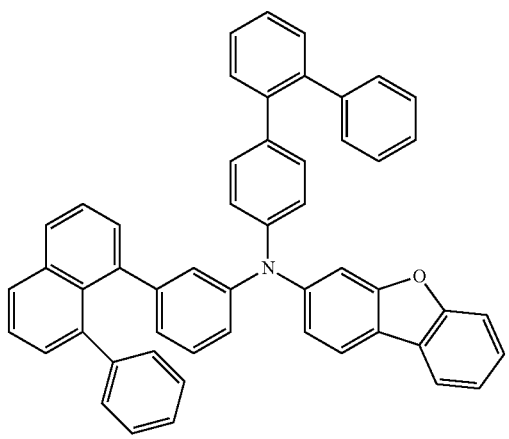
46
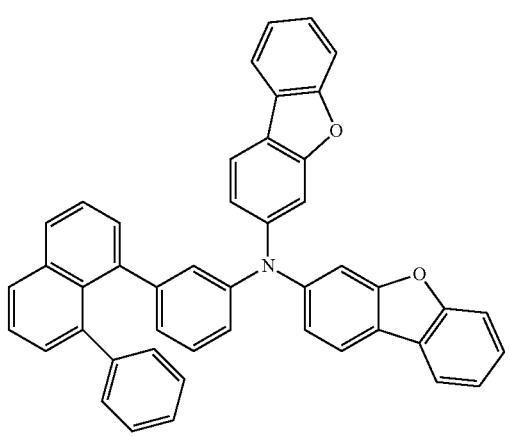
47
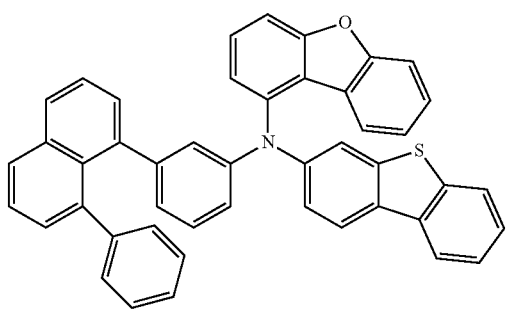
48
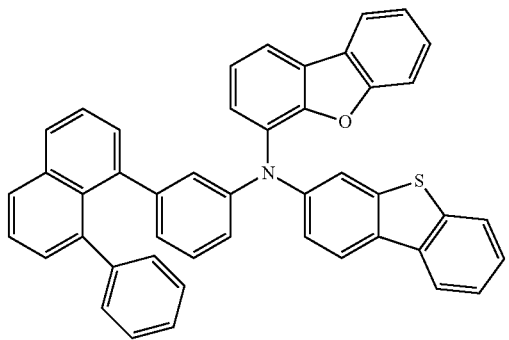

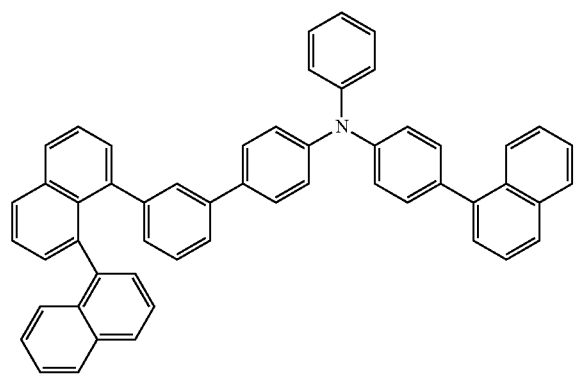
49
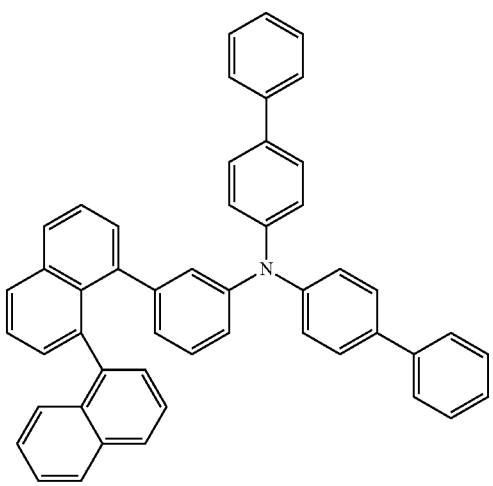
52
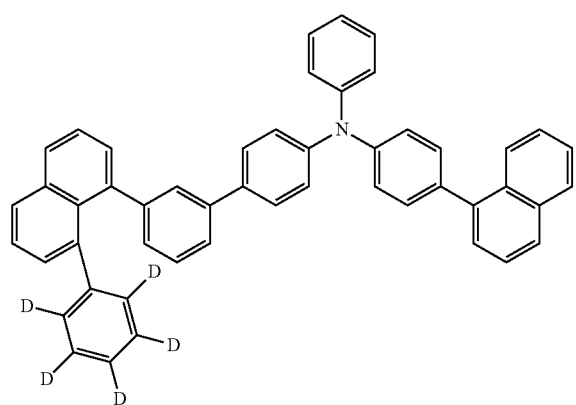
50
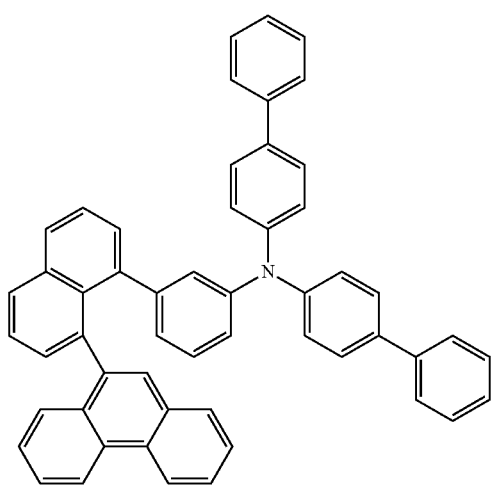
51
The amine compound represented by Formula 1 may be, for example, any one selected from the group compounds represented in the following Compound Group 2.
[Compound Group 2]
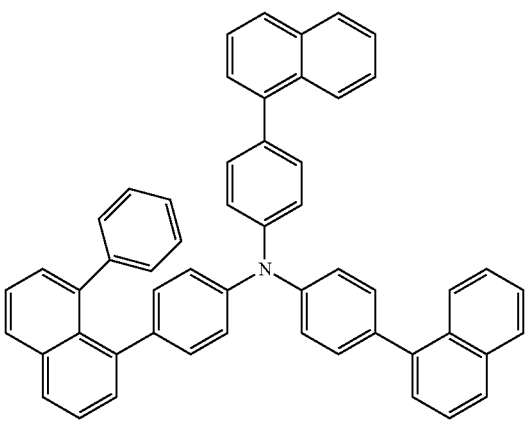
53
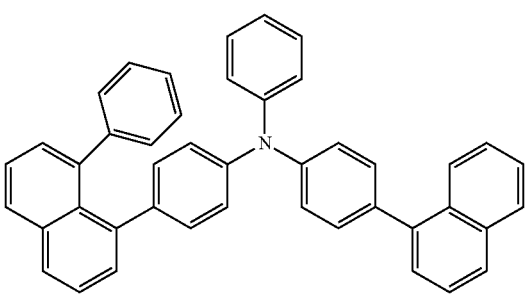
54

55
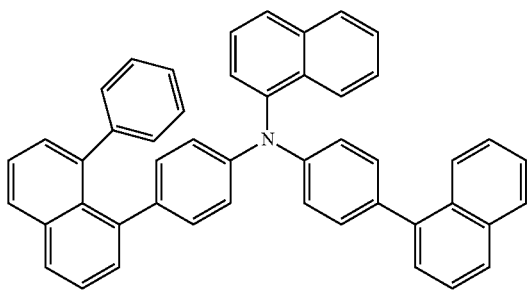
56
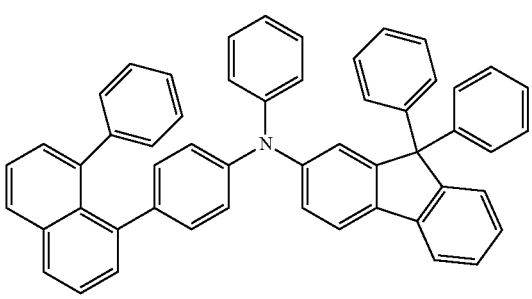
57
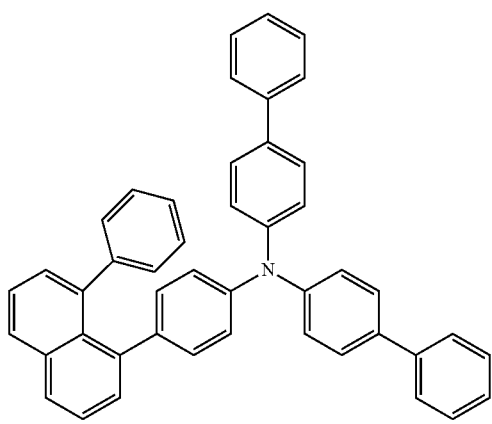
58
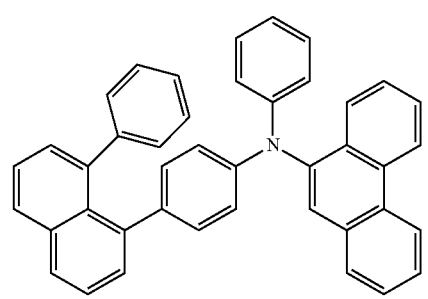
59
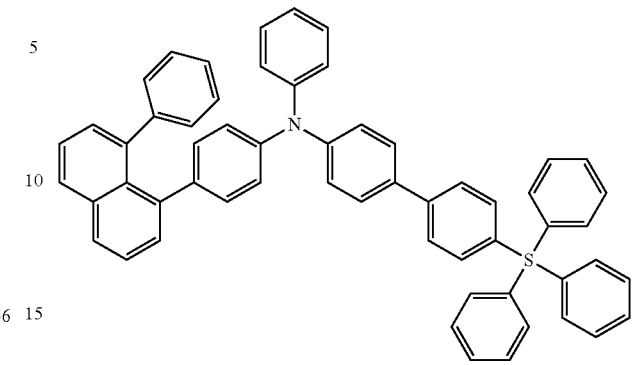
60
61
62
63
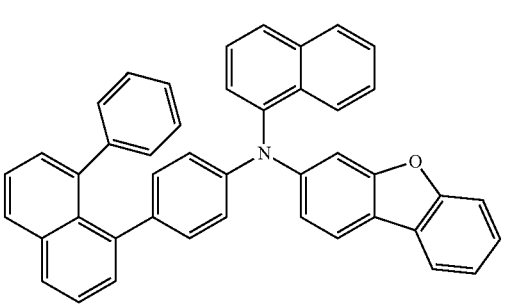

33
-continued
64
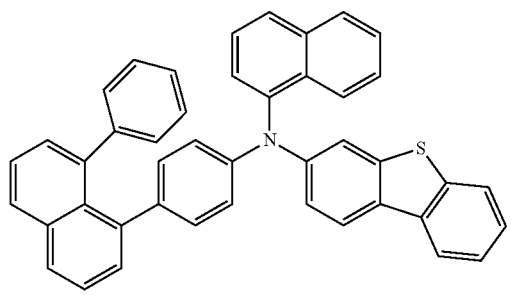
65
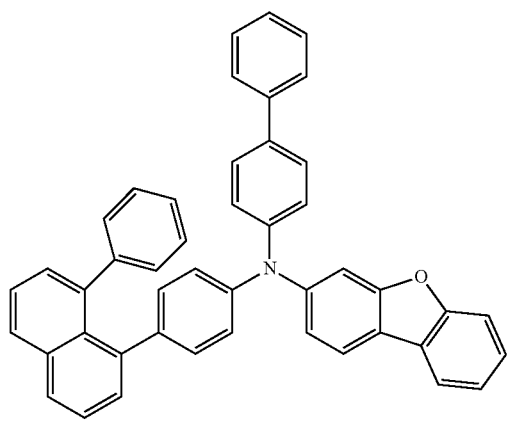
66
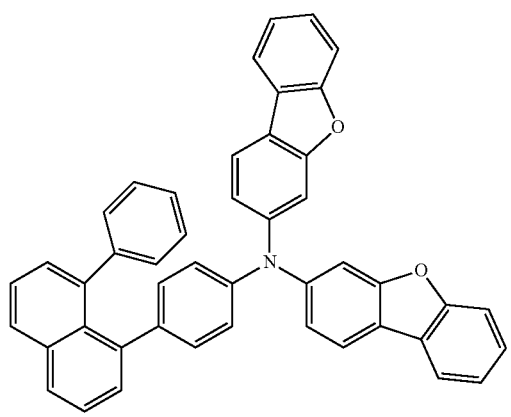
67
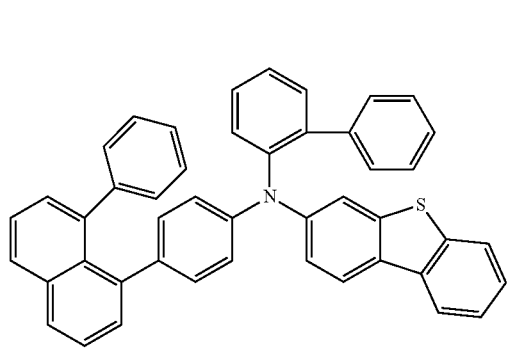
34
-continued
68
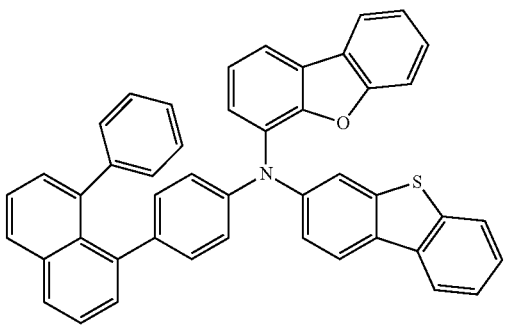
69
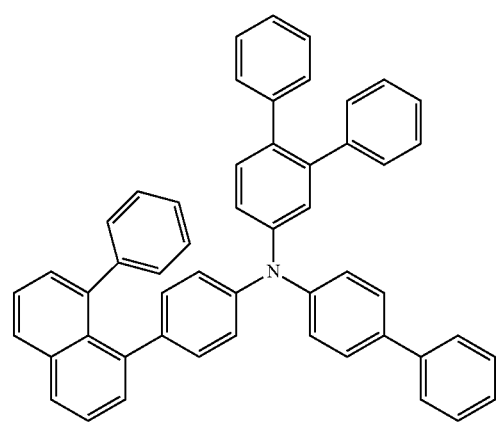
70
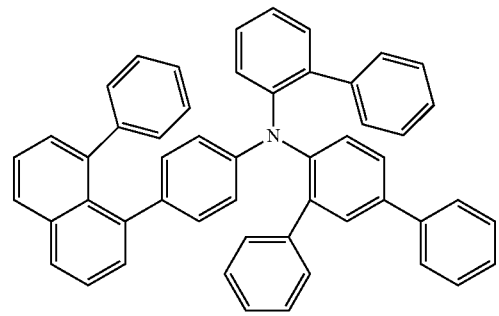
71
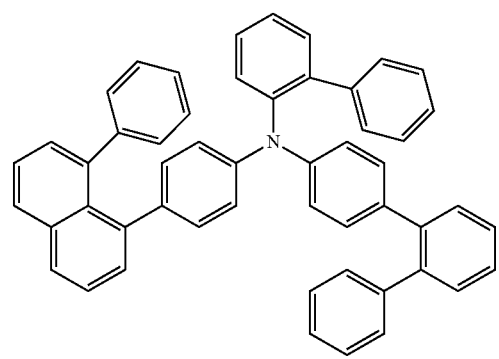

-continued
72
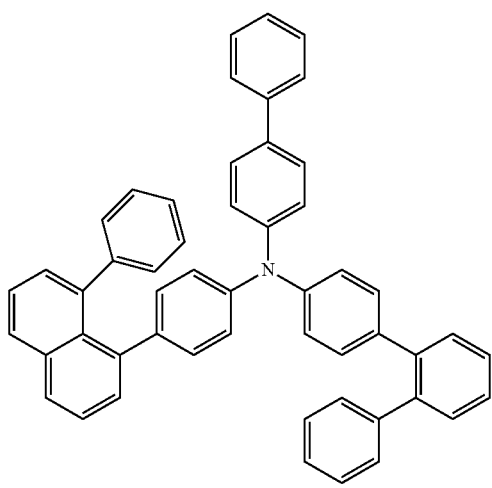
73
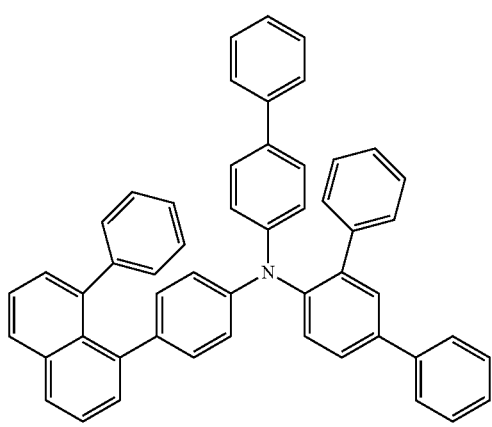
74
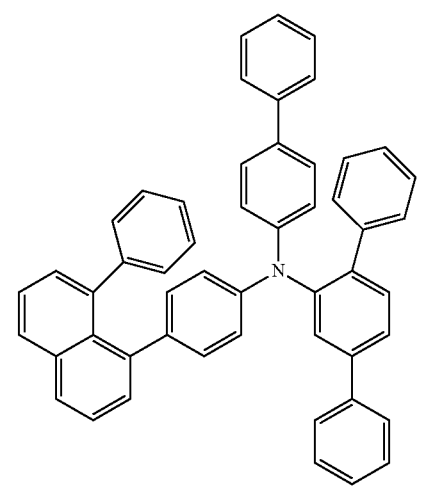
-continued
75
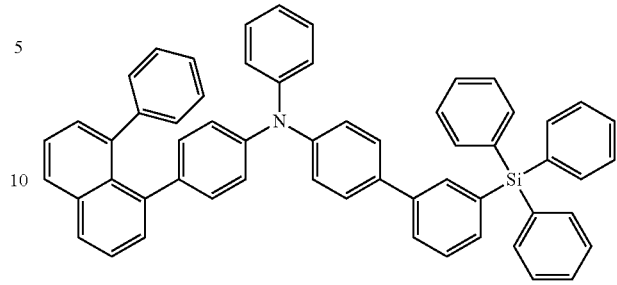
76
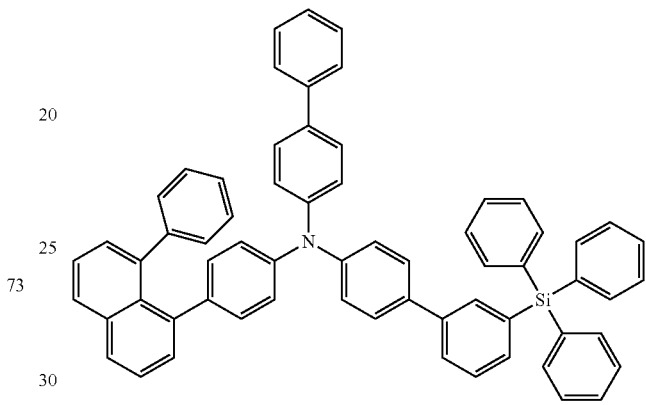
77
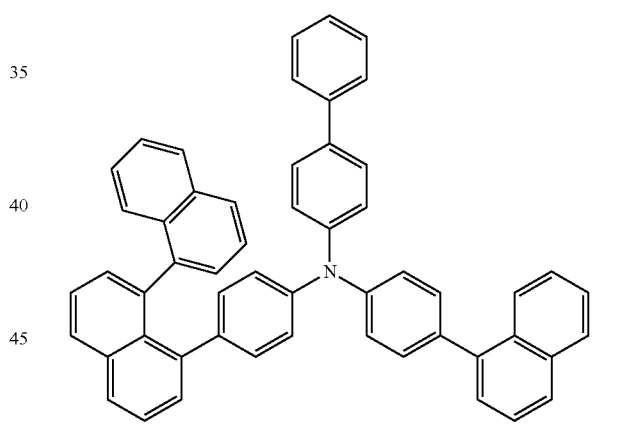
78
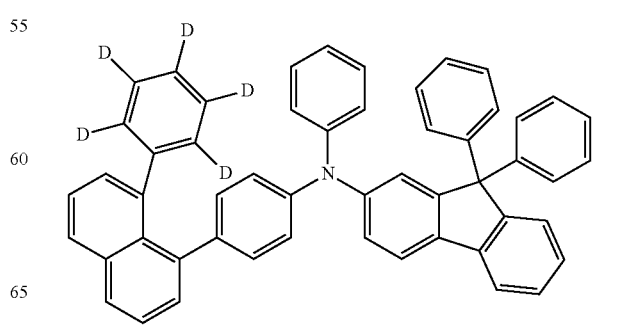

37
-continued
79
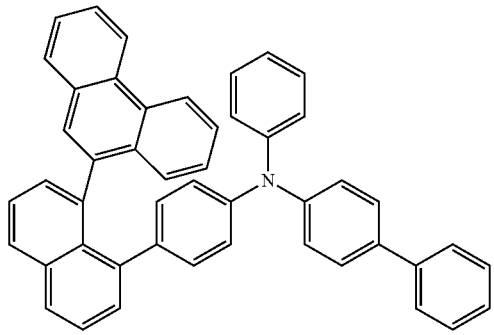
80
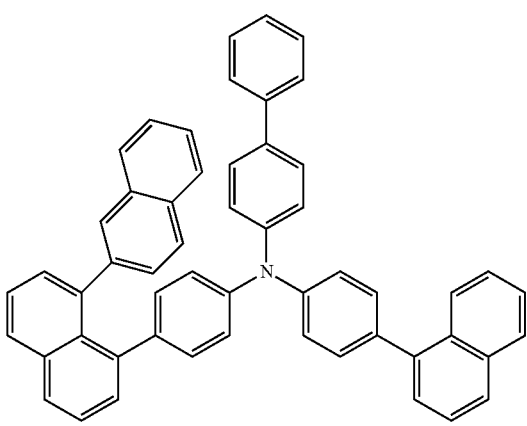
81
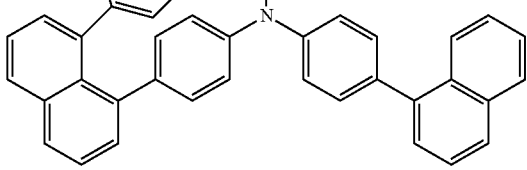
82
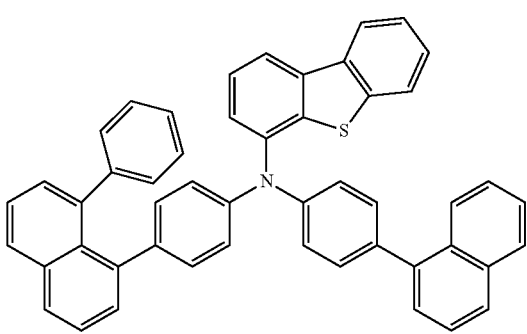
38
-continued
83
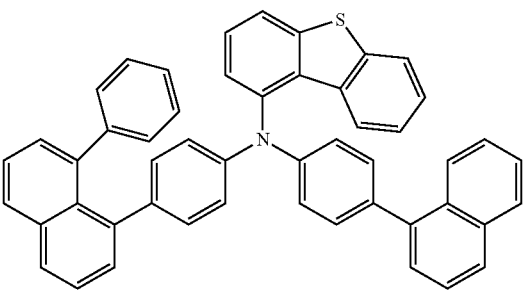
84
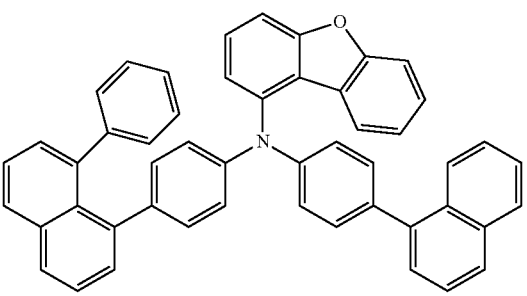
85
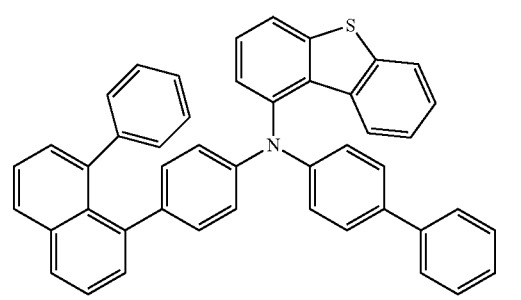
86
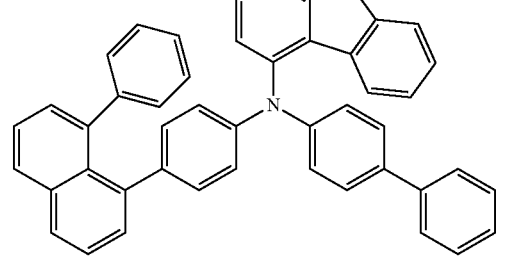
87
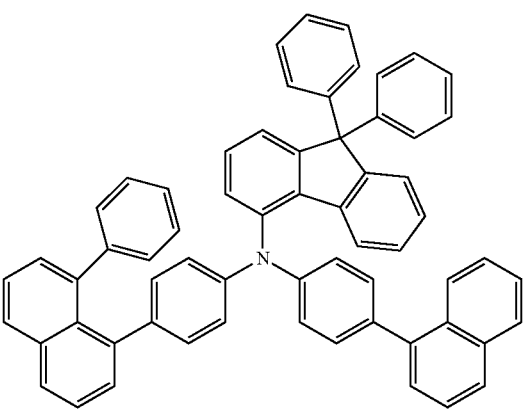

88
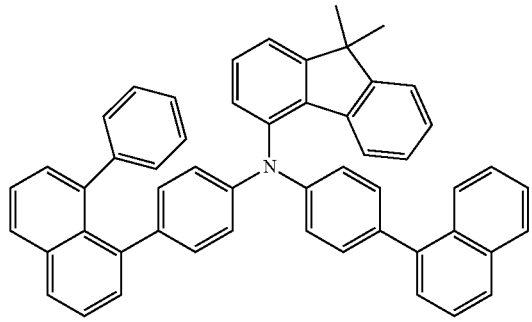
89
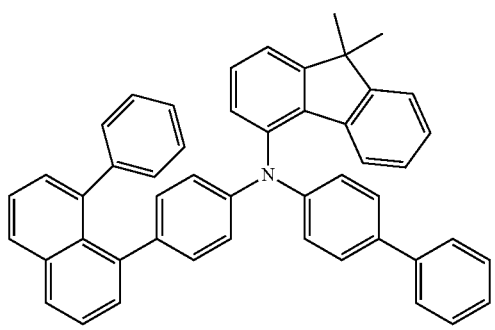
90
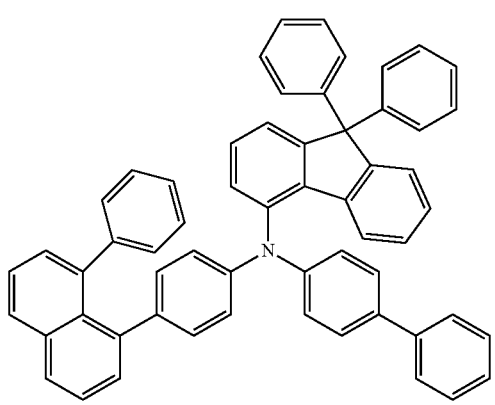
91
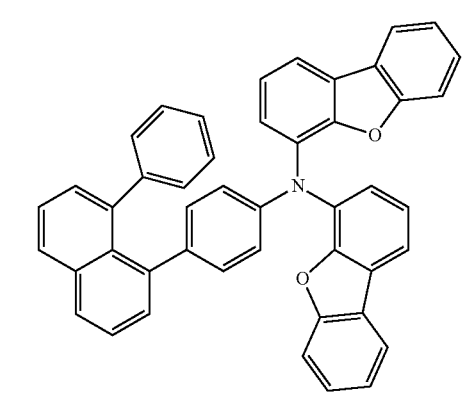
92
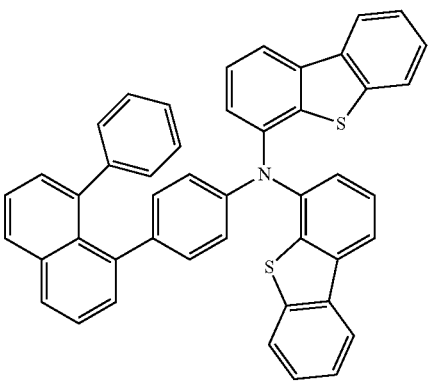
93
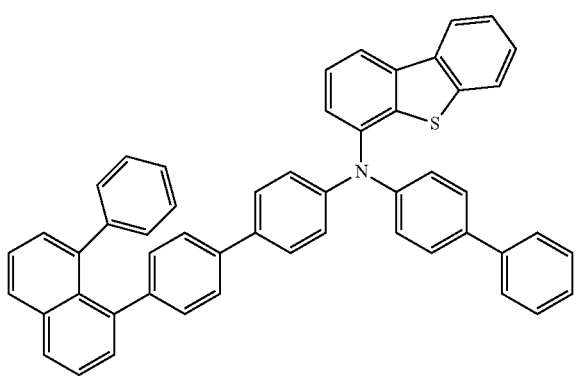
94
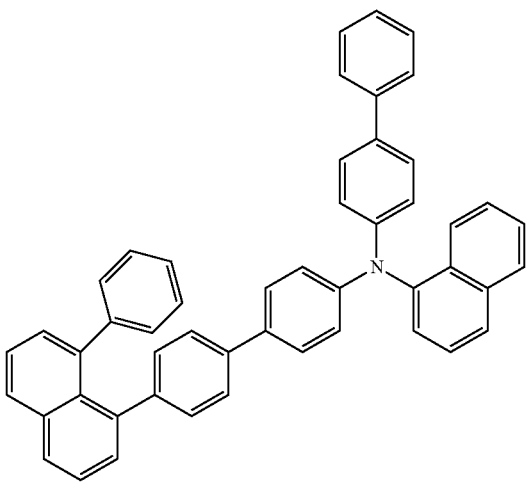
95
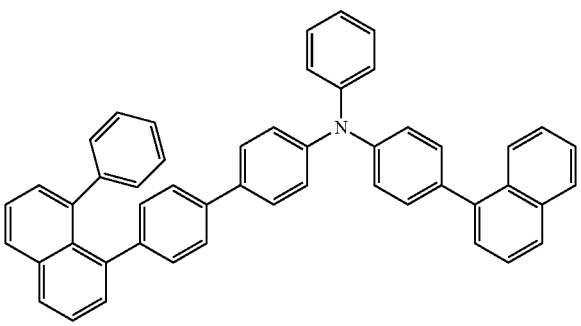

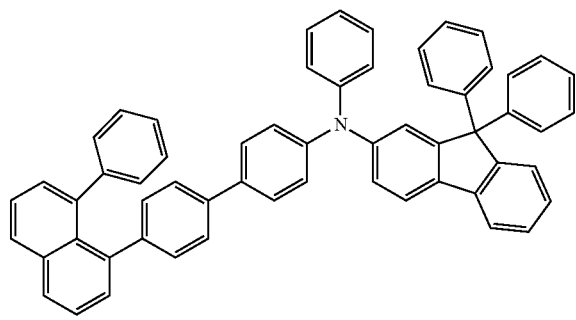
96
The amine compound represented by Formula 1 may be any one selected from the group of compounds represented in the following Compound Group 3.
[Compound Group 3]
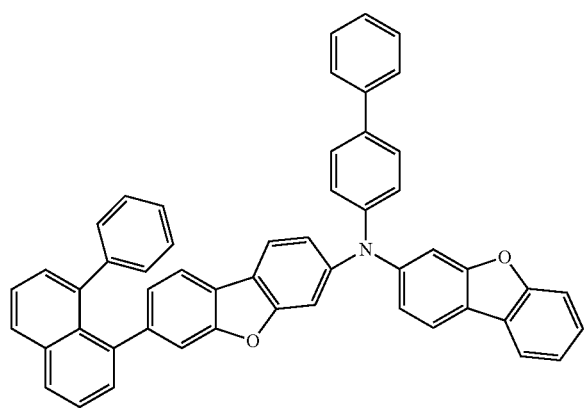
97
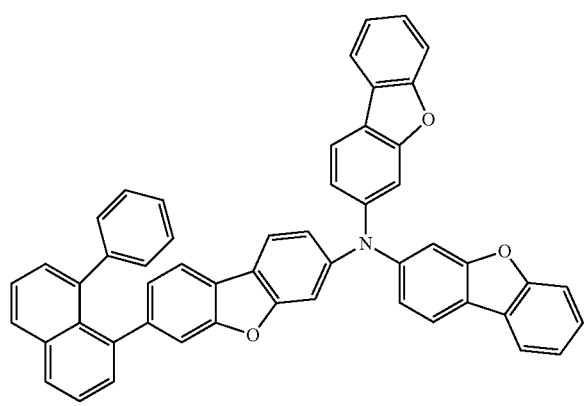
98
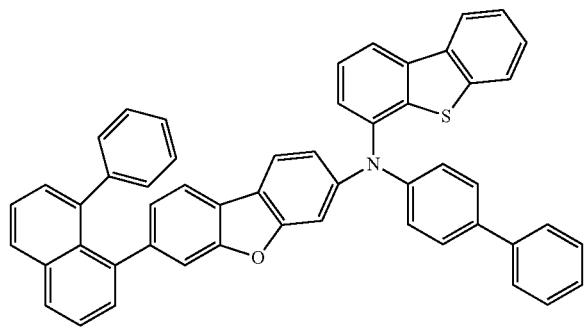
99
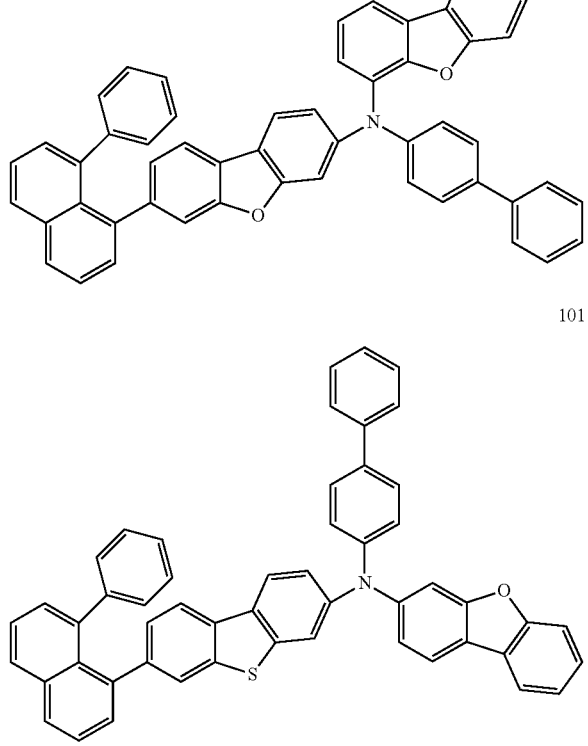
100
101
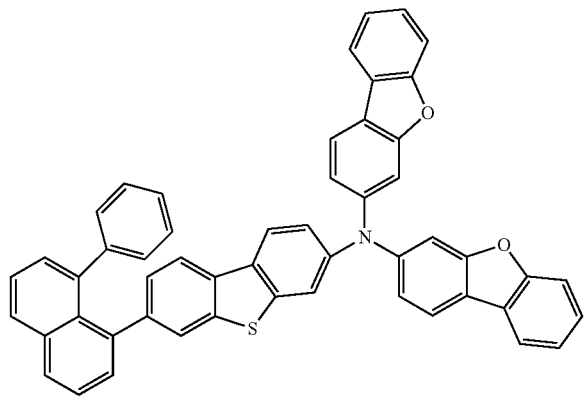
102

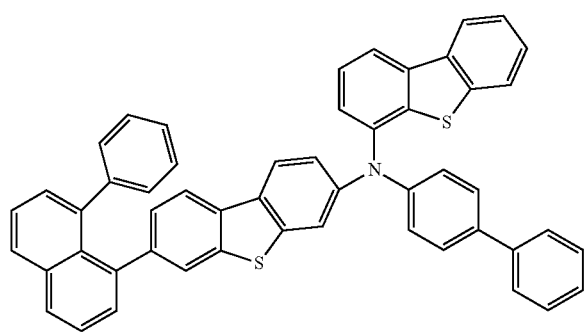
103
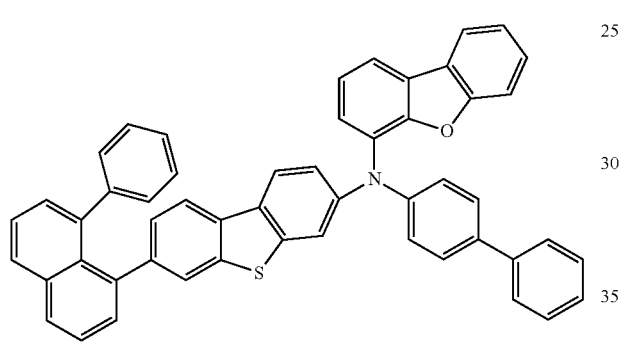
104
The amine compound represented by Formula 1 may be any one selected from the group of compounds represented in the following Compound Group 4.
[Compound Group 4]
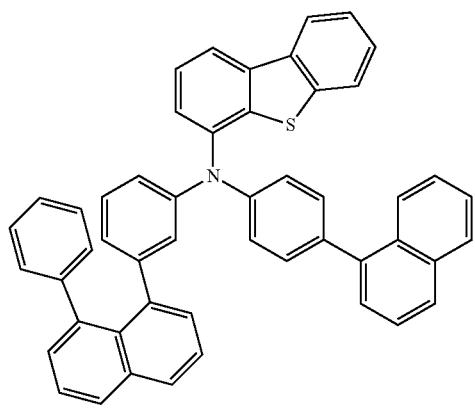
105
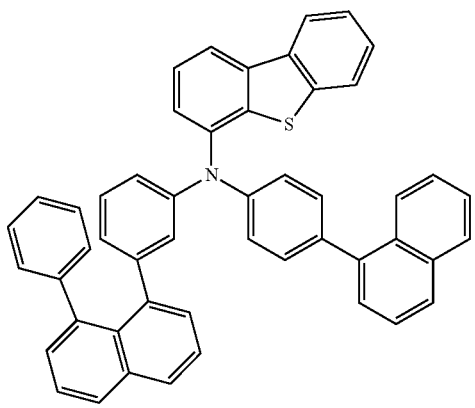
106
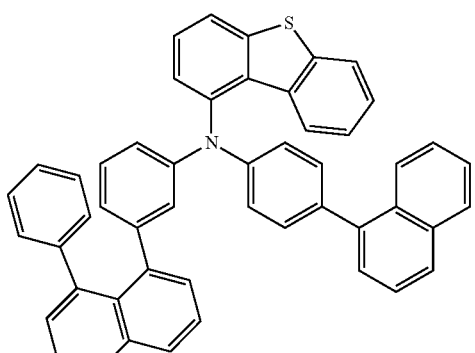
107
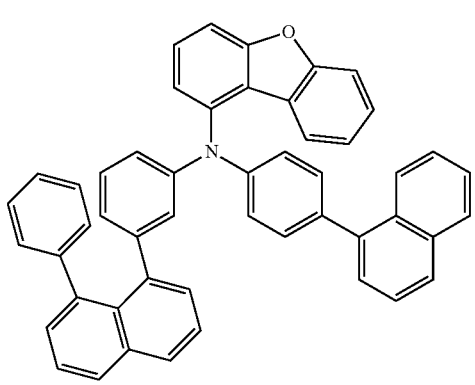
108
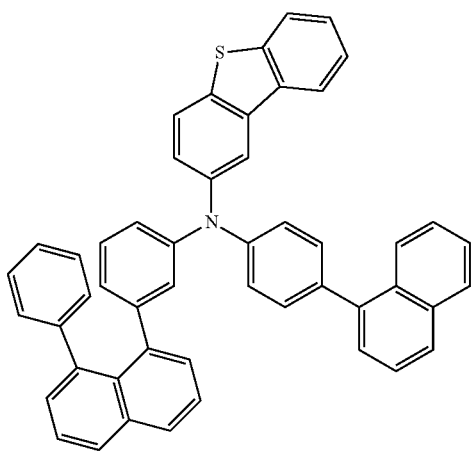
109

-continued
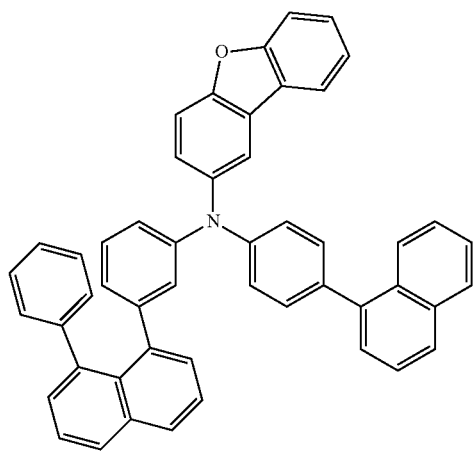
110
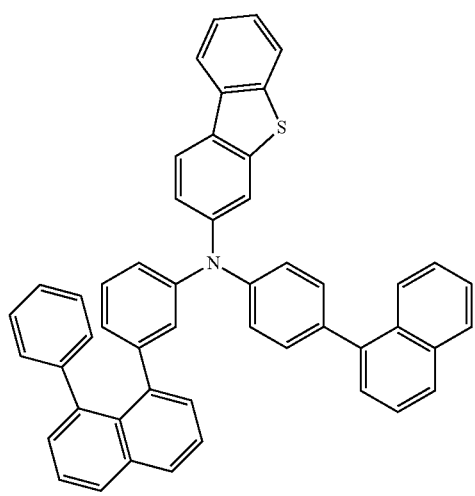
111
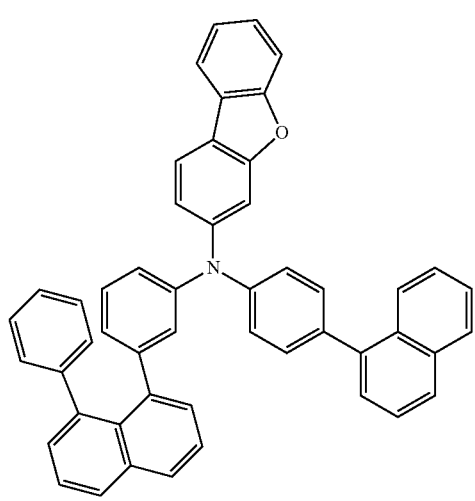
112
-continued
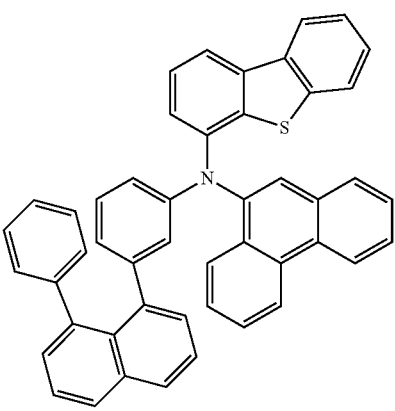
113
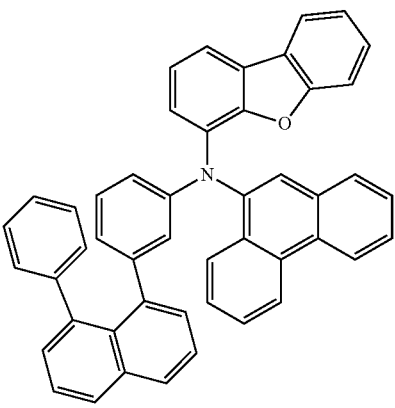
114
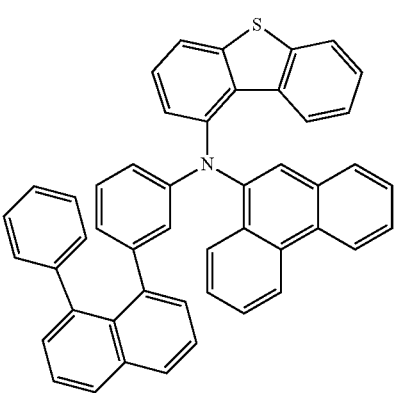
115
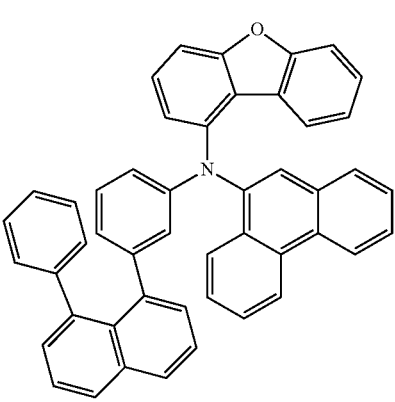
116

117
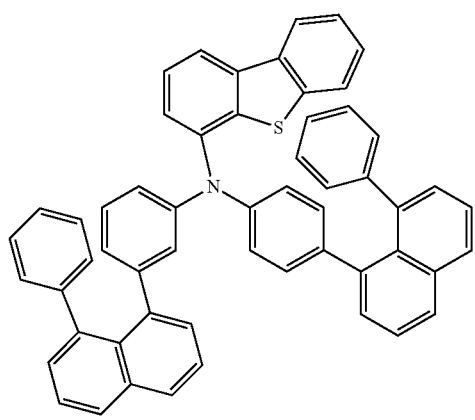
118
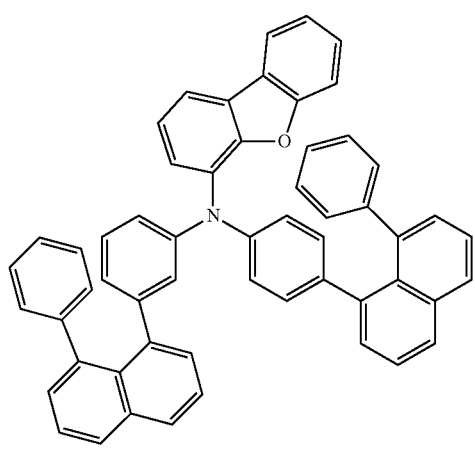
119
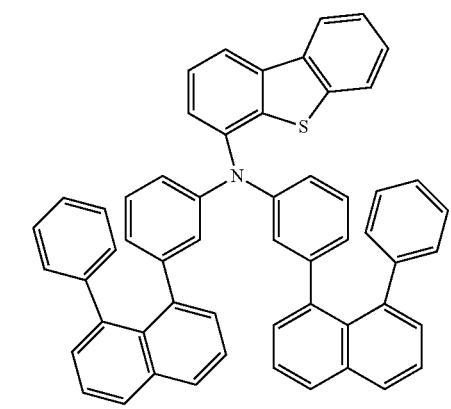
120
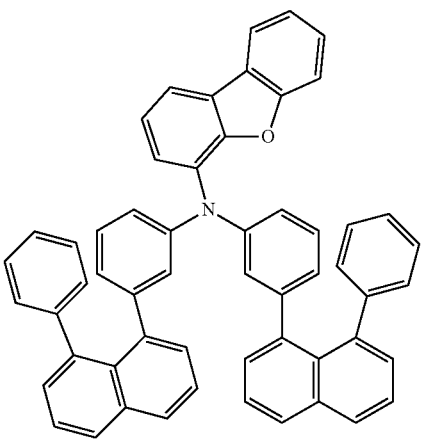
121
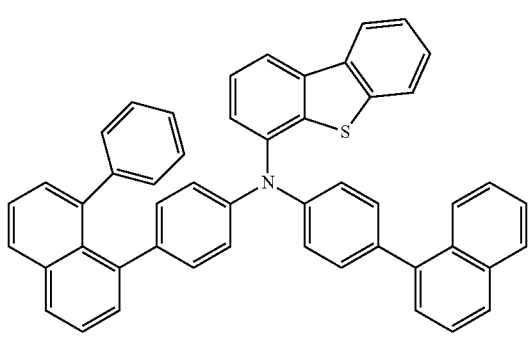
122
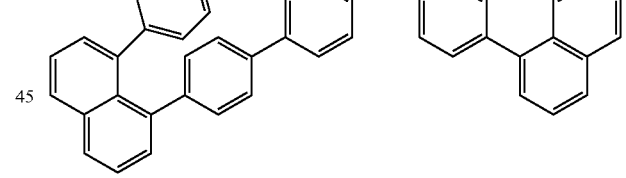
123
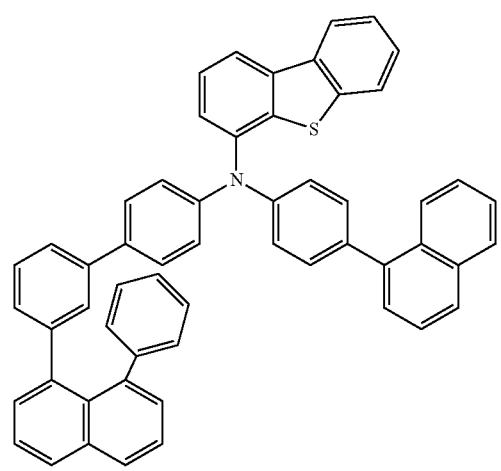

124
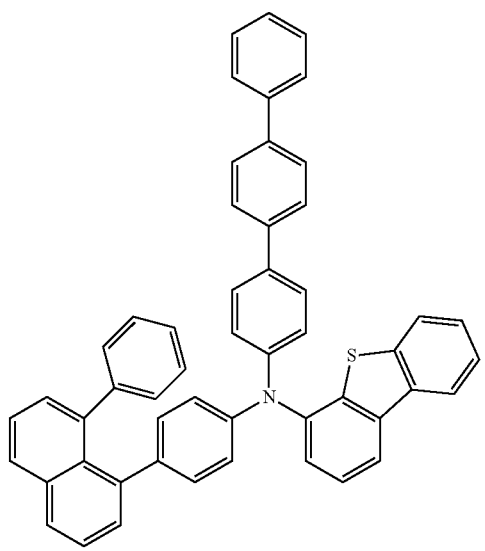
125
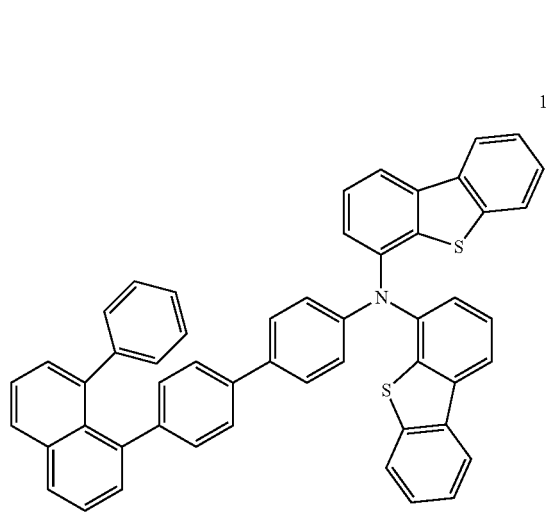
127
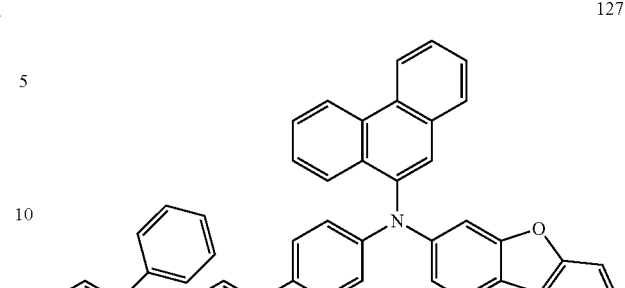
128
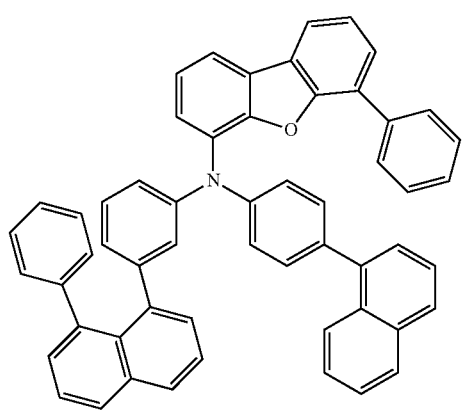
126
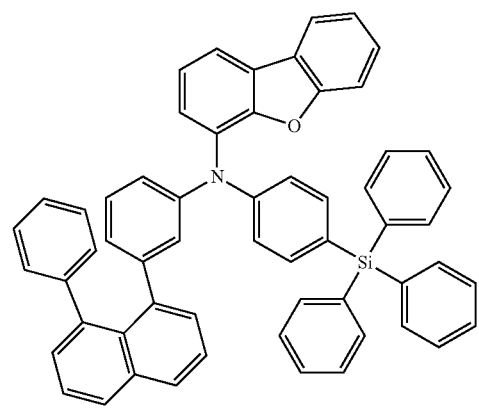
129
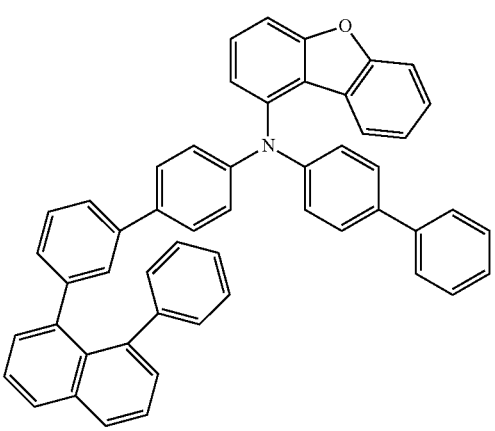

The amine compound represented by Formula 1 may be any one selected from the group of compounds represented in the following Compound Group 5.
[Compound Grouup 5]
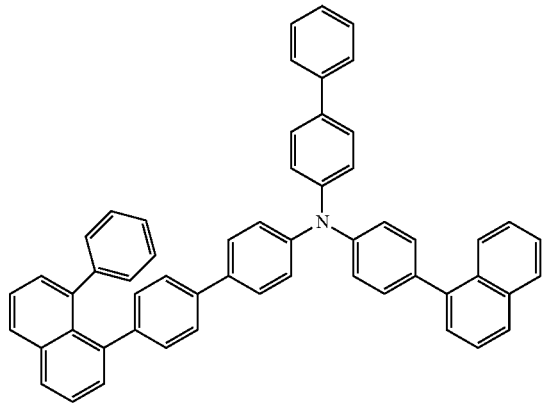
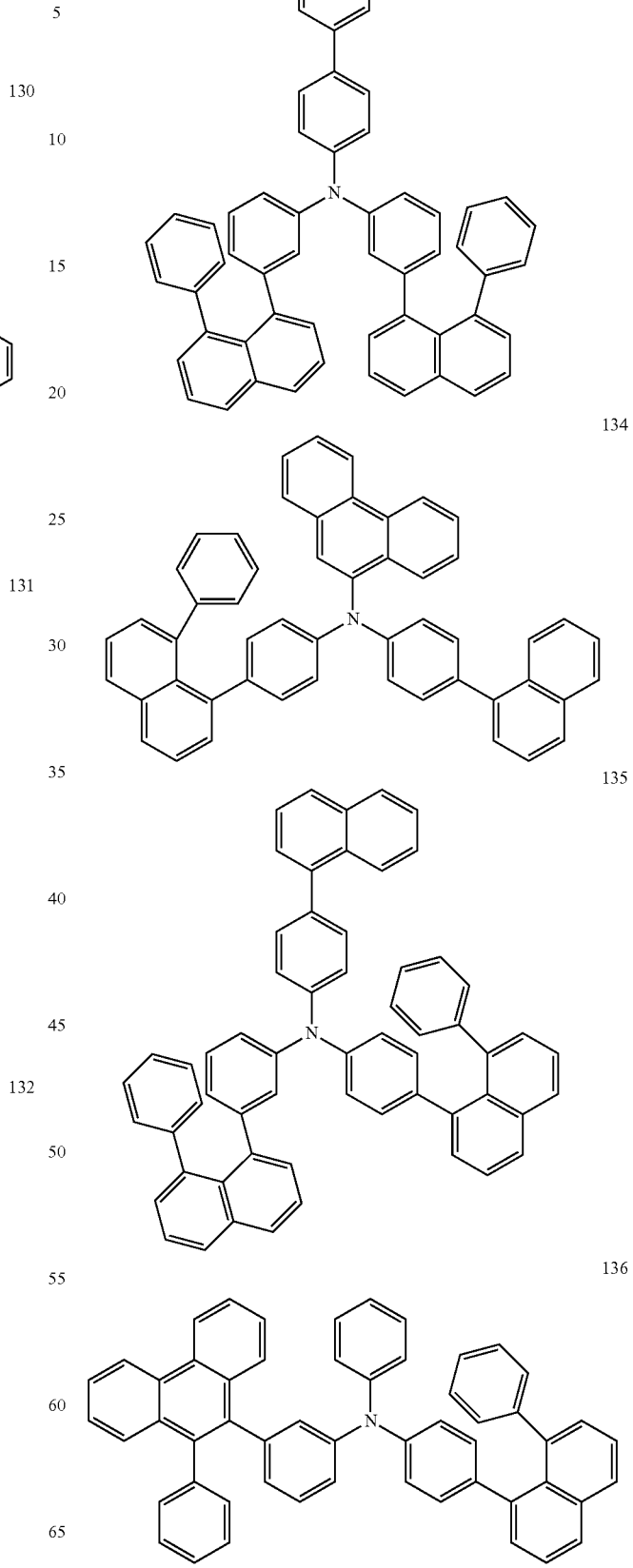

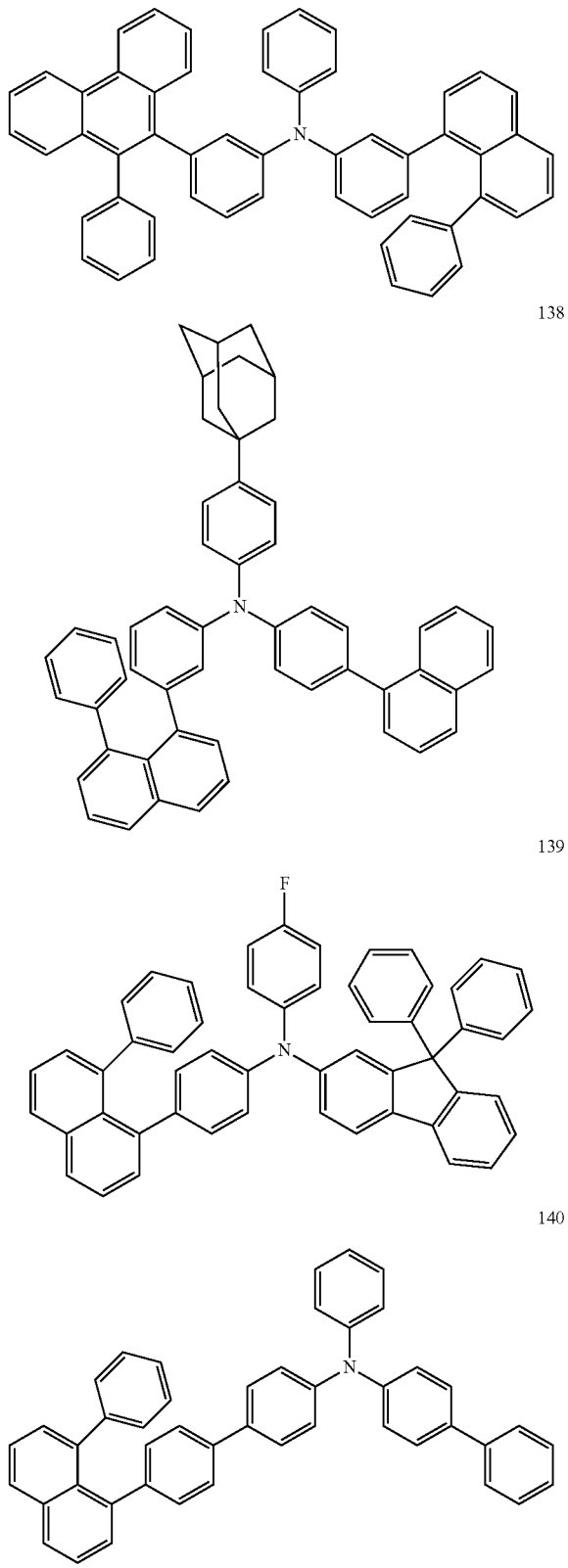

The amine compound according to an embodiment includes a naphthyl group in which hydrogen atoms at positions 1 and 8 are substituted. When the amine compound represented by Formula 1 is applied to an organic electroluminescence device, high emission efficiency, a low driving voltage and long life may be secured. When the amine compound includes a naphthyl group in which hydrogen atoms at positions 1 and 8 are substituted, hole transport properties may be maintained and thermal and charge tolerance may be improved. The deterioration of properties due to high temperature heat and charge may be decreased, and an organic electroluminescence device to which the amine compound is applied may attain long life. In addition, when the crystallization of the amine compound according to an embodiment is restrained due to the large volume of the substituted naphthyl group, layer quality may be improved, and an organic electroluminescence device with high efficiency may be attained by applying thereof.

Hereinafter, an organic electroluminescence device according to an embodiment will be explained. The explanation will be mainly given with regard to features other than the amine compound according to an embodiment, and parts that are unexplained will conform to the above-description or the amine compound.

An organic electroluminescence device according to an embodiment includes the amine compound according to an embodiment.

Figure 2:
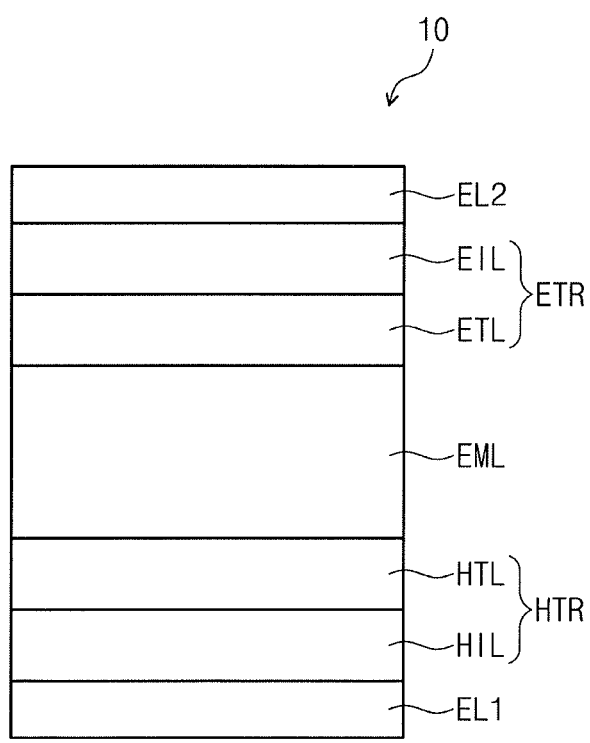
FIG. 2 illustrates a schematic cross-sectional view of an organic electroluminescence device according to an embodiment.
Figure 3:
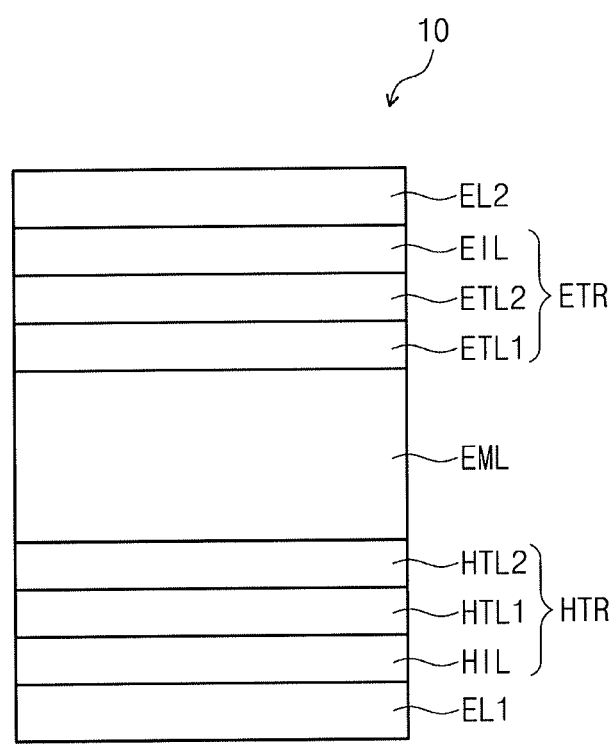
FIG. 3 illustrates a schematic cross-sectional view of an organic electroluminescence device according to an embodiment.

FIG. 1 illustrates a schematic cross-sectional view of an organic electroluminescence device according to an embodiment. FIG. 2 illustrates a schematic cross-sectional view of an organic electroluminescence device according to an embodiment. FIG. 3 illustrates a schematic cross-sectional view of an organic electroluminescence device according to an embodiment.

Referring to FIGS. 1 to 3, an organic electroluminescence device 10 according to an embodiment includes a first electrode EL1, a hole transport region HTR, an emission layer EML, an electron transport region ETR, and a second electrode EL2.

The first electrode EL1 has conductivity. The first electrode EL1 may be a pixel electrode or an anode. The first electrode EL1 may be a transmissive electrode, a transflective electrode, or a reflective electrode. In the case where the first electrode EL1 is a transmissive electrode, the first electrode EL1 may be formed using a transparent metal oxide such as indium tin oxide (ITO), indium zinc oxide (IZO), zinc oxide (ZnO), or indium tin zinc oxide (ITZO). In the case where the first electrode EL1 is a transflective electrode or reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). In some implementations, the first electrode EL1 may have a structure including a plurality of layers including a reflective layer or transflective layer formed using the above materials, and a transparent layer formed using ITO, IZO, ZnO, or ITZO.

Hereinafter, an example where the amine compound according to an embodiment is included in a hole transport region HTR, will be explained. The amine compound according to an embodiment may be included in at least one organic layer provided between the first electrode EL1 and the second electrode EL2. For example, the amine compound according to an embodiment may be included in the emission layer EML.

The organic electroluminescence device according to an embodiment may include the amine compound in a hole transport region HTR. The organic electroluminescence device according to an embodiment may include the amine compound represented by Formula 1 in a hole transport region HTR.

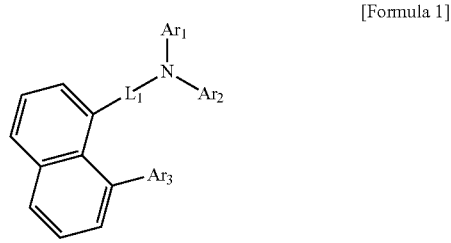

[Formula 1]

In Formula 1, particular explanation of $Ar^1$, $Ar^2$, $Ar^3$, and $L^1$ is the same as described above, and will not be repeated.

Particular explanation regarding the amine compound represented by Formula 1 may refer to the above description and will not be repeated.

The hole transport region HTR may be disposed on the first electrode EL1. The hole transport region HTR may include at least one of a hole injection layer HIL, a hole transport layer HTL, a hole buffer layer, or an electron blocking layer.

The hole transport region HTR may have a single layer formed using a single material, a single layer formed using a plurality of different materials, or a multilayer structure including a plurality of layers formed using a plurality of different materials.

For example, the hole transport region HTR may have a single layer structure of a hole injection layer HIL or a hole transport layer HTL, or may have a single layer structure formed using a hole injection material and a hole transport material. In addition, the hole transport region HTR may have a single layer structure formed using a plurality of different materials, or a structure laminated in order from the first electrode EL1 to include hole injection layer HIL/hole transport layer HTL (as shown in FIG. 2), hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer, as examples.

As shown in FIG. 3, the hole transport region HTR may include a plurality of hole transport layers. The hole transport region HTR may include a first hole transport layer HTL1 and a second hole transport layer HTL2 disposed on the first hole transport layer HTL1. The second hole transport layer HTL2 may be a hole transport layer adjacent to the emission layer EML, out of the plurality of the hole transport layers.

The hole transport region HTR may be formed using a suitable method such as a vacuum deposition method, a spin coating method, a cast method, a Langmuir-Blodgett (LB) method, an inkjet printing method, a laser printing method, and a laser induced thermal imaging (LITI) method.

The hole transport region HTR may include the amine compound according to an embodiment. The hole transport region HTR may include the amine compound as a hole transport material. The layer including the amine compound may be a hole transport layer HTL. As shown in FIG. 3, when the hole transport layer includes the first hole transport layer HTL1 and the second hole transport layer HTL2, the amine compound may be included in the second hole transport layer HTL2. The amine compound may be included in a layer adjacent to the emission layer EML in the hole transport layer HTR.

In the case where the hole transport layer HTL includes the amine compound, the hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4''-tris(3-methylphenylphenylamino)triphenylamine (m-MTDATA), 4,4',4''-tris(N,N-diphenylamino)triphenylamine (TDATA), 4,4',4''-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, 1,4,5,8,9,11-hexaazatriphenylenehexacarbonitrile (HAT-CN), etc.

The hole transport layer HTL may further include a suitable material in addition to the amine compound. The hole transport layer HTL may include, for example, a carbazole derivative such as N-phenyl carbazole, and polyvinyl carbazole, a fluorine-based derivative, N,N'-bis(3-methylphenyl)-N,N'-diphenyl-[1,1-biphenyl]-4,4'-diamine (TPD), a triphenylamine-based derivative such as 4,4',4''-tris(N-carbazolyl)triphenylamine (TCTA), N,N'-di(1-naphthyl)-N,N'-diphenylbenzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), etc.

The thickness of the hole transport region HTR may be from about 150 Å to about 12,000 Å, for, for example, from about 150 Å to about 1,500 Å. In the case where the hole transport region HTR includes both the hole injection layer HIL and the hole transport layer HTL, the thickness of the hole injection layer HIL may be from about 100 Å to about 10,000 Å, or, for example, from about 100 Å to about 1,000 Å, and the thickness of the hole transport layer HTL may be from about 50 Å to about 1,000 Å. In the case where the thicknesses of the hole transport region HTR, the hole injection layer HIL, and the hole transport layer HTL satisfy the above-described ranges, satisfactory hole transport properties may be obtained without the substantial increase of a driving voltage.

The hole transport region HTR may further include a charge generating material in addition to the above-described materials to improve conductivity. The charge generating material may be dispersed in the hole transport region HTR uniformly or non-uniformly. The charge generating material may be, for example, a p-dopant. The p-dopant may be one of a quinone derivative, a metal oxide, or a cyano group-containing compound, as examples. Examples of the p-dopant may include a quinone derivative such as tetracyanoquinodimethane (TCNQ), and 2,3,5,6-tetrafluoro-tetracyanoquinodimethane (F4-TCNQ), or a metal oxide such as tungsten oxide, and molybdenum oxide, as examples.

As described above, the hole transport region HTR may further include at least one of a hole buffer layer and an electron blocking layer in addition to the hole injection layer HIL and the hole transport layer HTL. The hole buffer layer may compensate an optical resonance distance according to the wavelength of light emitted from the emission layer EML and may increase light emission efficiency. Materials included in the hole transport region HTR may be used as materials included in the hole buffer layer. The electron blocking layer is a layer preventing electron injection from the electron transport region ETR into the hole transport region HTR.

The emission layer EML may be disposed on the hole transport region HTR. The emission layer EML may be disposed on the hole transport layer HTL so as to contact the hole transport layer HTL. The thickness of the emission layer EML may be, for example, from about 100 Å to about 600 Å. The emission layer EML may be in a form of a single layer formed using a single material, a single layer formed using a plurality of different materials, or a multilayer structure having a plurality of layers formed using a plurality of different materials.

The emission layer EML may emit one of red light, green light, blue light, white light, yellow light, and cyan light. The emission layer EML may include a fluorescent material or a phosphorescent material. The emission layer EML may include a host and a dopant.

The host material of the emission layer EML may be selected from an anthracene derivative, a fluoranthene derivative, a pyrene derivative, an arylacetylene derivative, a fluorene derivative, a perylene derivative, a chrysene derivative, a phenanthrene derivative, or the like For example, the host material may be selected from a pyrene derivative, a perylene derivative, a chrysene derivative, a phenanthrene derivative, or an anthracene derivative. For example, as the host material of the emission layer EML, an anthracene derivative represented by Formula 4 may be used.

[Formula 4]

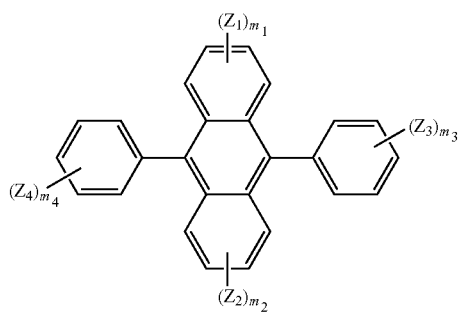

In Formula 4, $Z_1$ to $Z_4$ are each independently a hydrogen atom, a deuterium atom, a halogen atom, a substituted or unsubstituted silyl group, a substituted or unsubstituted alkyl group having 1 to 15 carbon atoms, a substituted or unsubstituted aryl group having 6 to 30 ring carbon atoms, or a substituted or unsubstituted heteroaryl group having 2 to 30 ring carbon atoms, $m_1$ and $m_2$ are each independently an integer of 0 to 4, $m_3$ and $m_4$ are each independently an integer of 0 to 5. In Formula 4, $Z_3$ and $Z_4$ may be each independently combined with an adjacent group to form a ring.

The compound represented by Formula 4 may include, for example, one of the compounds represented by the following structures.

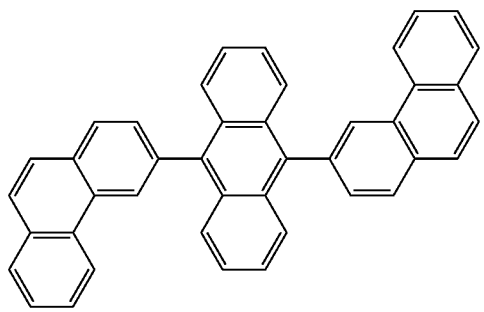

a-1

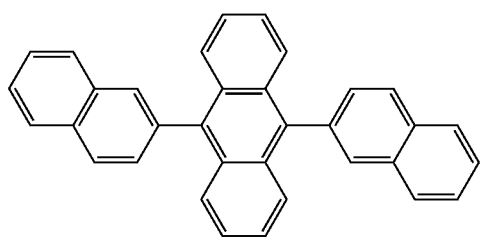

a-2

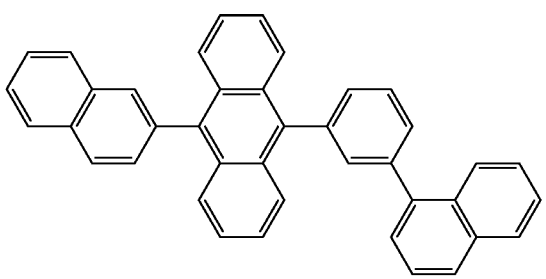

a-3

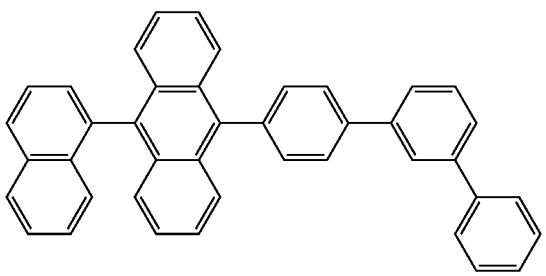

a-4

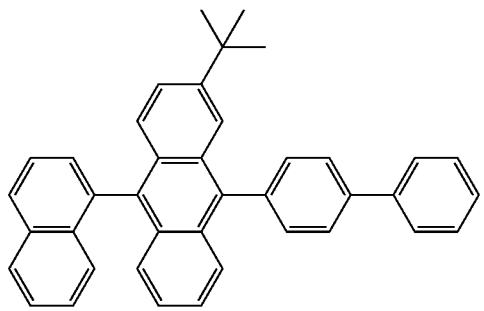

a-5 a-6
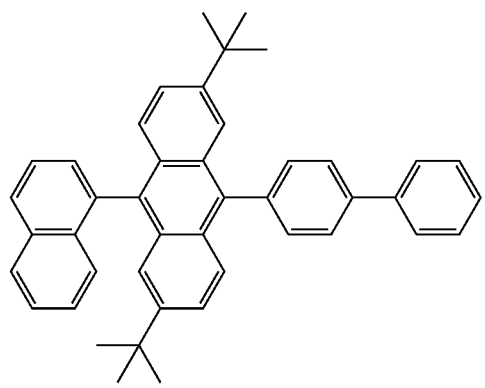

a-7
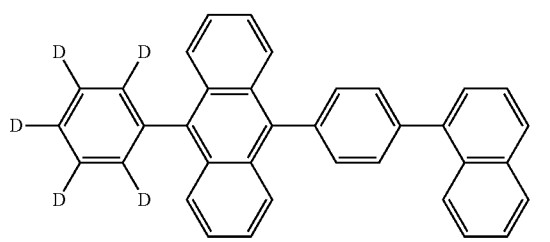

a-8
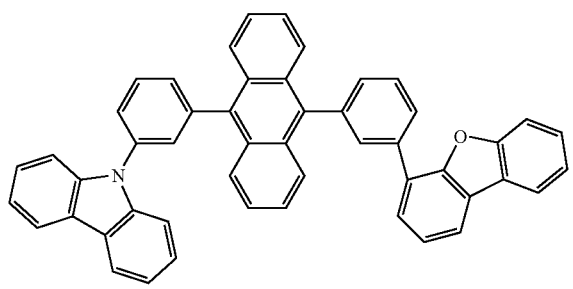

a-9
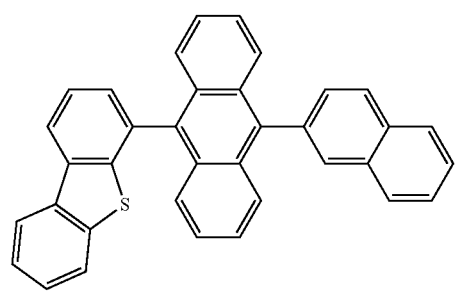

a-10
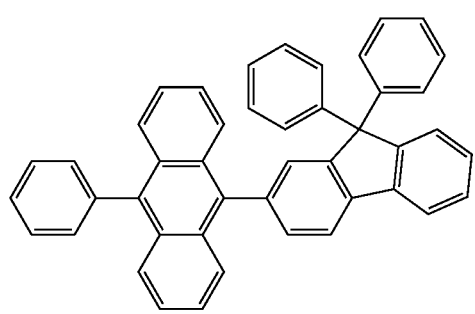

a-11
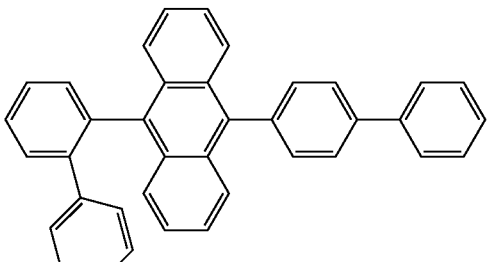

a-12
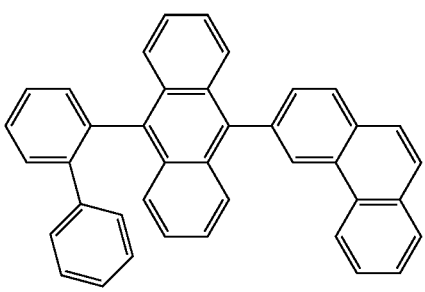

The host may be a suitable host material such as, for example, tris(8-hydroxyquinolino)aluminum (Alq3), 4,4'-bis(N-carbazolyl)-1,1'-biphenyl (CBP), poly(N-vinylcarbazole) (PVK), 9,10-di(naphthalene-2-yl)anthracene (ADN), 4,4',4''-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), etc.

The dopant may include, for example, a styryl derivative (for example, 1,4-bis[2-(3-N-ethylcarbazolyl)vinyl]benzene (BCzVB), 4-(di-p-tolylamino)-4'-[(di-p-tolylamino)styryl] stilbene (DPAVB), N-(4-((E)-2-(6-((E)-4-(diphenylamino) styryl)naphthalen-2-yl)vinyl)phenyl)-N-phenylbenzenamine (N-BDAVBi)), perylene or a derivative thereof (for example, 2,5,8,11-tetra-tert-butylperylene (TBP)), pyrene or a derivative thereof (for example, 1,1-dipyrene, 1,4-dipyrenylbenzene, 1,4-bis(N,N-diphenylamino)pyrene), etc.

When the emission layer EML emits red light, the emission layer EML may include, for example, tris(dibenzoylmethanato)phenanthroline europium (PBD:Eu(DBM)3 (Phen)), or a fluorescent material including perylene. In the case where the emission layer EML emits red light, the dopant included in the emission layer EML may be selected from a metal complex or an organometallic complex such as bis(1-phenylisoquinoline)acetylacetonate iridium (PIQIr(acac)), bis(1-phenylquinoline)acetylacetonate iridium (PQIr (acac), tris(1-phenylquinoline)iridium (PQr), and octaethylporphyrin platinum (PtOEP), rubrene and a derivative thereof, 4-dicyanomethylene-2-(p-dimethylaminostyryl)-6-methyl-4H-pyran (DCM), or a derivative thereof.

In the case where the emission layer EML emits green light, the emission layer EML may further include a fluorescent material including, for example, tris(8-hydroxyquinolino)aluminum (Alq3). In the case where the emission layer EML emits green light, the dopant included in the emission layer EML may be selected from a metal complex or organometallic complex such as fac-tris(2-phenylpyridine)iridium (Ir(ppy)3), coumarin, or a derivative thereof.

In the case where the emission layer EML emits blue light, the emission layer EML may further include a fluorescent material including at least one selected from, for example, spiro-DPVBi, spiro-6P, distyryl-benzene (DSB), distyryl-arylene (DSA), a polyfluorene (PFO)-based polymer, and a poly(p-phenylene vinylene) (PPV)-based polymer. In the case where the emission layer EML emits blue light, the dopant included in the emission layer EML may be selected from a metal complex or an organometallic complexes such as (4,6-F2ppy)$_2$Irpic, perylene, or a derivative thereof.

The electron transport region ETR may be provided on the emission layer EML. The electron transport region ETR may include at least one of an electron blocking layer, an electron transport layer ETL or an electron injection layer EIL, as examples.

The electron transport region ETR may be in a form of a single layer formed using a single material, a single layer formed using a plurality of different materials, or a multi-layer structure having a plurality of layers formed using a plurality of different materials.

For example, the electron transport region ETR may have a single layer structure including the electron injection layer EIL or the electron transport layer ETL, or a single layer structure formed using an electron injection material and an electron transport material. In some implementations, the electron transport region ETR may have a single layer structure having a plurality of different materials, or a structure laminated in order from the first electrode EL1 to include electron transport layer ETL/electron injection layer EIL(as shown in FIG. 2), or hole blocking layer/electron transport layer ETL/electron injection layer EIL, as examples.

As shown in FIG. 3, the electron transport region ETR may include a plurality of electron transport layers. For example, the electron transport region ETR may include a first electron transport layer ETL and a second electron transport layer ETL2 disposed on the first electron transport layer ETL1.

The electron transport region ETR may be formed using a suitable method such as a vacuum deposition method, a spin coating method, a cast method, a Langmuir-Blodgett (LB) method, an inkjet printing method, a laser printing method, or a laser induced thermal imaging (LITI) method.

In the case where the electron transport region ETR includes the electron transport layer ETL, the electron transport region ETR may include tris(8-hydroxyquinolinato)aluminum (Alq3), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,08)-(1,1'-biphenyl-4-olato) aluminum (BAlq), beryllium bis(benzoquinolin-10-olate (Bebq$_2$), 9,10-di(naphthalene-2-yl)anthracene (ADN), or a mixture thereof, as examples. The thickness of the electron transport layer ETL may be from about 100 Å to about 1,000 Å, or, for example, from about 150 Å to about 500 Å. If the thickness of the electron transport layer ETL satisfies the above-described range, satisfactory electron transport property may be obtained without a substantial increase of a driving voltage.

When the electron transport region ETR includes the electron injection layer EIL, the electron injection layer EIL may include a metal such as Al, Ag, Li, Mg and Ca, or a mixture thereof. For example, the electron injection layer EIL may include LiF, lithium quinolate (Liq), Li$_2$O, BaO, NaCl, CsF, a lanthanide series metal such as Yb, or a metal halide such as RbCl and RbI. In some implementations, the electron injection layer EIL may be formed using a mixture of an electron transport material and an insulating organo metal salt. The organo metal salt may be a material having an energy band gap of about 4 eV or more. For example, the organo metal salt may include a metal acetate, a metal benzoate, a metal acetoacetate, a metal acetylacetonate, or a metal stearate. The thickness of the electron injection layer EIL may be from about 10 Å to about 100 Å. When the thickness of the electron injection layer EIL satisfies the above described range, satisfactory electron injection properties may be obtained without inducing the substantial increase of a driving voltage.

The electron transport region ETR may include a hole blocking layer as described above. The hole blocking layer may include, for example, at least one of 2,9-dimethyl-4,7-diphenyl-1,10-phenanthroline (BCP) and 4,7-diphenyl-1,10-phenanthroline (Bphen).

The second electrode EL2 may be disposed on the electron transport region ETR. The second electrode EL2 may be a common electrode or a cathode. The second electrode EL2 may be a transmissive electrode, a transflective electrode or a reflective electrode. In the case where the second electrode EL2 is a transmissive electrode, the second electrode EL2 may be formed using a transparent metal oxide, for example, ITO, IZO, ZnO, ITZO, etc.

In the case where the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer or a transflective layer formed using the above-described materials and a transparent conductive layer formed using ITO, IZO, ZnO, ITZO, etc.

The second electrode EL2 may be connected with an auxiliary electrode. In the case where the second electrode EL2 is connected with the auxiliary electrode, the resistance of the second electrode EL2 may decrease.

In the organic electroluminescence device 10, according to the application of a voltage to each of the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to generate excitons, and light may be emitted via the transition of the excitons from an excited state to a ground state.

In the case where the organic electroluminescence device 10 is a top emission type, the first electrode EL1 may be a reflective electrode, and the second electrode EL2 may be a transmissive electrode or a transflective electrode. In the case where the organic electroluminescence device 10 is a bottom emission type, the first electrode EL1 may be a transmissive electrode or a transflective electrode, and the second electrode EL2 may be a reflective electrode.

The organic electroluminescence device according to an embodiment includes the amine compound represented by Formula 1. Thereby, high emission efficiency, a low driving voltage and long life may be secured. The amine compound according to an embodiment may be disposed in the hole transport region HTR of the organic electroluminescence device. Thereby, high hole transport properties and decreased thermal and charge load may be attained, and high emission efficiency, a low driving voltage and long life may be secured. For example, when the amine compound represented by Formula 1 includes a naphthyl group in which hydrogen atoms at positions 1 and 8 are substituted, the deterioration of properties due to high temperature heat and charge may be decreased. Accordingly hole transport properties may be maintained and thermal and charge tolerance may be improved, and an organic electroluminescence device to which the amine compound is applied may attain long life. In addition, the crystallization of the amine compound according to an embodiment may be restrained due to the large volume of the substituted naphthyl group. Accordingly, layer quality may be improved, and an organic electroluminescence device with high efficiency may be attained.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Synthetic Examples

1. Synthesis of Compound 5

(Synthesis of Compound A)

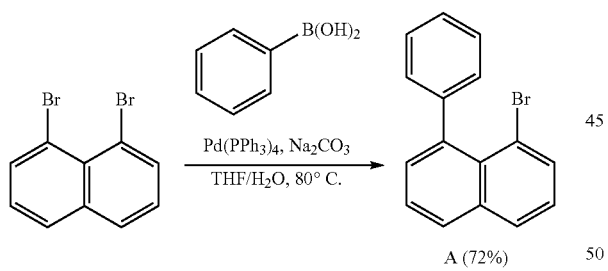

Under an argon (Ar) atmosphere, 8.80 g of 1,8-dibromonaphthalene, 4.69 g of phenylboronic acid, 4.89 g of Na$_2$CO$_3$, and 200 ml of a mixed solution of THF/water (20%) containing 1.07 g of Pd(PPh$_3$)$_4$ dissolved therein were injected to a 500 ml three neck flask and were heated and stirred at about 80° C. for about 5 hours. After cooling in air, dichloromethane was added, an organic layer was separated and taken, and solvents were evaporated. The crude product thus obtained was separated by silica gel column chromatography (hexane/toluene) to obtain 6.27 g (yield 72%) of Compound A as a pale yellow solid. The molecular weight of Compound A measured by FAB-MS was 283.

(Synthesis of Compound B)

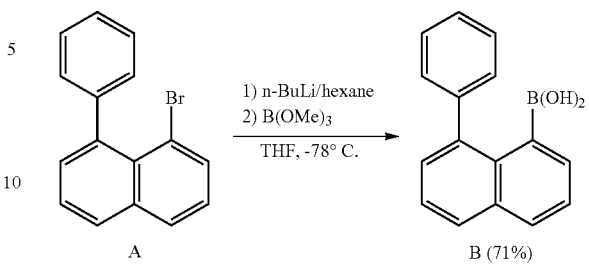

Under an argon (Ar) atmosphere, 6.70 g of Compound A, and 60 ml of a THF solvent were added to a 200 ml three neck flask, and cooled to about −78° C. Then, 23.1 ml of a hexane solution of n-BuLi (1.6 M) was added thereto dropwisely, followed by stirring for about 50 minutes. After that, 5 ml of a THF solution with 13.4 g of B(OMe)$_3$ dissolved therein was added dropwisely, followed by stirring at about −78° C. for about 50 minutes. The temperature was elevated again to room temperature, and the stirring was conducted for about 3 hours. Then, a saturated NH$_4$Cl aqueous solution was added thereto, an organic layer was separated and taken, and solvents were evaporated. The residues obtained in the three-necked flask were washed with hexane to obtain 4.17 g (yield 71%) of Compound B as a white solid. The molecular weight of Compound B measured by FAB-MS was 248.

(Synthesis of Compound C)

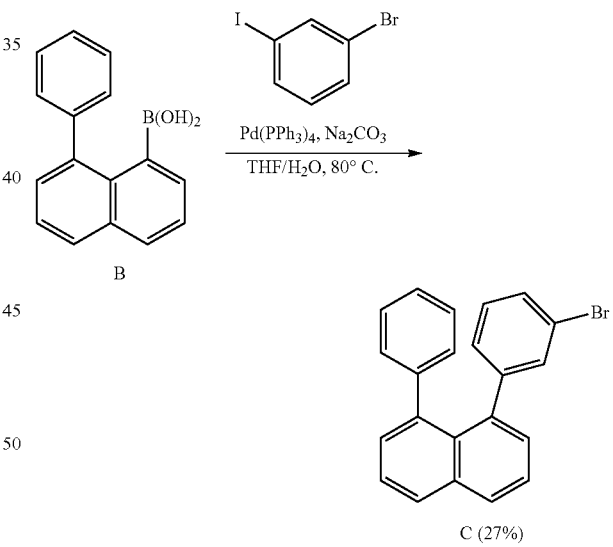

Under an argon (Ar) atmosphere, 5.70 g of Compound B, 8.13 g of 1-bromo-3-iodobenzene, 3.65 g of Na$_2$CO$_3$, and 130 ml of a mixed solution of THF/water (20%) with 0.797 g of Pd(PPh$_3$)$_4$ dissolved therein were injected to a 500 ml three neck flask and were heated and stirred at about 80° C. for about 5 hours. After cooling in the air, dichloromethane was added, an organic layer was separated and taken, and solvents were evaporated. The crude product thus obtained was separated by silica gel column chromatography (hexane/toluene) to obtain 2.22 g (yield 27%) of Compound C as a pale yellow solid. The molecular weight of Compound C measured by FAB-MS was 359.

(Synthesis of Compound 5)

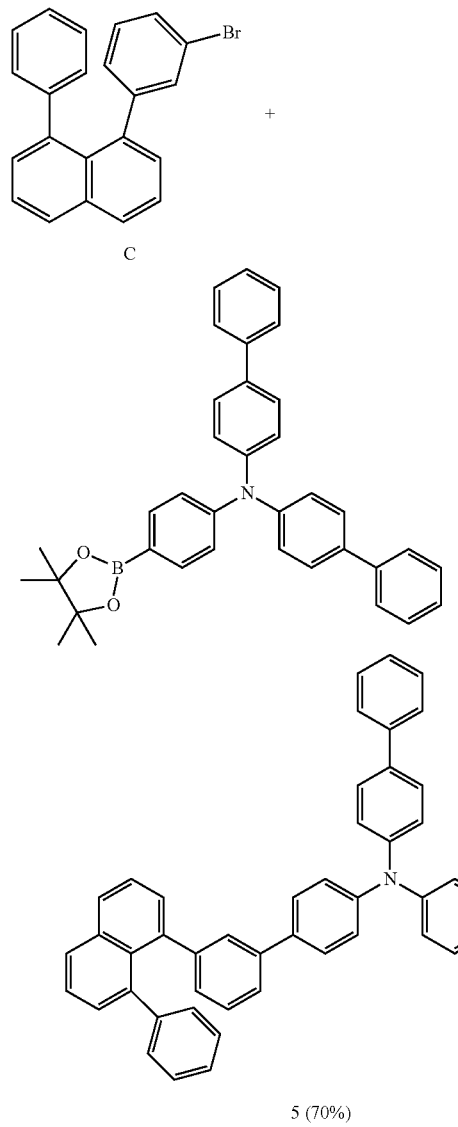

5 (70%)

2. Synthesis of Compound 21

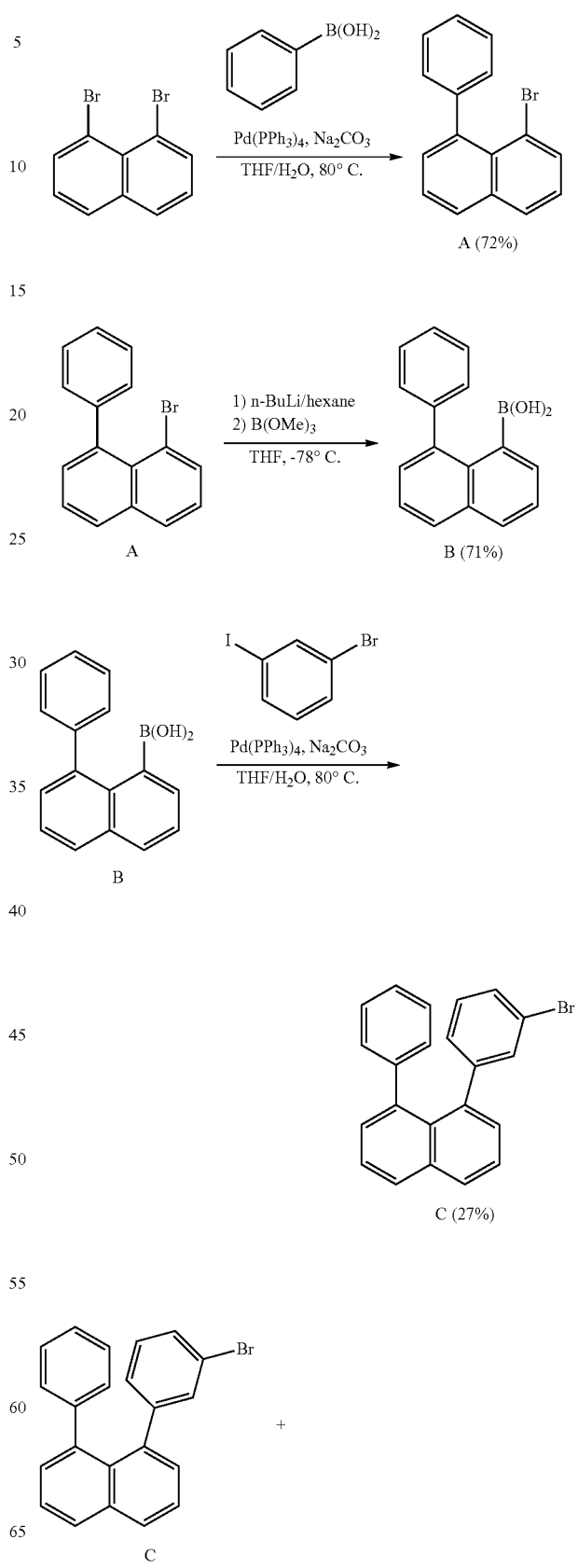

Under an argon (Ar) atmosphere, 6.17 g of Compound C, 3.85 g of N-[1,1"-biphenyl]-4-yl-N-[4-(4,4,5,5-tetramethyl-1,3,2-dioxaborolan-2-yl)phenyl]-[1,1-biphenyl]-4-amine, 1.84 g of $K_3PO_4$, and 130 ml of a mixed solution of THF/water (20%) with 0.231 g of $Pd(PPh_3)_4$ dissolved therein were injected to a 300 ml three neck flask and were heated and stirred at about 80° C. for about 5 hours. Dichloromethane was added, an organic layer was separated and taken, and solvents were evaporated. The crude product thus obtained was separated by silica gel column chromatography (hexane/toluene) to obtain 3.16 g (yield 70%) of Compound 5 as a white solid. The molecular weight of the compound measured by FAB-MS was 676. The chemical shift values of the compound measured by $^1$H-NMR (CDCl$_3$) were 8.52-8.39 (m, 4H), 8.33 (d, 2H), 8.25 (dd, 4H), 8.10 (d, 2H), 8.02-7.89 (m, 4H), 7.92-7.77 (m, 8H), 7.69-7.62 (m, 4H), 7.48-7.43 (m, 3H), 7.18-7.02 (m, 6H). From the results, the white solid compound was identified as Compound 5.

3. Synthesis of Compound 46

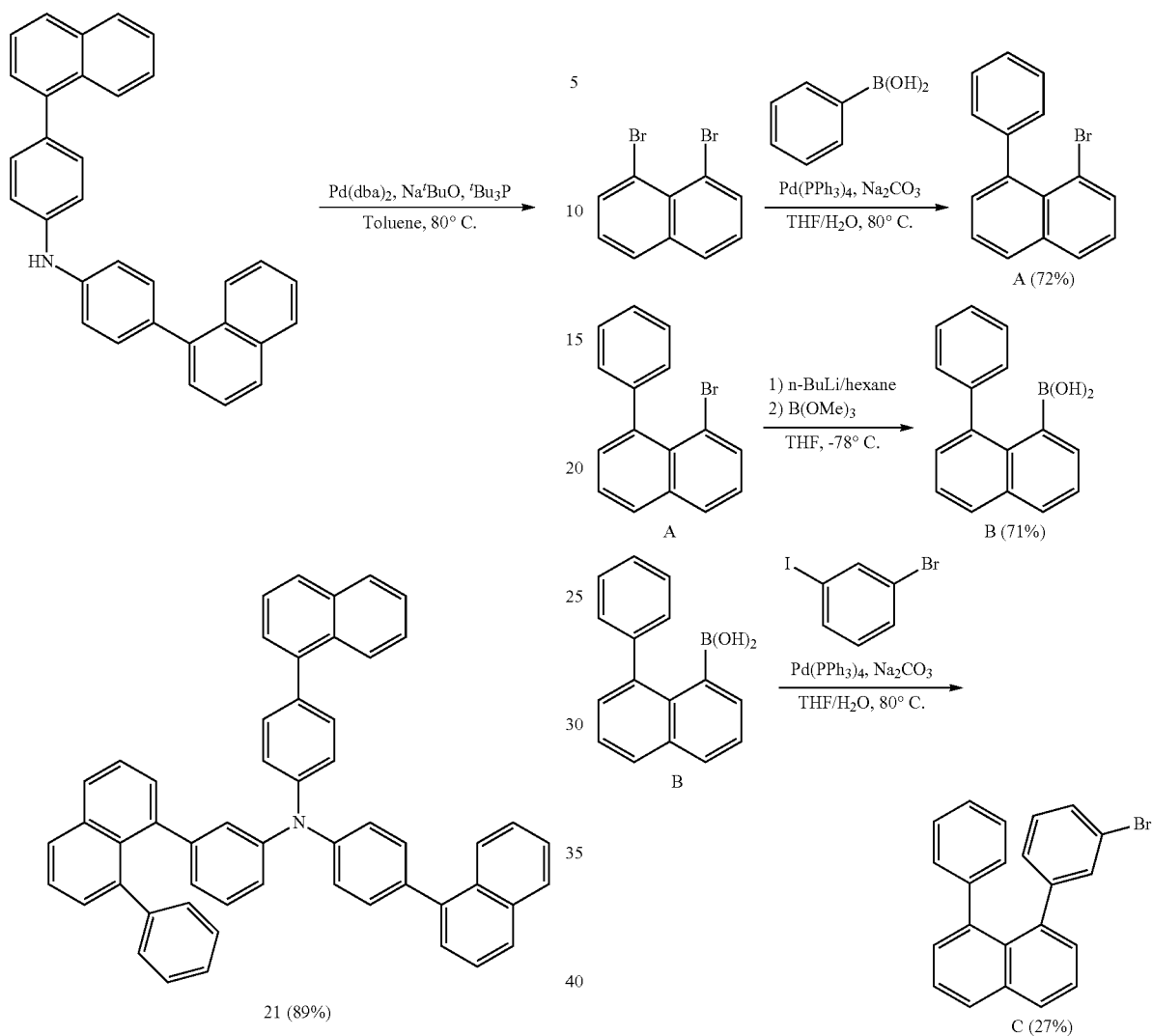

Compound C was obtained by conducting the same synthetic method of Compound C used in the synthetic method of Compound 5. Under an argon (Ar) atmosphere, 3.70 g of Compound C, 4.21 g of 4-(1-naphthalenyl)-N-[4-(1-naphthalenyl)phenyl]-benzenamine, 0.181 g of Pd(dba)$_2$, 3.69 g of NaOtBu, and 0.135 g of tBu$_3$P were added to a 300 ml two neck flask, followed by stirring and refluxing in 120 ml of a toluene mixture solvent at about 80° C. for about 6 hours. After cooling in the air, water was added, an organic layer was separated and taken, and solvents were evaporated. The crude product thus obtained was separated by silica gel column chromatography (hexane/toluene) to obtain 6.22 g (yield 89%) of Compound 21 as a white solid. The molecular weight of the compound measured by FAB-MS was 700. The chemical shift values of the compound measured by $^1$H-NMR (CDCl$_3$) were 8.52-8.39 (m, 4H), 8.33 (d, 2H), 8.25 (dd, 4H), 8.10 (d, 2H), 8.02-7.89 (m, 2H), 7.92-7.77 (m, 8H), 7.69-7.62 (m, 4H), 7.48-7.43 (m, 5H), 7.18-7.02 (m, 6H). From the results, the white solid compound was identified as Compound 21.

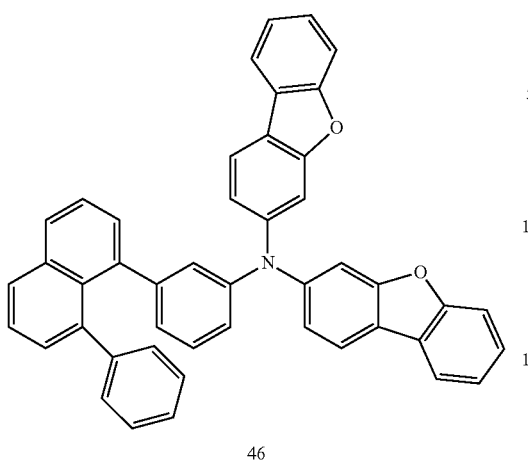

46

Compound 46 was synthesized by conducting the same synthetic method of Compound 21 except for using N-3-dibenzofuranyl-3-dibenzofuranamine instead of 4-(1-naphthalenyl)-N-[4-(1-naphthalenyl)phenyl]-benzenamine used in the synthetic method of Compound 21. The molecular weight of the compound measured by FAB-MS was 628. The chemical shift values of the compound measured by $^1$H-NMR were 8.45-8.39 (m, 4H), 8.31 (d, 2H), 8.25 (dd, 4H), 8.08 (d, 2H), 8.02-7.89 (m, 2H), 7.72-7.60 (m, 4H), 7.50-7.40 (m, 5H), 7.33-7.26 (m, 6H). From the results, the white solid compound was identified as Compound 46.

4. Synthesis of Compound 53

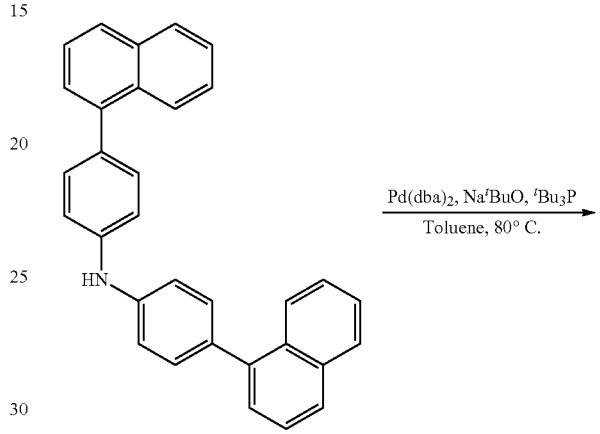

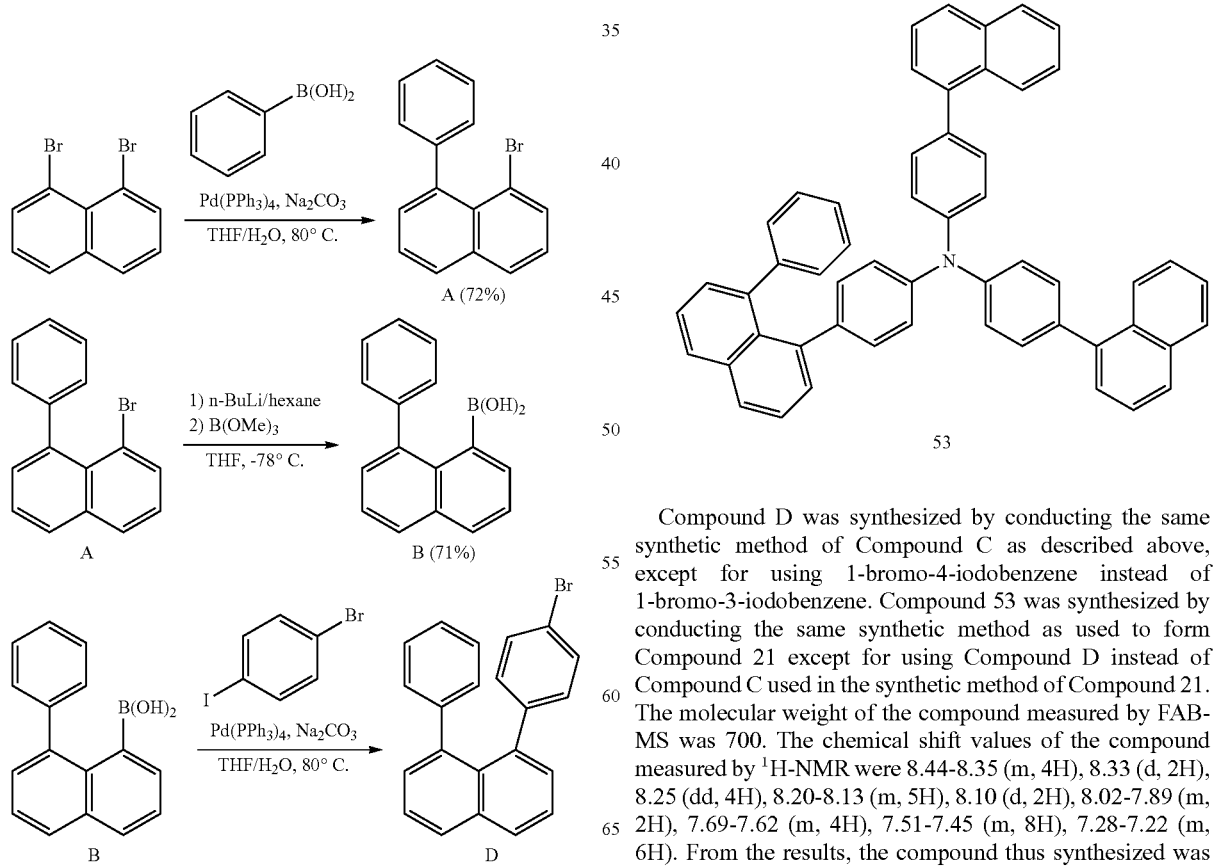

Compound D was synthesized by conducting the same synthetic method of Compound C as described above, except for using 1-bromo-4-iodobenzene instead of 1-bromo-3-iodobenzene. Compound 53 was synthesized by conducting the same synthetic method as used to form Compound 21 except for using Compound D instead of Compound C used in the synthetic method of Compound 21. The molecular weight of the compound measured by FAB-MS was 700. The chemical shift values of the compound measured by $^1$H-NMR were 8.44-8.35 (m, 4H), 8.33 (d, 2H), 8.25 (dd, 4H), 8.20-8.13 (m, 5H), 8.10 (d, 2H), 8.02-7.89 (m, 2H), 7.69-7.62 (m, 4H), 7.51-7.45 (m, 8H), 7.28-7.22 (m, 6H). From the results, the compound thus synthesized was identified as Compound 53.

5. Synthesis of Compound 4

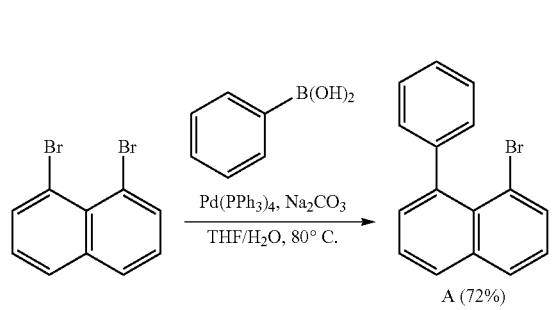

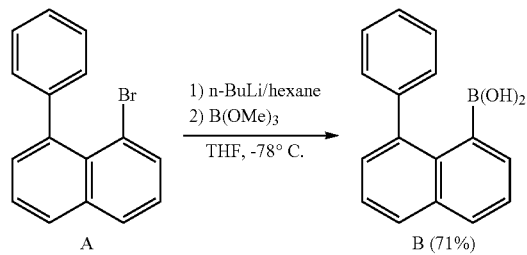

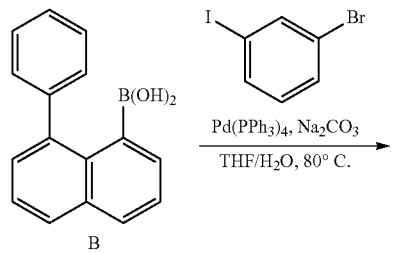

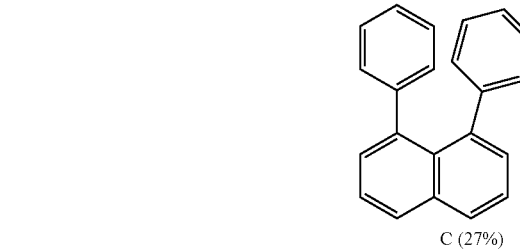

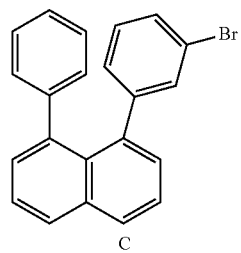

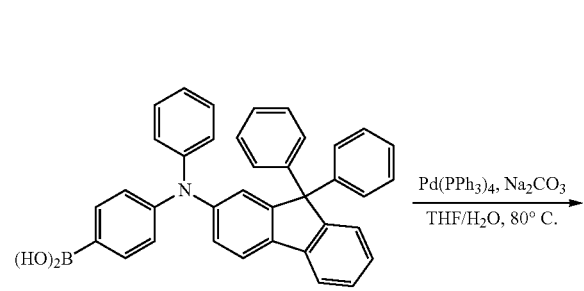

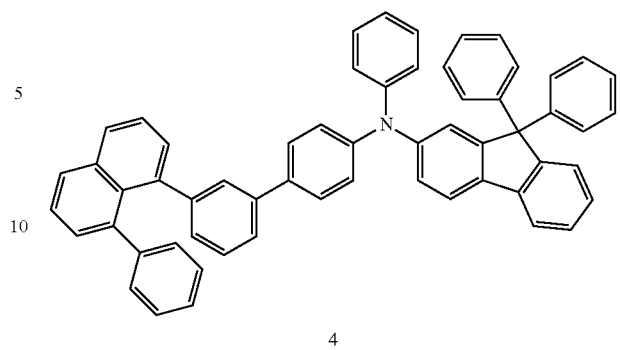

Compound 4 was synthesized by conducting the same synthetic method as used to form Compound 5 except for using B-[4-[(9,9-diphenyl-9H-fluoren-2-yl)phenylamino]phenyl]-boronic acid instead of N-[1,1'-biphenyl]-4-yl-N-[4-(4,4,5,5-tetramethyl-1,3,2-dioxaborolan-2-yl)phenyl]-[1,1'-biphenyl]-4-amine used in the synthetic method of Compound 5. The molecular weight of the compound measured by FAB-MS was 764. The chemical shift values of the compound measured by $^1$H-NMR were 8.44-8.37 (m, 4H), 8.31-8.26 (m, 6H), 8.12 (d, 2H), 8.00-7.89 (m, 8H), 7.77-7.60 (m, 10H), 7.51-7.40 (m, 5H), 7.30-7.24 (m, 6H). From the results, the compound thus synthesized was identified as Compound 4.

6. Synthesis of Compound 59

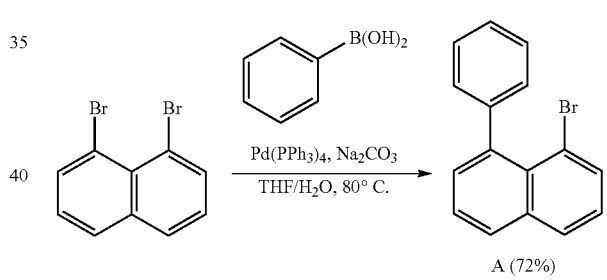

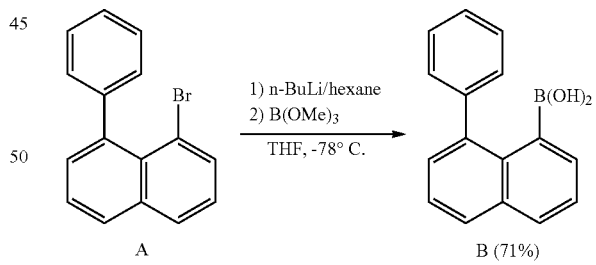

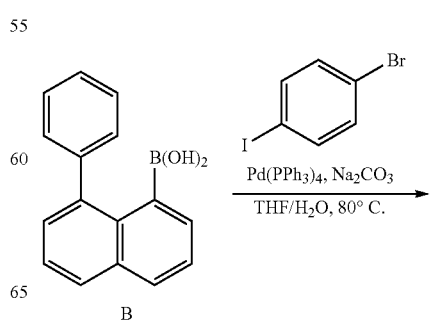

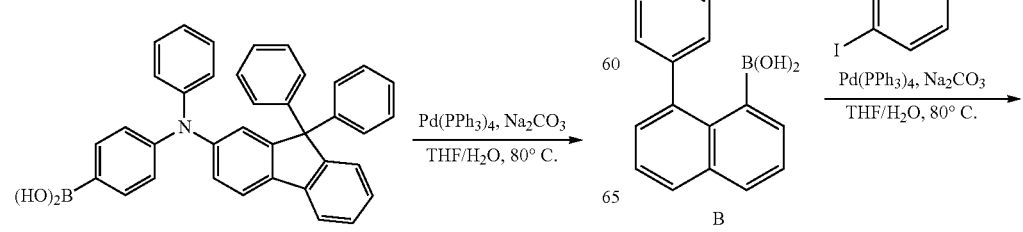

7. Synthesis of Compound 66

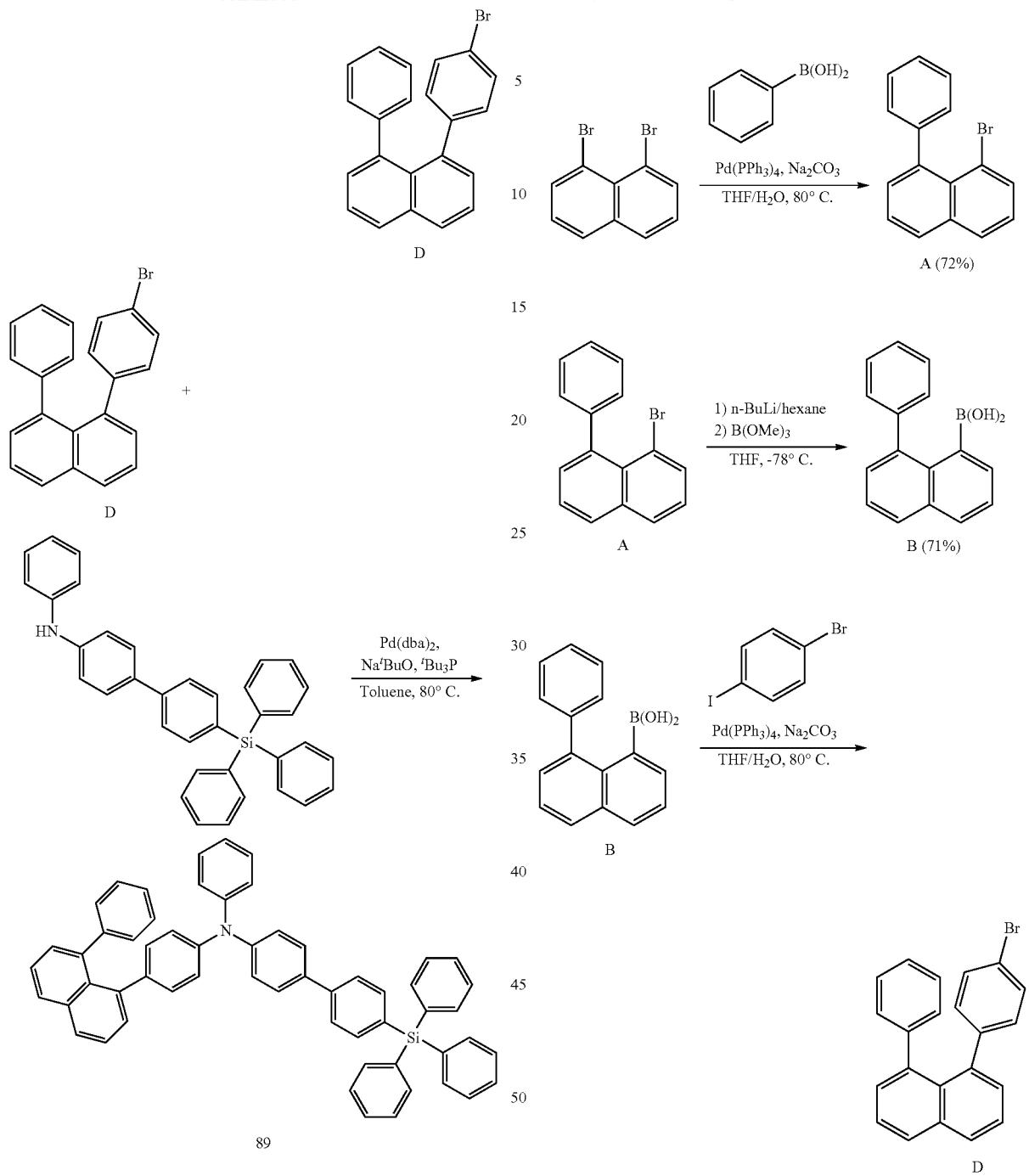

Compound 59 was synthesized by conducting the same synthetic method used to form Compound 53 except for using N-[1,1'-biphenyl]-4-yl-4'-(triphenylsilyl)-benzenamine instead of 4-[1-naphthalenyl]-N-[4-(1-naphthalenyl)phenyl]-benzenamine used in the synthetic method of Compound 53. The molecular weight of the compound measured by FAB-MS was 782. The chemical shift values of the compound measured by $^1$H-NMR were 8.38-8.35 (m, 4H), 8.27-8.19 (m, 6H), 8.16 (d, 2H), 8.10-7.89 (m, 8H), 7.79-7.62 (m, 10H), 7.50-7.35 (m, 5H), 7.29-7.20 (m, 8H). From the results, the compound thus synthesized was identified as Compound 59.

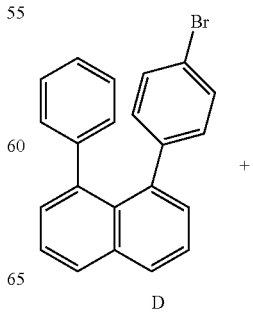

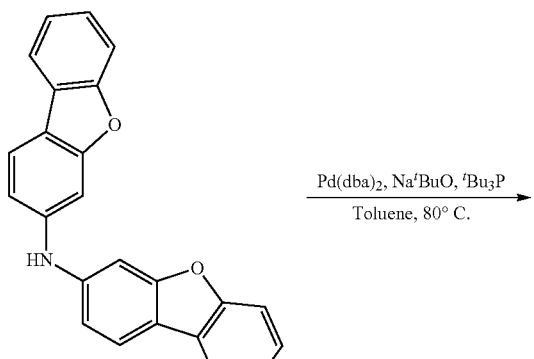

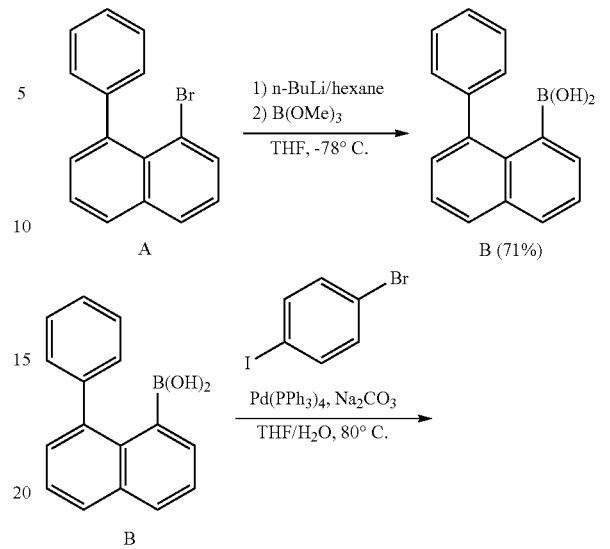

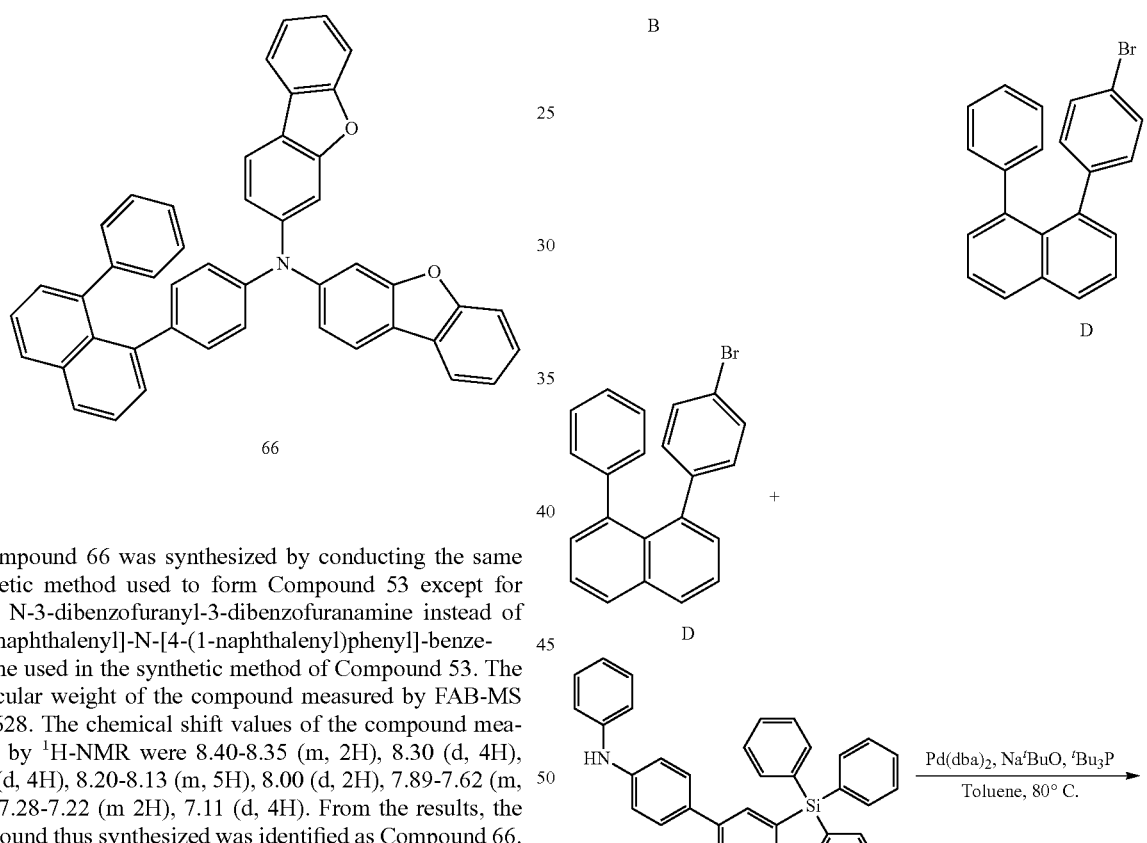

66

Compound 66 was synthesized by conducting the same synthetic method used to form Compound 53 except for using N-3-dibenzofuranyl-3-dibenzofuranamine instead of 4-[1-naphthalenyl]-N-[4-(1-naphthalenyl)phenyl]-benzenamine used in the synthetic method of Compound 53. The molecular weight of the compound measured by FAB-MS was 628. The chemical shift values of the compound measured by $^1$H-NMR were 8.40-8.35 (m, 2H), 8.30 (d, 4H), 8.22 (d, 4H), 8.20-8.13 (m, 5H), 8.00 (d, 2H), 7.89-7.62 (m, 6H), 7.28-7.22 (m 2H), 7.11 (d, 4H). From the results, the compound thus synthesized was identified as Compound 66.

8. Synthesis of Compound 75

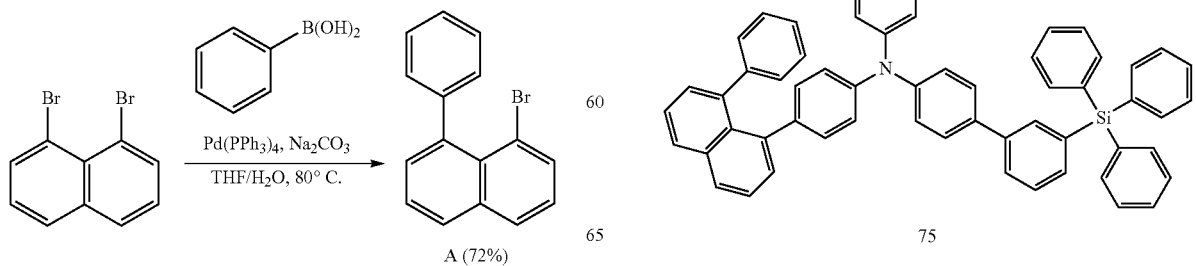

Compound 75 was synthesized by conducting the same synthetic method used to form Compound 59 except for using N-[1,1'-biphenyl]-4-yl-3'-(triphenylsilyl)-benzenamine instead of N-[1,1'-biphenyl]-4-yl-4'-(triphenylsilyl)-benzenamine used in the synthetic method of Compound 59. The molecular weight of the compound measured by FAB-MS was 782. The chemical shift values of the compound measured by $^1$H-NMR were 8.41-8.36 (m, 4H), 8.27-8.19 (m, 6H), 8.16 (d, 2H), 8.12-7.99 (m, 8H), 7.79-7.62 (m, 10H), 7.53-7.41 (m, 4H), 7.29-7.22 (m, 9H). From the results, the compound thus synthesized was identified as Compound 75.

9. Synthesis of Compound 81

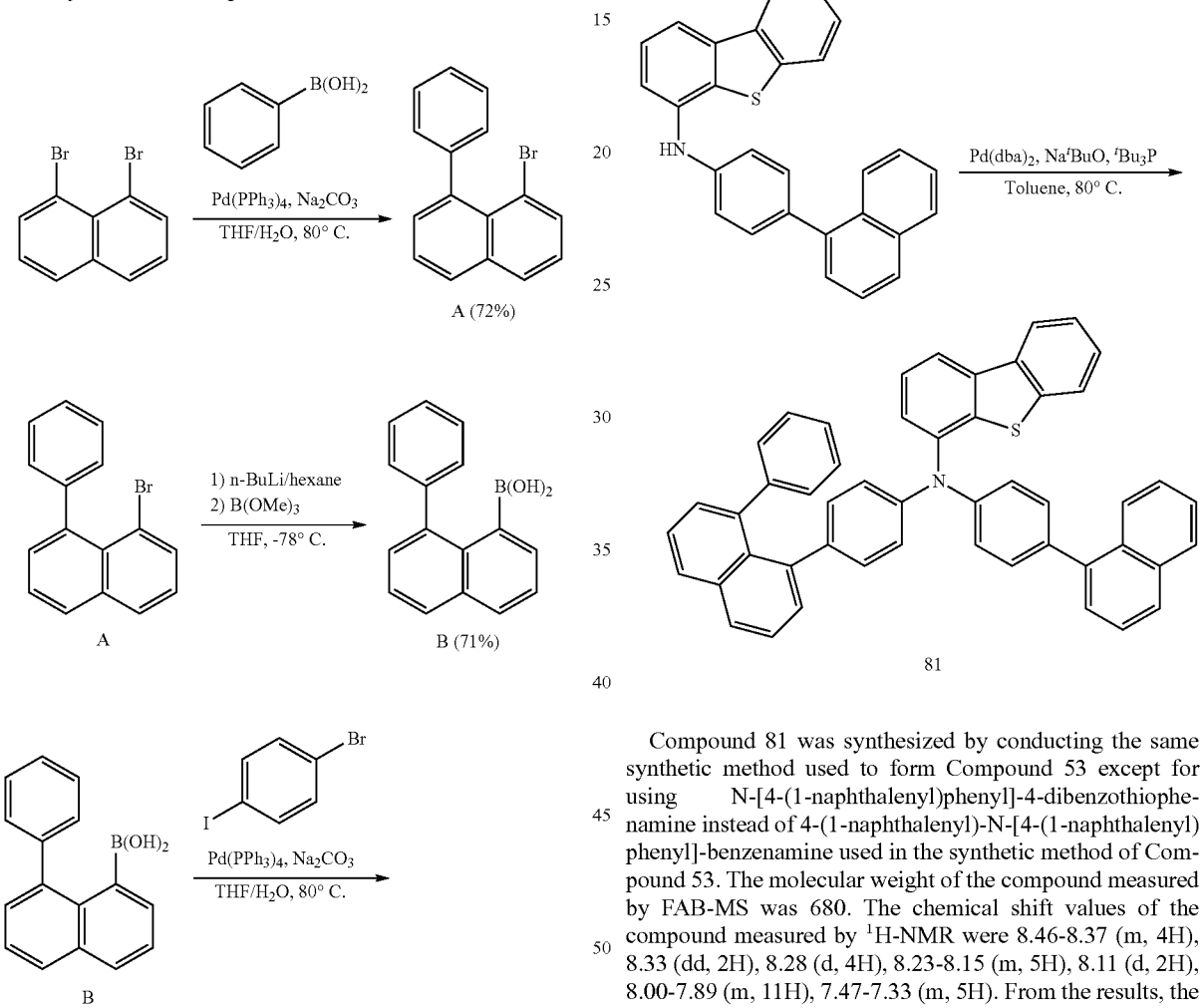

Compound 81 was synthesized by conducting the same synthetic method used to form Compound 53 except for using N-[4-(1-naphthalenyl)phenyl]-4-dibenzothiophenamine instead of 4-(1-naphthalenyl)-N-[4-(1-naphthalenyl)phenyl]-benzenamine used in the synthetic method of Compound 53. The molecular weight of the compound measured by FAB-MS was 680. The chemical shift values of the compound measured by $^1$H-NMR were 8.46-8.37 (m, 4H), 8.33 (dd, 2H), 8.28 (d, 4H), 8.23-8.15 (m, 5H), 8.11 (d, 2H), 8.00-7.89 (m, 11H), 7.47-7.33 (m, 5H). From the results, the compound thus synthesized was identified as Compound 81.

10. Synthesis of Compound 84

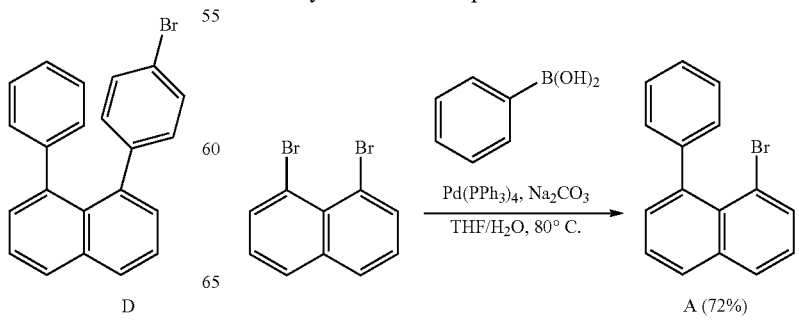

-continued

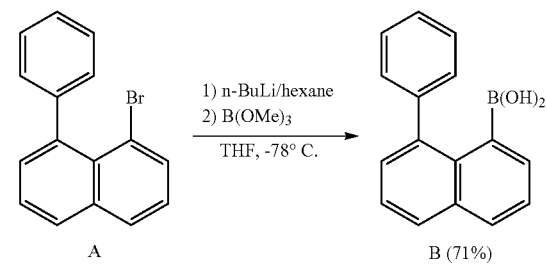

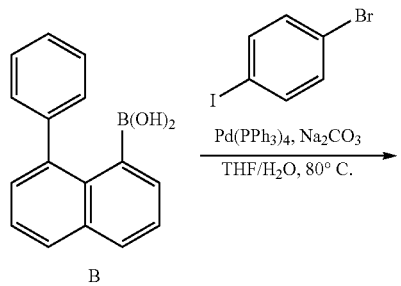

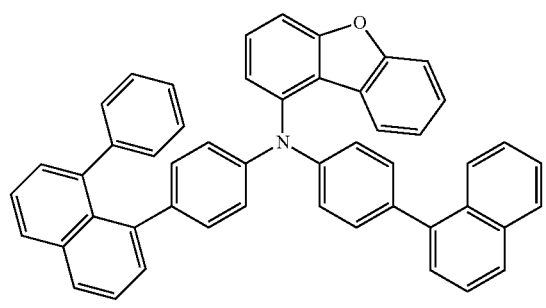

84

Compound 84 was synthesized by conducting the same synthetic method used to form Compound 53 except for using N-[4-(1-naphthalenyl)phenyl]-1-dibenzofuranamine instead of 4-(1-naphthalenyl)-N-[4-(1-naphthalenyl)phenyl]-benzenamine used in the synthetic method of Compound 53. The molecular weight of the compound measured by FAB-MS was 664. The chemical shift values of the compound measured by $^1$H-NMR were 8.42-8.37 (m, 4H), 8.33 (dd, 2H), 8.26 (d, 4H), 8.20-8.14 (m, 5H), 8.11 (d, 2H), 7.99-7.89 (m, 6H), 7.55-7.40 (m, 10H). From the results, the compound thus synthesized was identified as Compound 84.

11. Synthesis of Compound 92

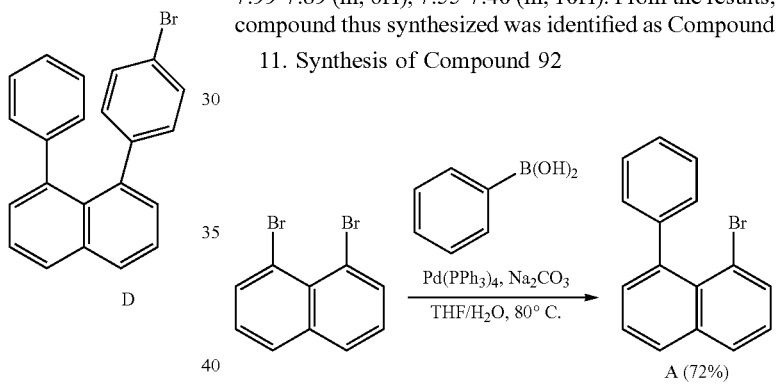

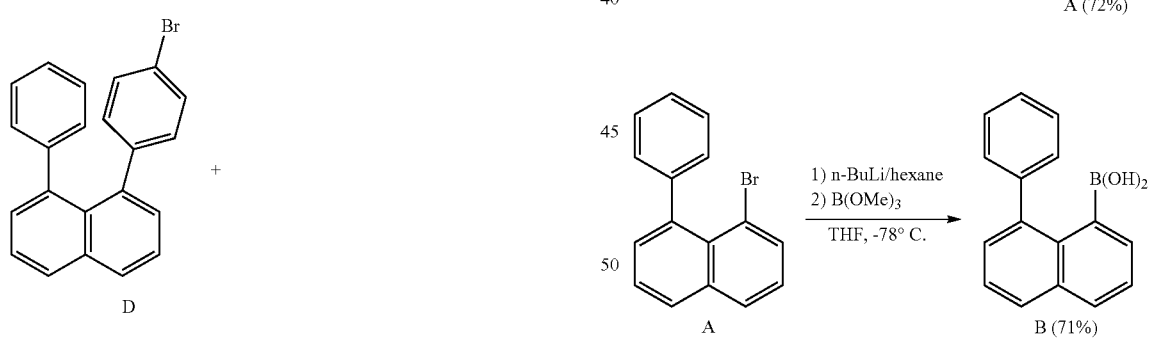

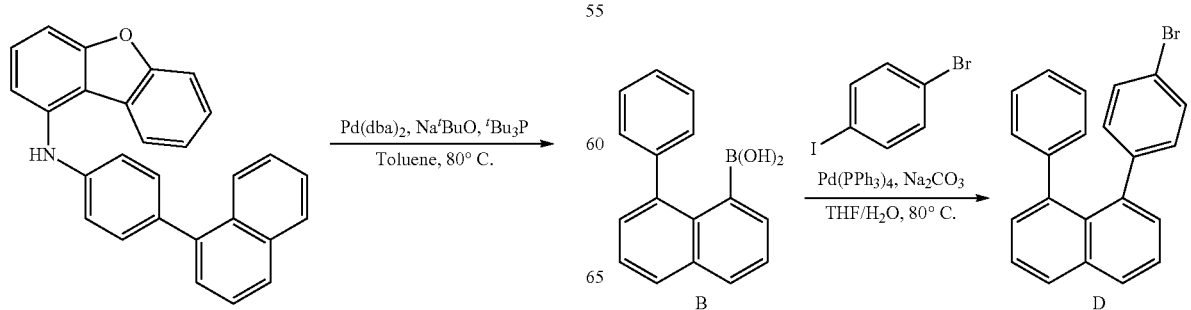

81

-continued

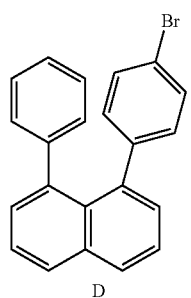

+

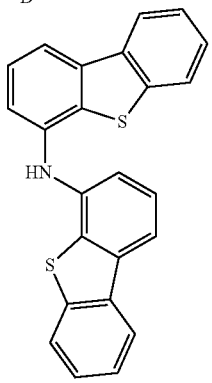

Pd(dba)$_2$, Na$^t$BuO, $^t$Bu$_3$P
Toluene, 80° C.

→

92

Compound 92 was synthesized by conducting the same synthetic method used to form Compound 53 except for using N-[4-dibenzothienyl-4-dibenzothiophenamine instead of 4-(1-naphthalenyl)-N-[4-(1-naphthalenyl)phenyl]-benzenamine used in the synthetic method of Compound 53. The molecular weight of the compound measured by FAB-MS was 660. The chemical shift values of the compound measured by $^1$H-NMR were 8.42-8.37 (m, 7H), 8.31 (d, 2H), 8.19 (d, 2H), 7.99 (d, 2H), 7.81-7.60 (m, 6H), 7.45-7.20 (m, 10H). From the results, the compound thus synthesized was identified as Compound 92.

12. Synthesis of Compound 105

82

-continued

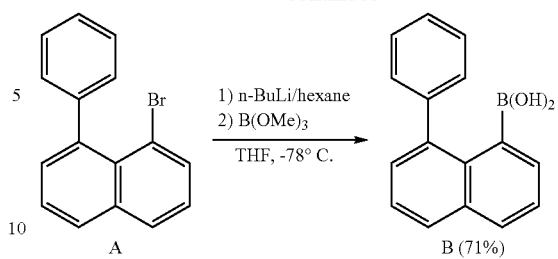

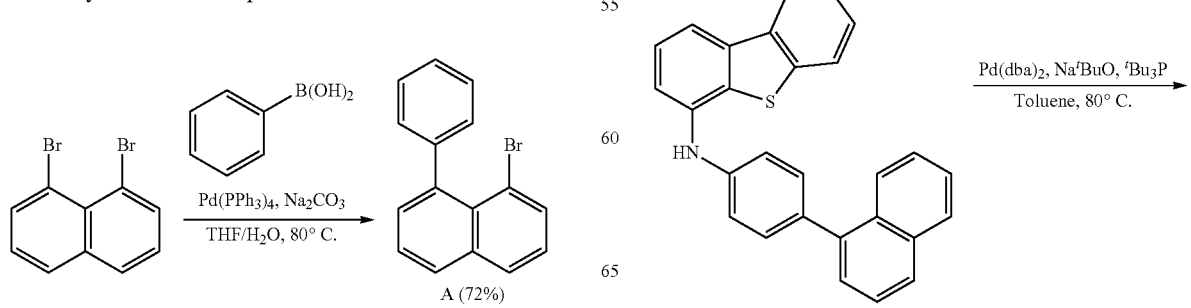

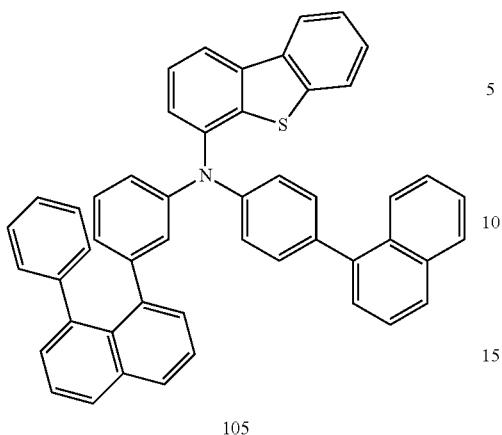

105

Compound 105 was synthesized by conducting the same synthetic method of Compound 81 except for using 1-iodo-3-bromobenzene instead of 1-iodo-4-bromobenzene used in the synthetic method of Compound 81. The molecular weight of the compound measured by FAB-MS was 679. The chemical shift values of the compound measured by 1H-NMR were 8.18-8.11 (m, 1H), 8.07-7.97 (m, 2H), 7.95-7.73 (m, 5H), 7.56-7.29 (m, 14H), 7.23-7.04 (m, 6H), 7.04-6.81 (m, 4H), 6.73-6.61 (m, 1H). From the results, the compound thus synthesized was identified as Compound 105.

13. Synthesis of Compound 77

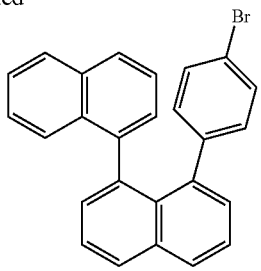

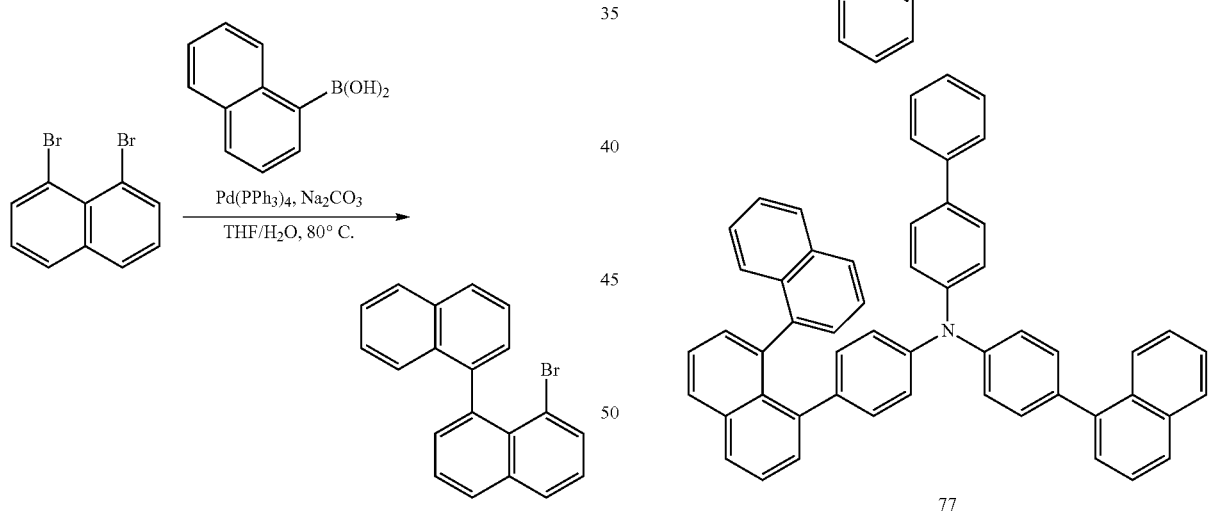

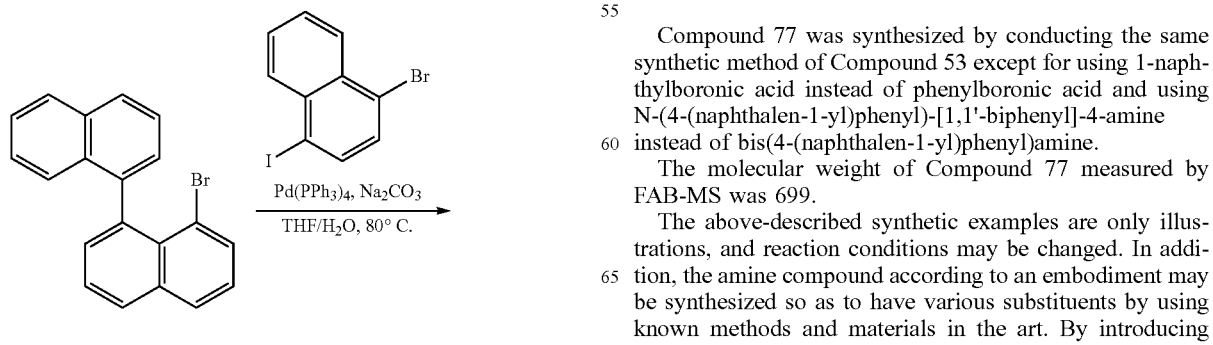

77

Compound 77 was synthesized by conducting the same synthetic method of Compound 53 except for using 1-naphthylboronic acid instead of phenylboronic acid and using N-(4-(naphthalen-1-yl)phenyl)-[1,1'-biphenyl]-4-amine instead of bis(4-(naphthalen-1-yl)phenyl)amine.

The molecular weight of Compound 77 measured by FAB-MS was 699.

The above-described synthetic examples are only illustrations, and reaction conditions may be changed. In addition, the amine compound according to an embodiment may be synthesized so as to have various substituents by using known methods and materials in the art. By introducing various substituents in a core structure represented by Formula 1, appropriate properties for an organic electroluminescence device may be attained.
Device Manufacturing Examples
Organic electroluminescence devices according to Examples 1 to 13 were manufactured using Compounds 4, 5, 21, 46, 53, 59, 66, 75, 81, 84, 92, 105 and 77 as the second hole transport materials.
[Example Compounds]
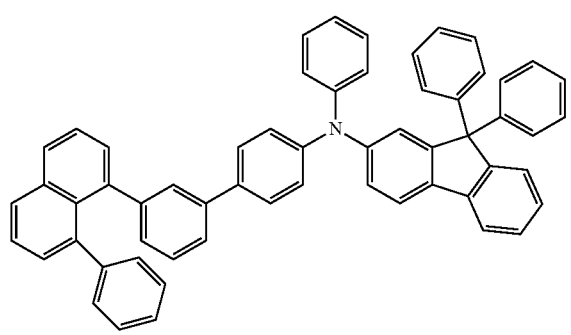
4
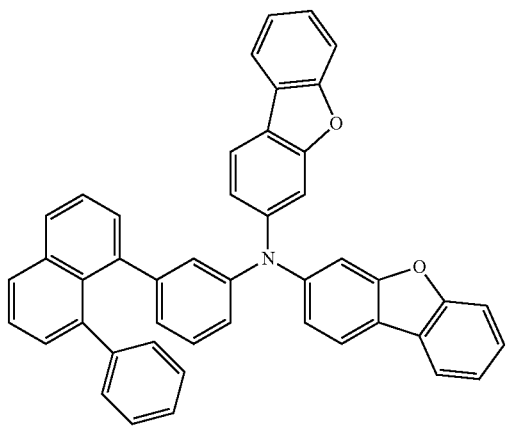
46
5
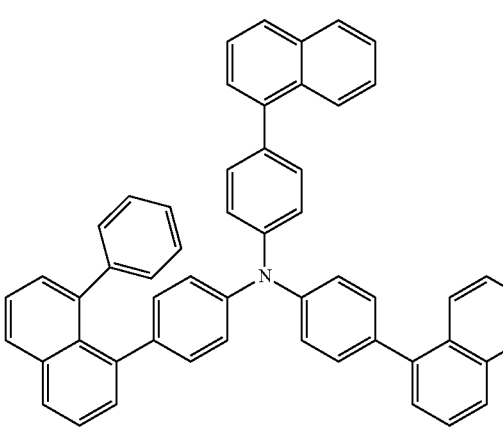
53
21
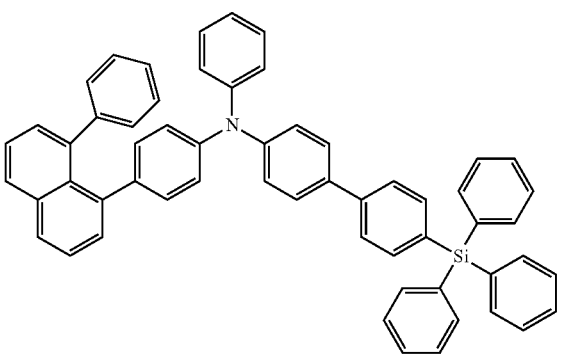
59
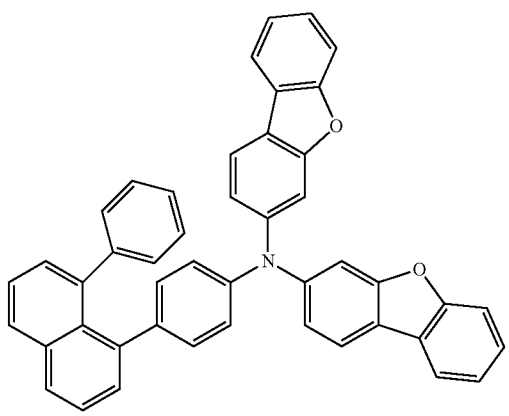
66

75
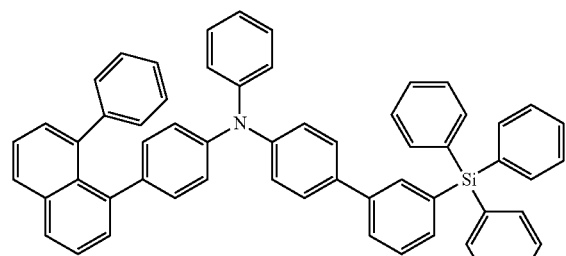
81
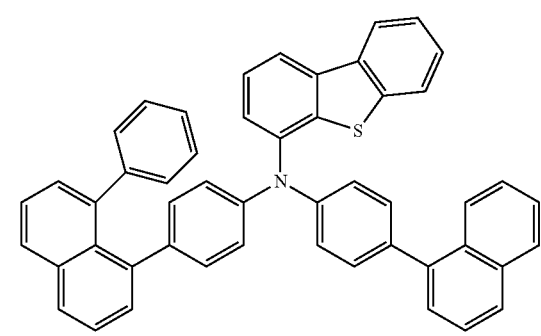
84
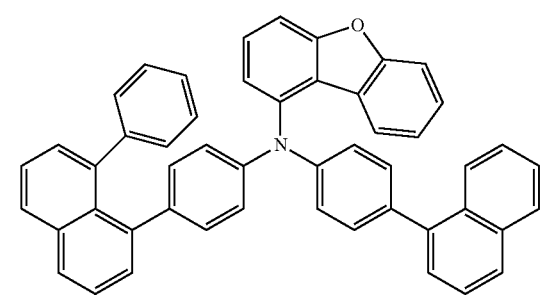
92
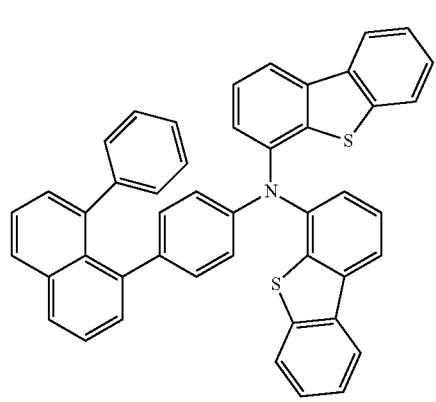
105
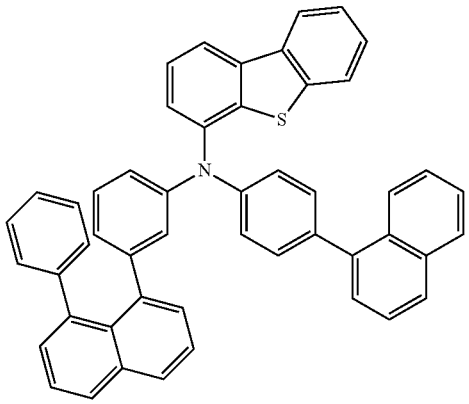
77
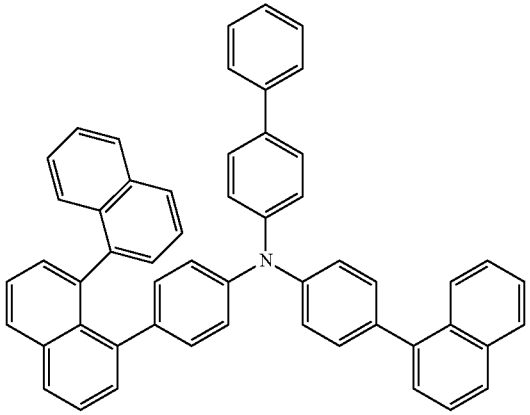
Organic electroluminescent devices of Comparative Examples 1 to 7 were manufactured using the following Comparative Compounds X-1 to X-7 as second hole transport materials.
[Comparative Compounds]
X-1
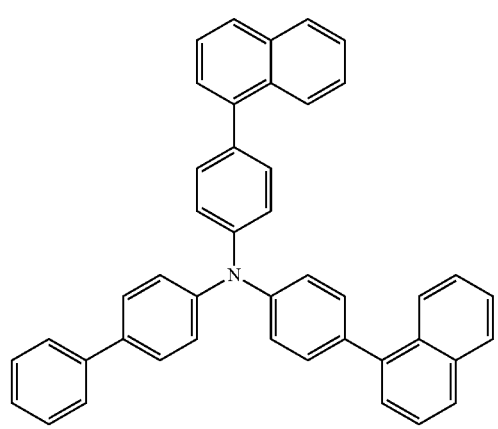

X-2
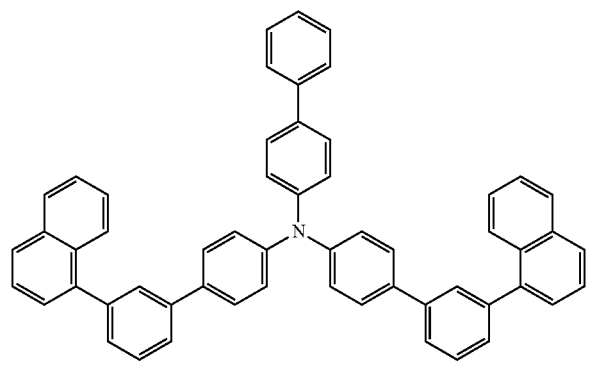

X-3
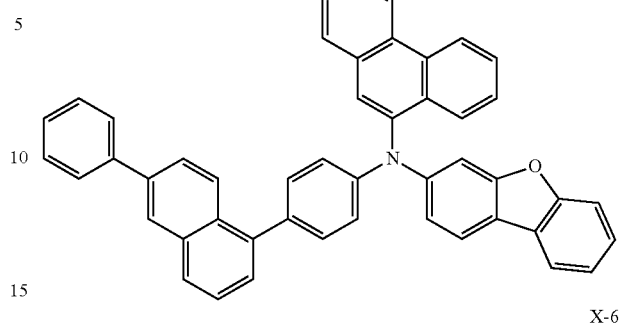

X-4
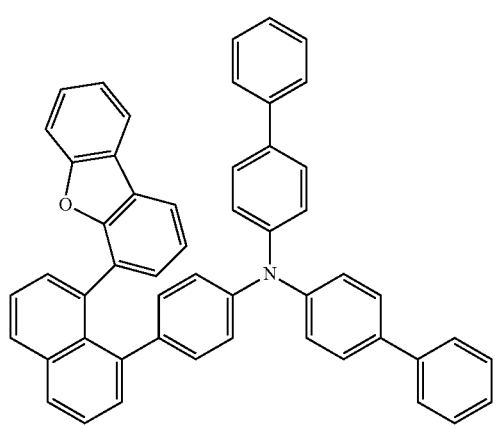

X-5
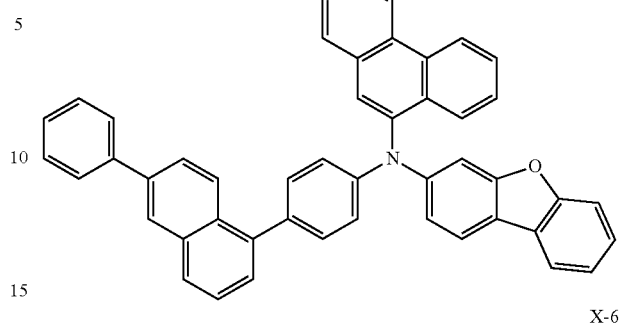

X-6
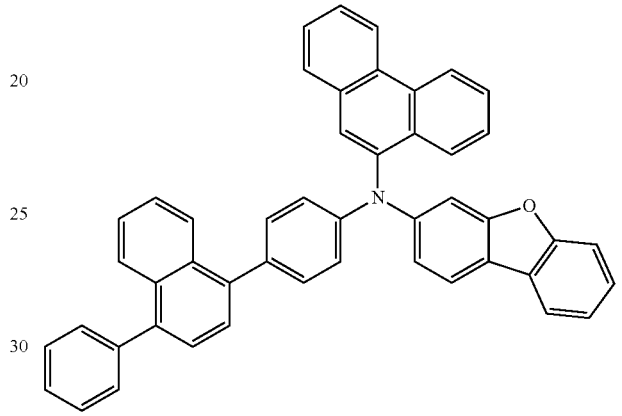

X-7
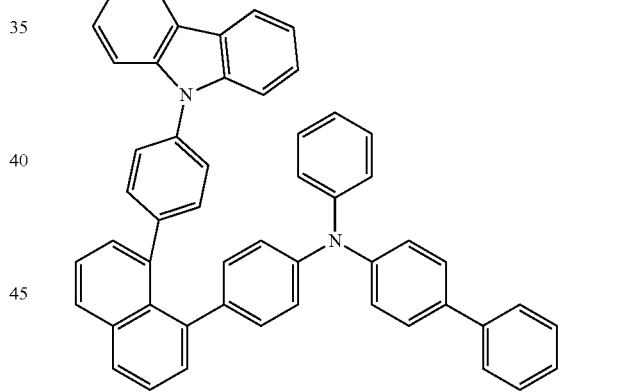

The organic electroluminescence devices according to Examples 1 to 13 and Comparative Examples 1 to 7 were manufactured by forming a first electrode using ITO to a thickness of about 150 nm, forming a hole injection layer using HT1 doped with 2% HIL to a thickness of about 10 nm, forming a first hole transport layer using HT1 to a thickness of about 120 nm, forming a second hole transport layer using a respective example compound or the comparative compound to a thickness of about 30 nm, forming an emission layer using BH doped with 3% BD to a thickness of about 30 nm, forming a first electron transport layer using ET1 to a thickness of about 10 nm, forming a second electron transport layer using ET2 to a thickness of about 20 nm, forming an electron injection layer using LiF to a thickness of about 1 nm, and forming a second electrode using a 10% Ag/Mg alloy to a thickness of about 100 nm. Each layer was formed by a deposition method in a vacuum atmosphere.

The materials applied for the manufacture of the devices are as follows.

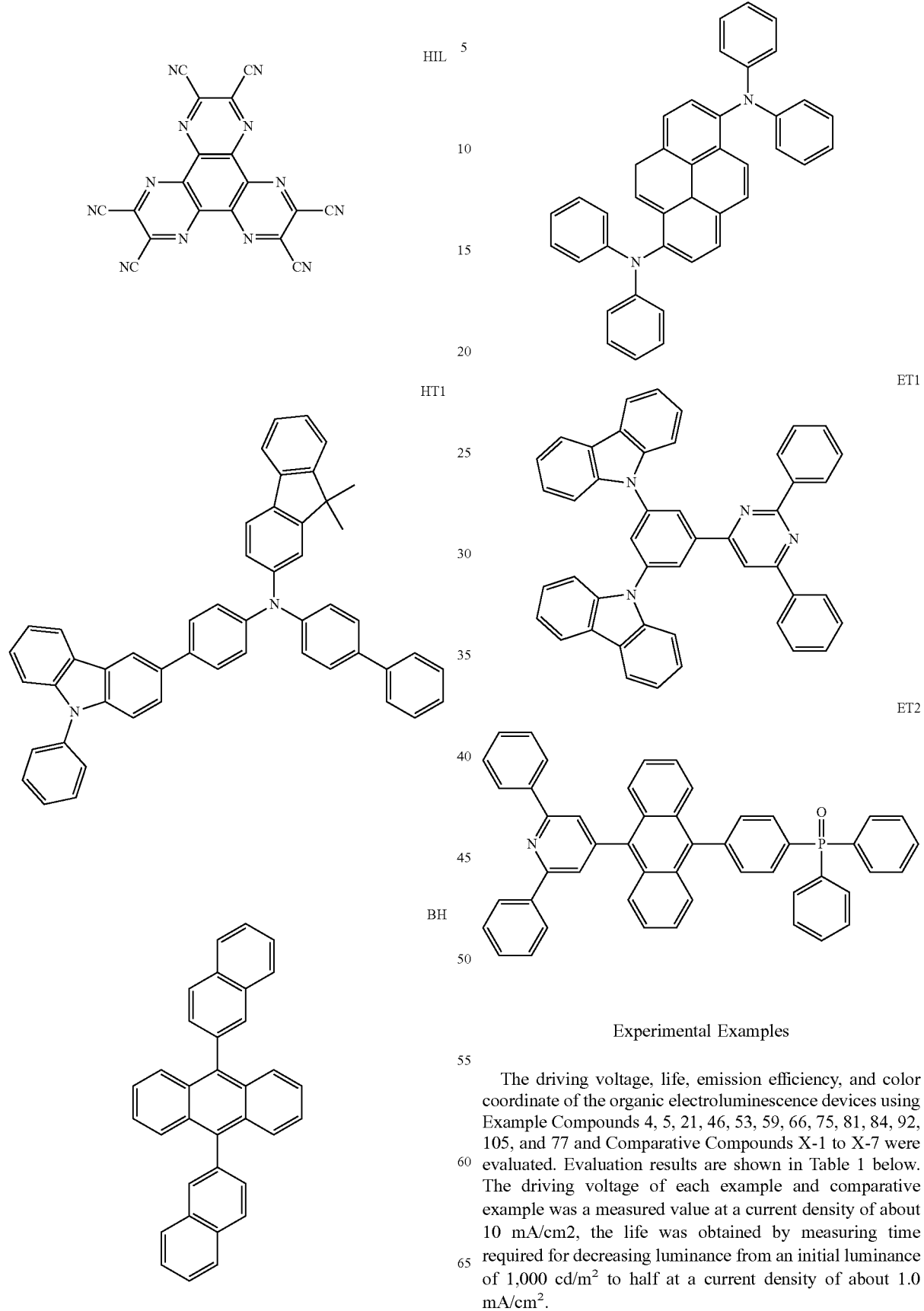

Experimental Examples

The driving voltage, life, emission efficiency, and color coordinate of the organic electroluminescence devices using Example Compounds 4, 5, 21, 46, 53, 59, 66, 75, 81, 84, 92, 105, and 77 and Comparative Compounds X-1 to X-7 were evaluated. Evaluation results are shown in Table 1 below. The driving voltage of each example and comparative example was a measured value at a current density of about 10 mA/cm2, the life was obtained by measuring time required for decreasing luminance from an initial luminance of 1,000 cd/m² to half at a current density of about 1.0 mA/cm².

TABLE 1

| Device manufacturing example | Hole transport layer | Driving voltage (V) | Life LT50(h) | Emission efficiency (cd/A) | Color coordinate CIE (x, y) |
|---|---|---|---|---|---|
| Example 1 | Example Compound 4 | 4.5 | 182 | 5.3 | 0.140, 0.051 |
| Example 2 | Example Compound 5 | 4.7 | 189 | 5.1 | 0.142, 0.051 |
| Example 3 | Example Compound 21 | 4.7 | 183 | 5.4 | 0.140, 0.052 |
| Example 4 | Example Compound 46 | 4.6 | 193 | 5.1 | 0.140, 0.051 |
| Example 5 | Example Compound 53 | 4.8 | 211 | 4.8 | 0.140, 0.051 |
| Example 6 | Example Compound 59 | 4.7 | 203 | 4.9 | 0.141, 0.050 |
| Example 7 | Example Compound 66 | 4.8 | 209 | 4.8 | 0.140, 0.051 |
| Example 8 | Example Compound 75 | 4.9 | 207 | 4.9 | 1.140, 0.051 |
| Example 9 | Example Compound 81 | 4.8 | 210 | 4.9 | 1.140, 0.051 |
| Example 10 | Example Compound 84 | 4.9 | 196 | 5.1 | 0.140, 0.051 |
| Example 11 | Example Compound 92 | 4.9 | 195 | 5.0 | 0.140, 0.051 |
| Example 12 | Example Compound 105 | 4.8 | 187 | 5.1 | 0.140, 0.051 |
| Example 13 | Example Compound 77 | 4.7 | 218 | 4.8 | 0.140, 0.051 |
| Comparative Example 1 | Comparative Compound X-1 | 4.9 | 163 | 3.9 | 0.140, 0.052 |
| Comparative Example 2 | Comparative Compound X-2 | 4.9 | 160 | 3.8 | 0.141, 0.051 |
| Comparative Example 3 | Comparative Compound X-3 | 4.8 | 164 | 3.9 | 0.141, 0.052 |
| Comparative Example 4 | Comparative Compound X-4 | 5.1 | 161 | 4.0 | 0.140, 0.051 |
| Comparative Example 5 | Comparative Compound X-5 | 4.8 | 163 | 4.1 | 0.140, 0.053 |
| Comparative Example 6 | Comparative Compound X-6 | 5.1 | 160 | 4.1 | 0.141, 0.051 |
| Comparative Example 7 | Comparative Compound X-7 | 5.0 | 163 | 4.0 | 0.141, 0.051 |

Referring to the results in Table 1, it may be seen that organic electroluminescence devices according to Examples 1 to 13 had a decreased driving voltage and improved device life and emission efficiency when compared to the organic electroluminescence devices of Comparative Examples 1 to 7. The organic electroluminescence devices of Examples 1 to 13 included an amine compound including a naphthyl group having substituents at position 1 and 8, in a hole transport layer. Accordingly, amine properties may be maintained, and charge tolerance may be improved, thereby decreasing property deterioration due to high temperature heat and charge and attaining long life. In addition, crystallization may be restrained due to the large volume of the substituted naphthyl group. The layer quality of the hole transport layer may be improved and hole transport properties may be improved, thereby attaining a low driving voltage and high efficiency.

The electroluminescence devices of Examples 1 to 4 and 12, which included Example Compounds 4, 5, 21, 46, and 105 in which a linker for connecting an amine group and a substituted naphthyl group is a m-phenylene group, are shown to have greatly improved emission efficiency. When the amine group and the substituted naphthyl group are connected via the m-phenylene group, the volume of an entire molecule is greatly increased. Accordingly, it is believed that layer properties are thereby markedly improved.

The electroluminescence devices according to Examples 5 to 11 and 13, which included Example Compounds 53, 59, 66, 75, 81, 84, 92, and 77 in which a linker for connecting an amine group and a substituted naphthyl group is a p-phenylene group, are shown to have a greatly increased device life. When the amine group and the substituted naphthyl group are connected via the p-phenylene group, a phenyl group substituted onto the naphthyl group and the phenylene group of the linker are disposed in parallel. Accordingly, an orbital of the phenyl group and an orbital of the phenylene group may spatially overlap and a radical state may be stabilized due to through-space interaction.

Comparative Compounds X-1 to X-3, which formed the hole transport layer of the electroluminescence devices of Comparative Examples 1 to 3, include a naphthyl group connected with an amine group at the position 1 of the naphthyl group via a linker. However, an aryl group is not substituted at the position 8. Accordingly thermal and charge tolerance may be deteriorated when compared to that of the example compounds. Accordingly, in the Comparative Examples, a driving voltage was increased, and device life and emission efficiency were decreased.

Comparative Compound X-4, which forms the hole transport layer of the electroluminescence device of Comparative Example 4 include a naphthyl group having substitution sites of 1 and 8. However, a dibenzofuranyl group which is a polycyclic heteroaryl group is substituted at position 8 of the naphthyl group. Accordingly, although the volume of the compound is largely increased, the compound is likely to decompose, and distance between molecules may be increased to decrease the transfer rate of holes, thereby decreasing emission efficiency and device life when compared to those of the examples.

Comparative Compounds X-5 and X-6, which form the hole transport layer of the electroluminescence device of Comparative Examples 5 and 6, include a naphthyl group. However, the substitution position of the aryl group in the naphthyl group is not position 8 but positions 2 and 7. In Comparative Compounds X-5 and X-6, since an aryl group is not substituted at the position 8, which is an active point of the naphthyl group, charge tolerance was deteriorated when compared to that of the example compounds. Accordingly, the electroluminescence devices of Comparative Examples 5 and 6 have decreased emission efficiency and device life when compared to those of the examples.

Comparative Examples 4 and 7 use a compound in which a part corresponding to $Ar^3$ of Formula 1 is a heteroaryl group and have decreased emission efficiency and device life when compared to Examples 1 to 13. Examples 4 and 7 also use a compound including a heteroaryl group, but show difference in efficiency, etc., due to structural difference. More particularly, in Comparative Examples 4 and 7, a relatively unstable heteroaryl group and an arylamine group are spaced apart so as to be positioned at 1 and 8, respectively, with a naphthalene group therebetween. Due to such a structure, the stabilization effect of the heteroaryl group due to nitrogen of the arylamine group may be insufficient, and as a result, efficiency is found to decrease.

The amine compound according to an embodiment may be used as a material for an organic electroluminescence device.

The organic electroluminescence device including the amine compound according to an embodiment may attain a low driving voltage, long life and high emission efficiency.

By way of summation and review, for applying an organic electroluminescence device in a display, a decrease of a driving voltage and an increase of life of the organic electroluminescence device are desirable. Embodiments provide an amine compound to be used in an organic electroluminescence device to achieve a low driving voltage, increased life and high emission efficiency. Embodiments further provide an organic electroluminescence device including the amine compound. The organic electroluminescence device including the amine compound may attain a low driving voltage, long life and high emission efficiency.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope thereof as set forth in the following claims.

What is claimed is:

1. An organic electroluminescence device, comprising:
a first electrode;
a hole transport region disposed on the first electrode;
an emission layer disposed on the hole transport region;
an electron transport region disposed on the emission layer; and
a second electrode disposed on the electron transport region,
wherein the hole transport region comprises an amine compound represented by the following Formula 1:

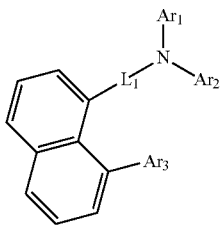

[Formula 1]

wherein in Formula 1, $Ar_1$ and $Ar_2$ are each independently a substituted or unsubstituted aryl group having 6 to 30 ring carbon atoms, or a substituted or unsubstituted heteroaryl group having 2 to 30 ring carbon atoms, and at least one of $Ar_1$ and $Ar_2$ is a substituted or unsubstituted heteroaryl group having 2 to 30 ring carbon atoms, $Ar_3$ is a substituted or unsubstituted aryl group having 6 to 20 ring carbon atoms, and $L_1$ is a substituted or unsubstituted arylene group having 6 to 30 ring carbon atoms, or a substituted or unsubstituted heteroarylene group having 2 to 30 ring carbon atoms.

2. The organic electroluminescence device as claimed in claim 1, wherein the hole transport region comprises:
a hole injection layer disposed on the first electrode; and
a hole transport layer disposed on the hole injection layer, and
the hole transport layer comprises the amine compound represented by Formula 1.

3. The organic electroluminescence device as claimed in claim 2, wherein the hole transport layer contacts the emission layer.

4. The organic electroluminescence device as claimed in claim 1, wherein the hole transport region includes:
a hole injection layer disposed on the first electrode;
a first hole transport layer disposed on the hole injection layer; and
a second hole transport layer disposed on the first hole transport layer, the second hole transport layer being adjacent to the emission layer, and
the second hole transport layer comprises the amine compound represented by Formula 1.

5. The organic electroluminescence device as claimed in claim 1, wherein $Ar_3$ is a substituted or unsubstituted phenyl group, a substituted or unsubstituted naphthyl group, or a substituted or unsubstituted phenanthryl group.

6. The organic electroluminescence device as claimed in claim 1, wherein $Ar_1$ and $Ar_2$ are each independently a substituted or unsubstituted phenyl group, a substituted or unsubstituted naphthylphenyl group, a substituted or unsubstituted naphthyl group, a substituted or unsubstituted biphenyl group, a substituted or unsubstituted terphenyl group, a substituted or unsubstituted phenanthryl group, a substituted or unsubstituted fluorenyl group, a substituted or unsubstituted dibenzofuranyl group, or a substituted or unsubstituted dibenzothiophenyl group.

7. The organic electroluminescence device as claimed in claim 1, wherein in case where $Ar_3$ is substituted, a substituent is at least one of deuterium, a silyl group, an alkyl group, or an aryl group.

8. The organic electroluminescence device as claimed in claim 1, wherein at least one of $Ar_1$ or $Ar_2$ is a substituted or unsubstituted dibenzofuranyl group, or a substituted or unsubstituted dibenzothiophenyl group.

9. The organic electroluminescence device as claimed in claim 1, wherein Formula 1 is represented by one of the following Formula 1-1 to Formula 1-4:

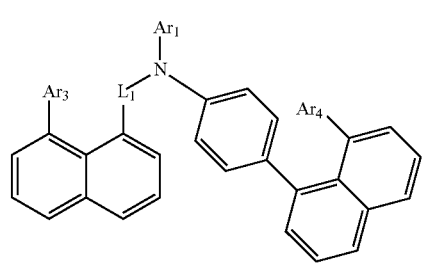

[Formula 1-1]

wherein in Formula 1-1,

Ar₁ is a substituted or unsubstituted heteroaryl group having 2 to 30 ring carbon atoms, Ar₄ is a substituted or unsubstituted aryl group having 6 to 20 ring carbon atoms, and Ar₃, and L₁ are the same as defined in claim 1,

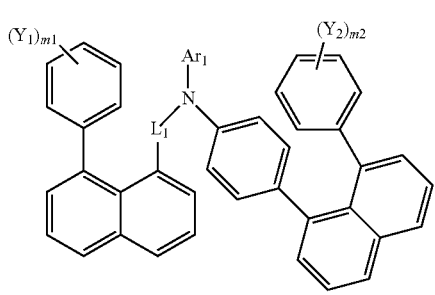

[Formula 1-2]

wherein in Formula 1-2,

Ar₁ is a substituted or unsubstituted heteroaryl group having 2 to 30 ring carbon atoms, Y₁ and Y₂ are each independently a hydrogen atom, a deuterium atom, a halogen atom, an alkyl group, or an aryl group, or may be combined with an adjacent group to form a ring, m₁ and m₂ are each independently an integer of 0 to 5, and L₁ is the same as defined in claim 1,

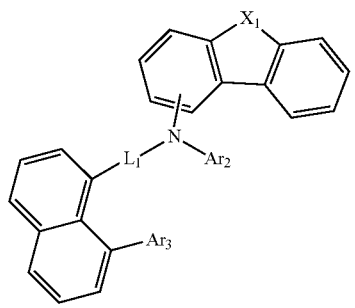

[Formula 1-3]

wherein in Formula 1-3,

X₁ is O or S, and

Ar₂, Ar₃, and L₁ are the same as defined in claim 1,

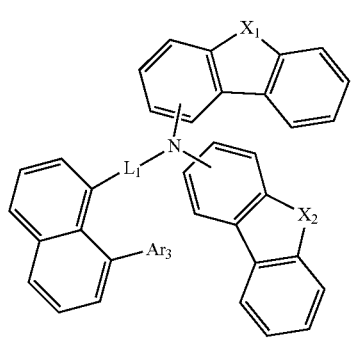

[Formula 1-4]

wherein in Formula 1-4,

X₁ and X₂ are each independently O or S, and

Ar₃, and L₁ are the same as defined in claim 1.

10. The organic electroluminescence device as claimed in claim 1, wherein L₁ is represented by the following Formula 2-1 or 2-2:

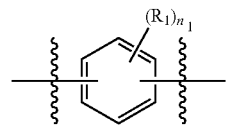

[Formula 2-1]

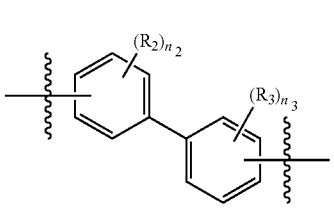

[Formula 2-2]

wherein in Formulae 2-1 and 2-2, R₁ to R₃ are each independently a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, and n₁ to n₃ are each independently an integer of 0 to 4.

11. The organic electroluminescence device as claimed in claim 10, wherein L₁ is represented by the following Formula 2-3 or 2-4:

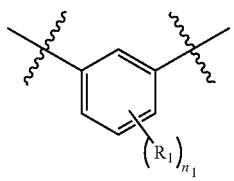

[Formula 2-3]

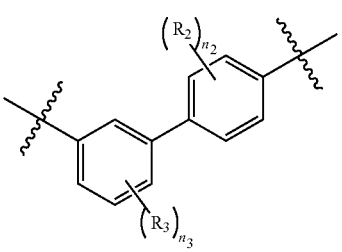

[Formula 2-4]

wherein in Formulae 2-3 and 2-4, R₁ to R₃, and n₁ to n₃ are the same as defined in claim 10.

12. The organic electroluminescence device as claimed in claim 10, wherein $L_1$ is represented by the following Formula 2-5 or 2-6:

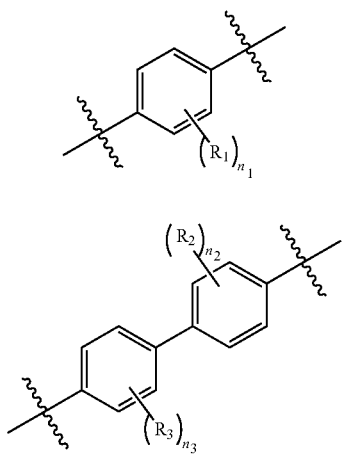

[Formula 2-5]

[Formula 2-6]

wherein in Formulae 2-5 and 2-6, $R_1$ to $R_3$, and $n_1$ to $n_3$ are the same as defined in claim 10.

13. The organic electroluminescence device as claimed in claim 1, wherein the amine compound represented by Formula 1 is any one selected from compounds represented in the following Compound Groups 1 to 4:

[Compound Group 1]

9

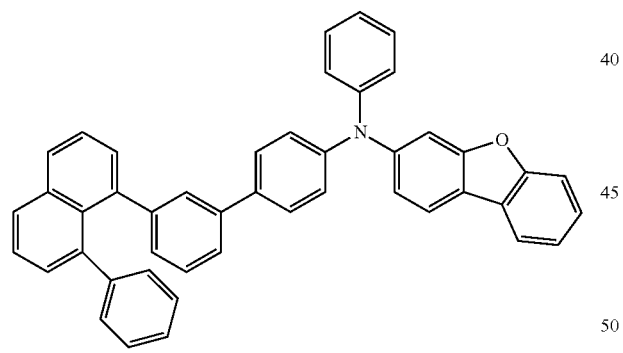

10

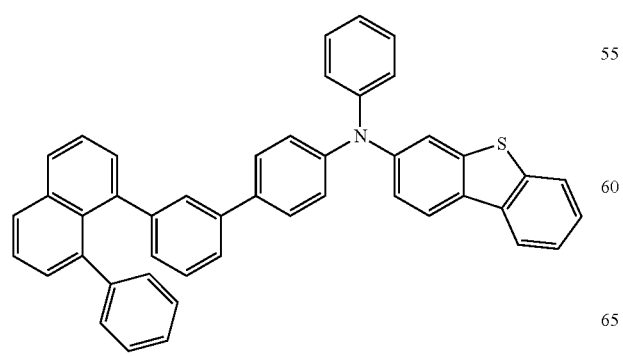

11

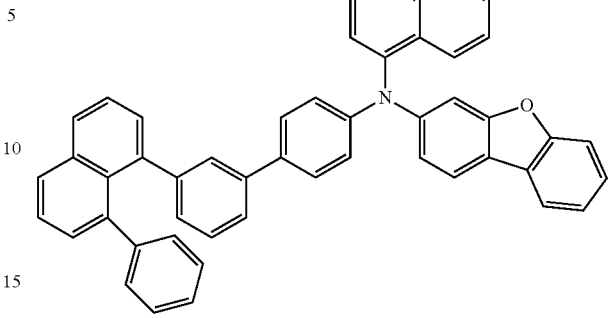

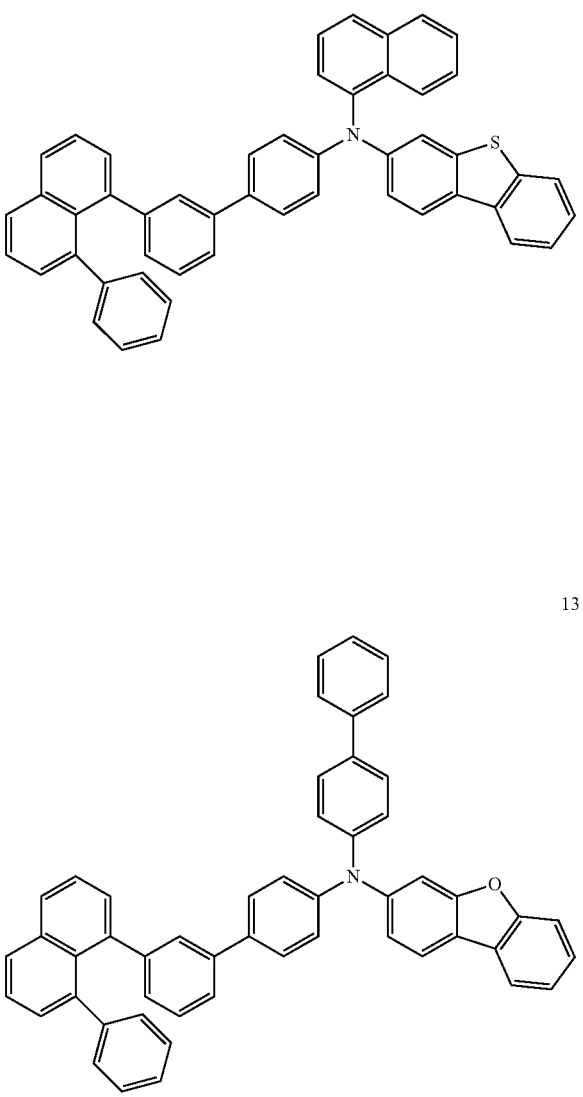

14
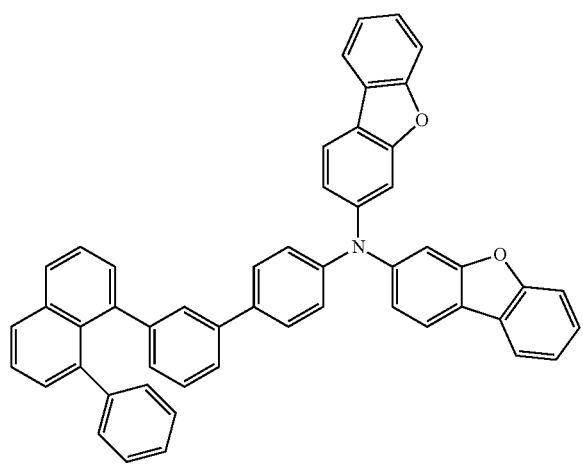
15
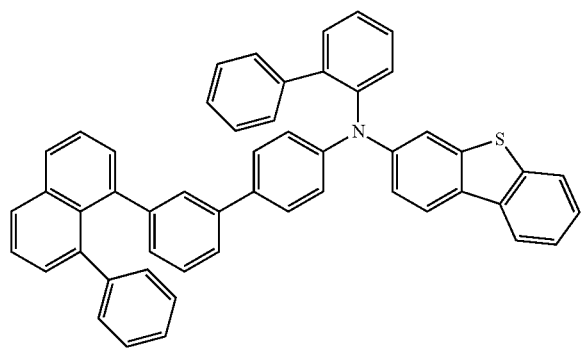
16
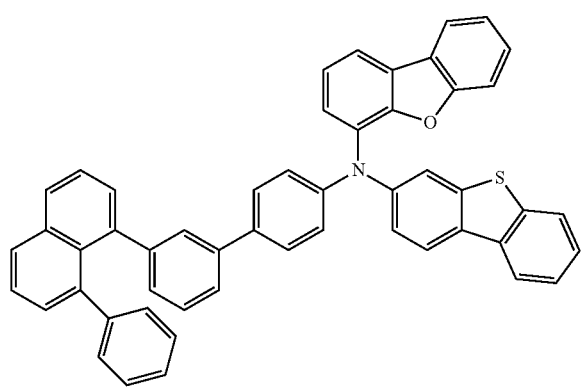
41
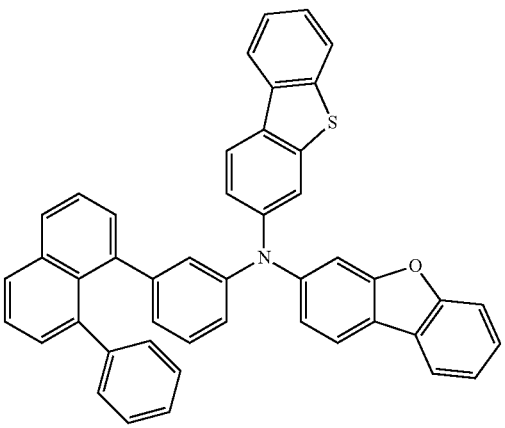
42
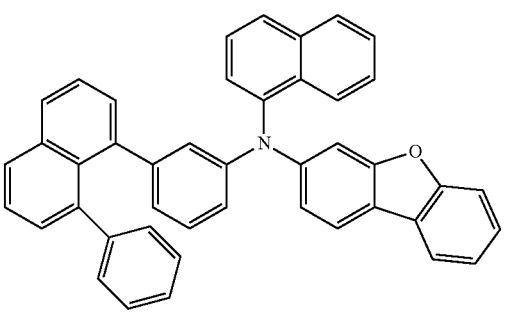
43
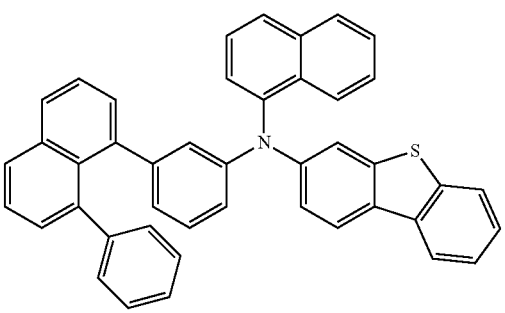
44

45
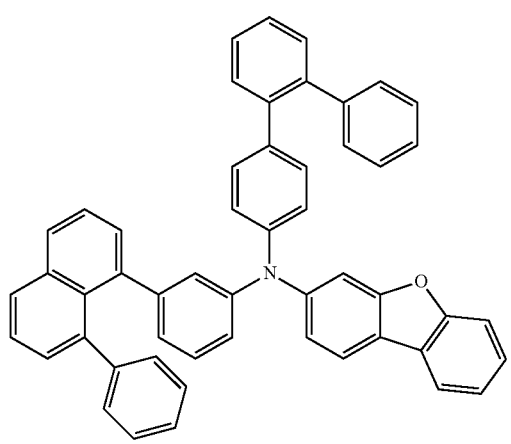
46
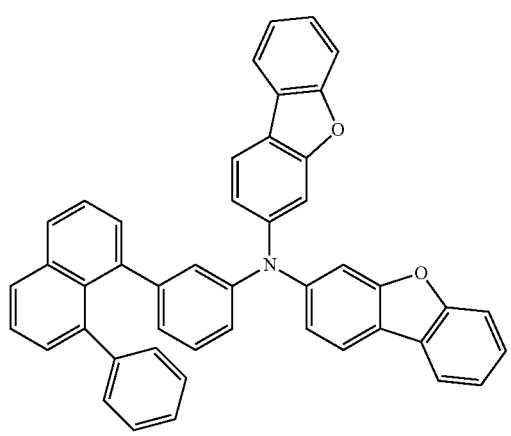
47
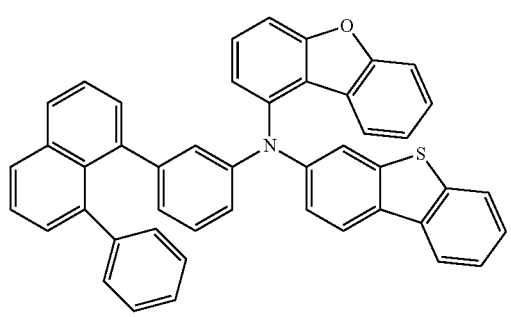
48
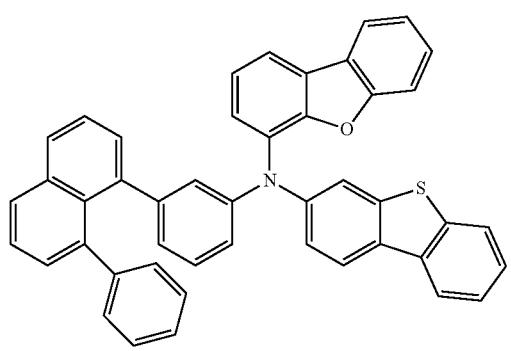
[Compound Group 2]
61
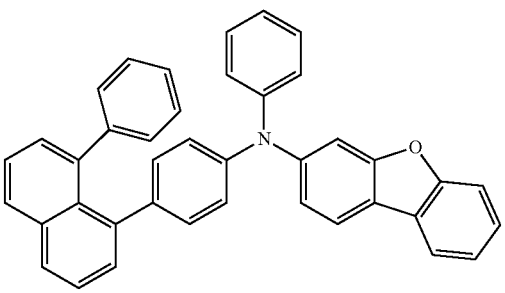
62
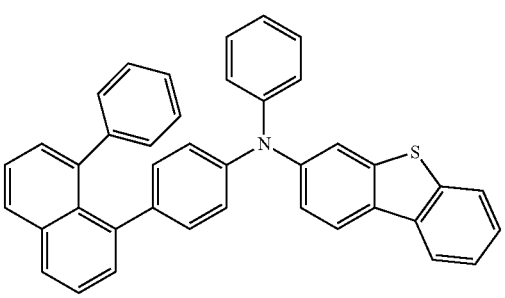
63
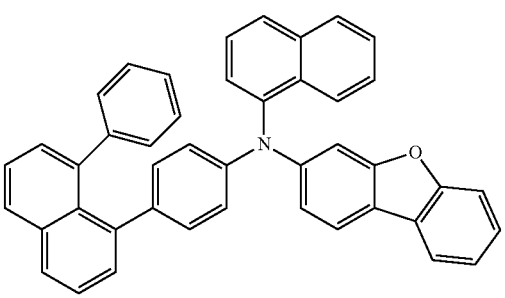
64
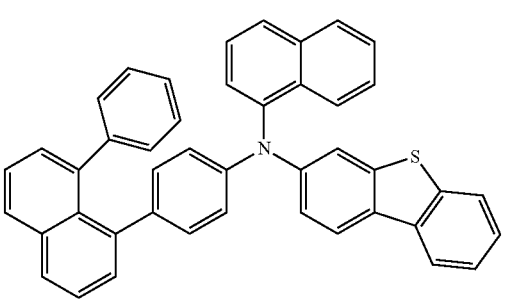
65
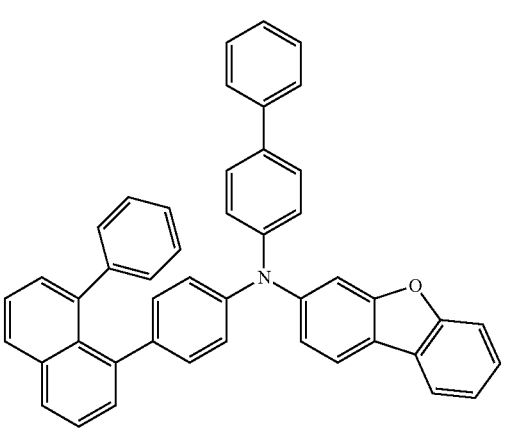

66
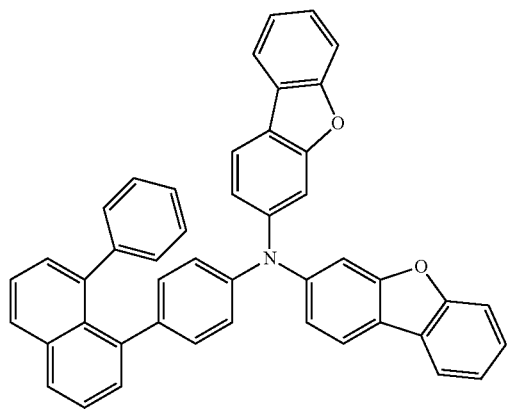
67
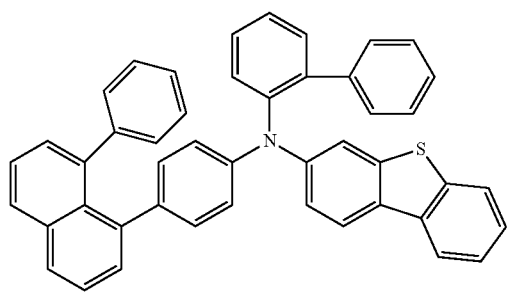
68
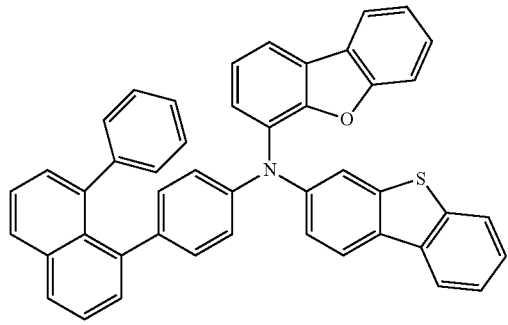
81
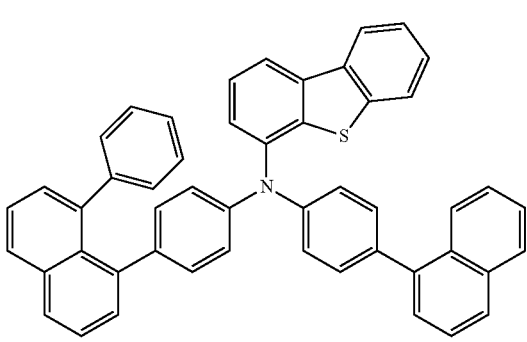
82
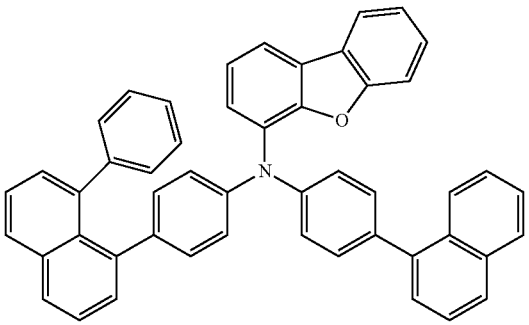
83
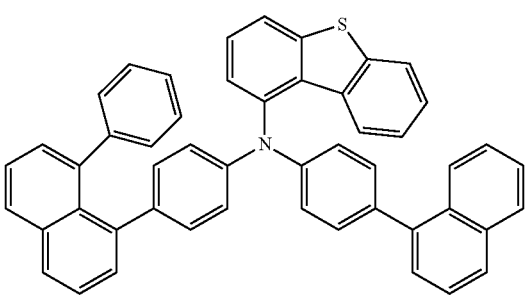
84
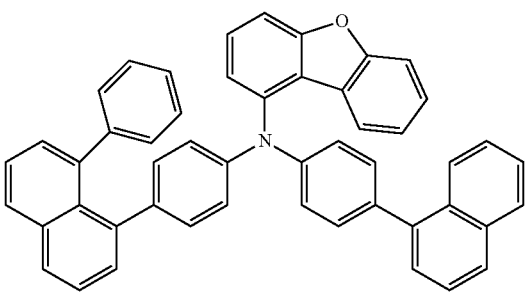
85
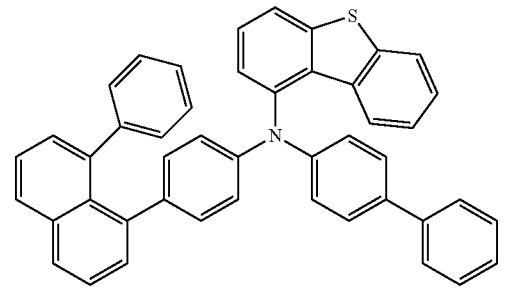
86
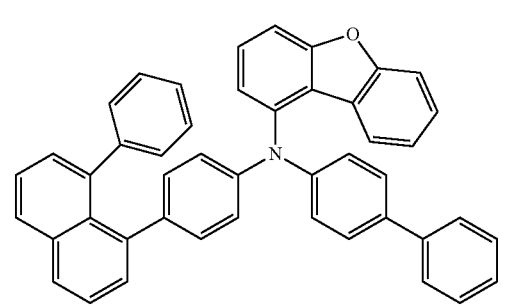

91
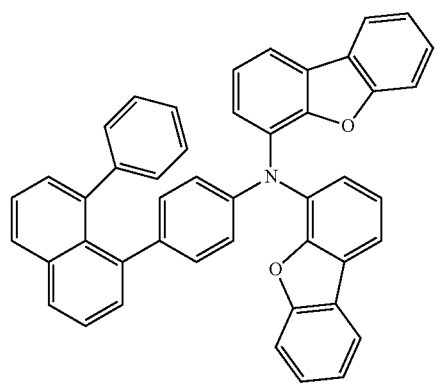
92
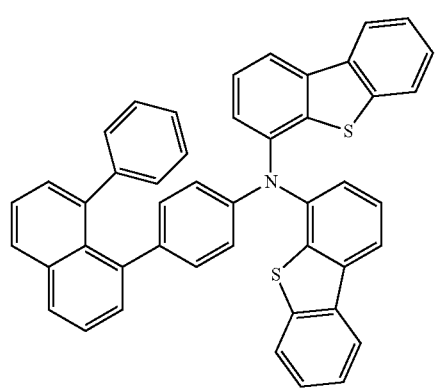
93
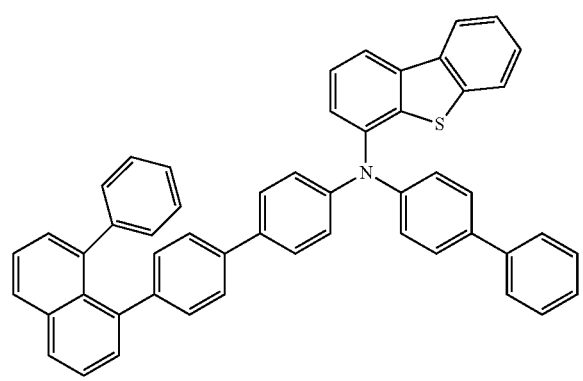
[Compound Group 3]
97
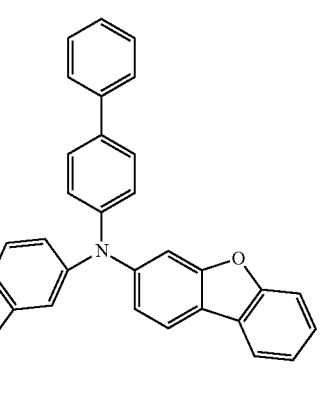
98
99
100
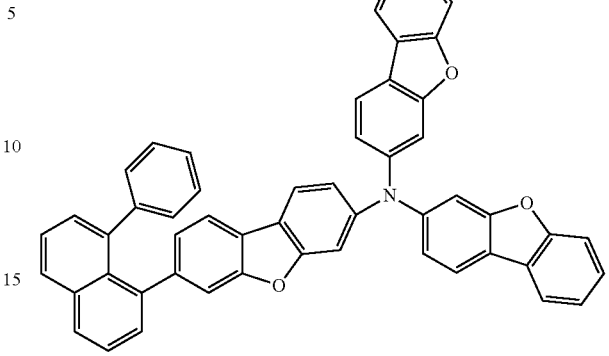
101
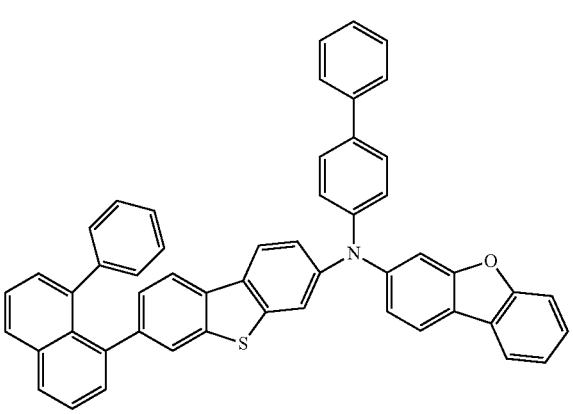

102
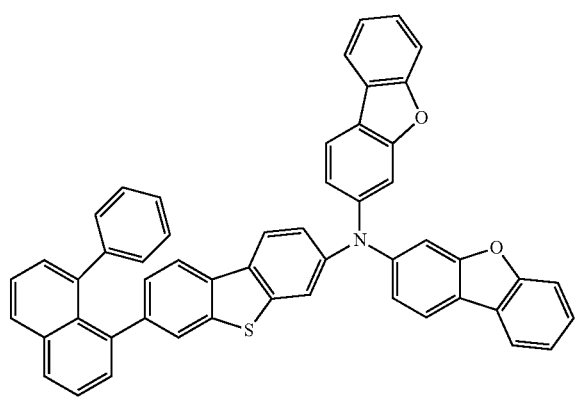
103
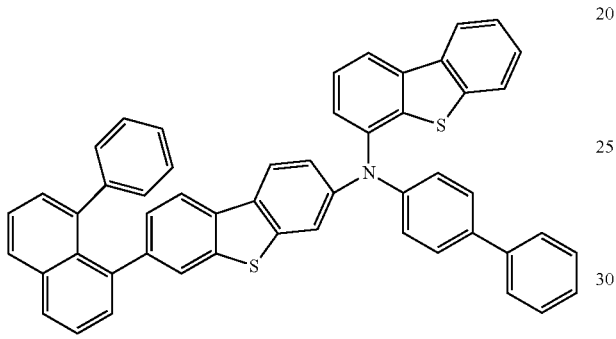
104
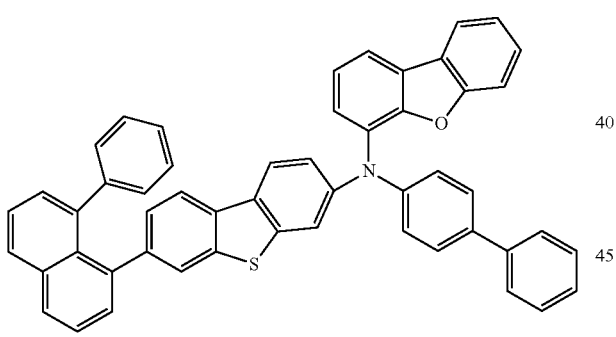
[Compound Group 4]
105
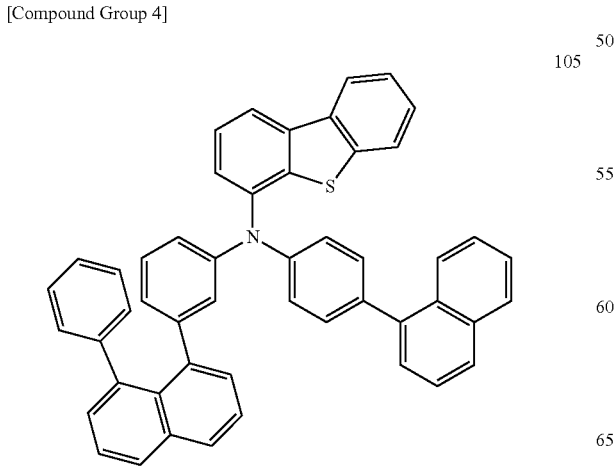
106
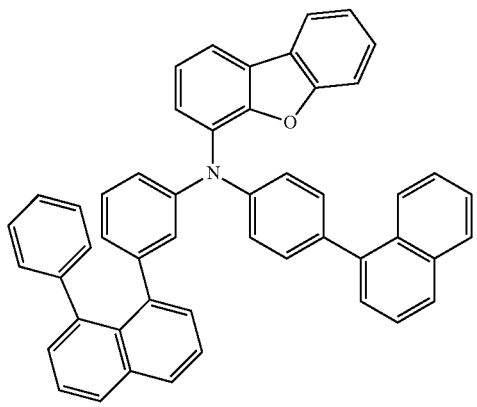
107
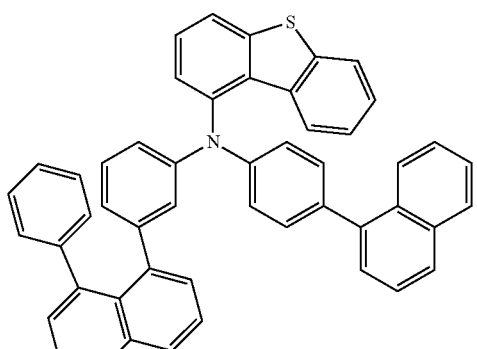
108
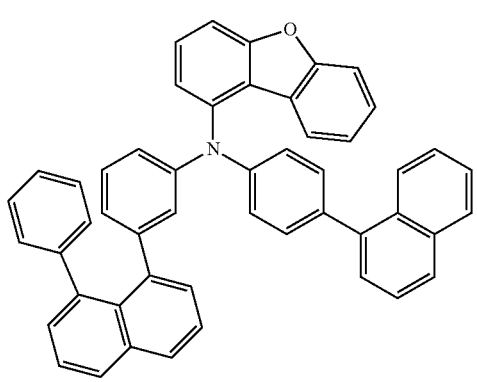
109
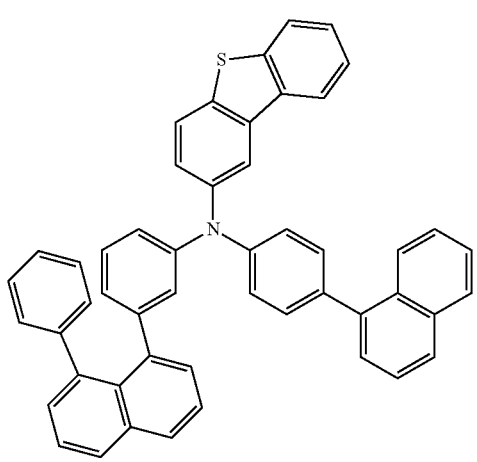

111
-continued
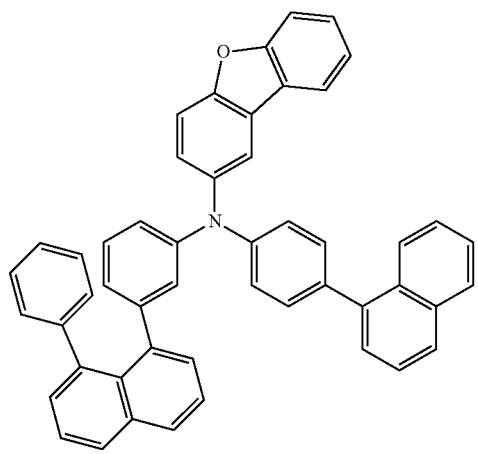
110
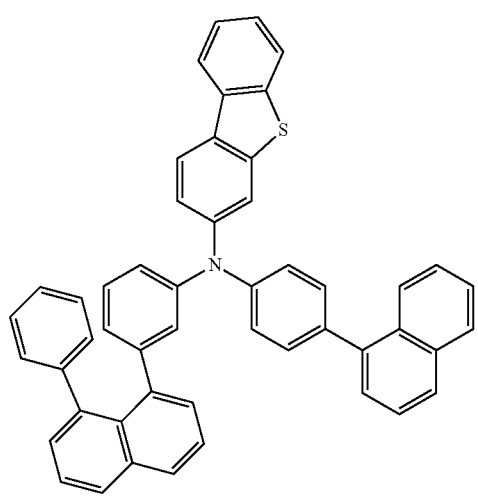
111
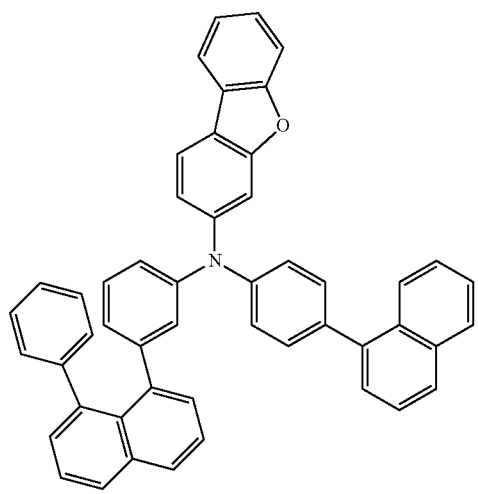
112
112
-continued
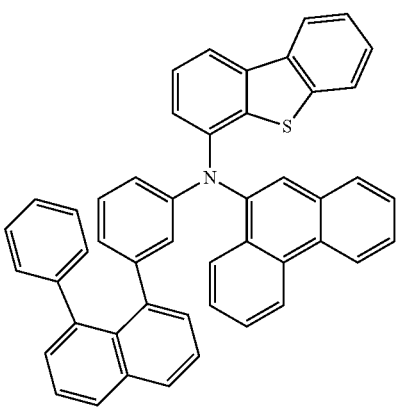
113
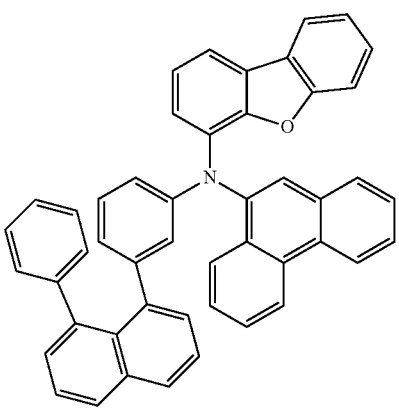
114
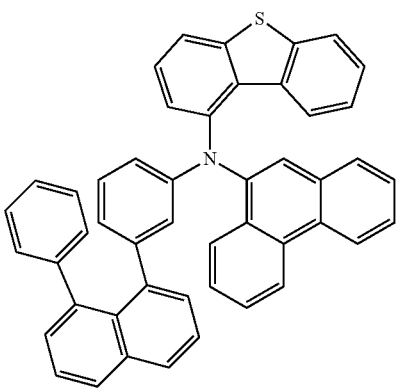
115
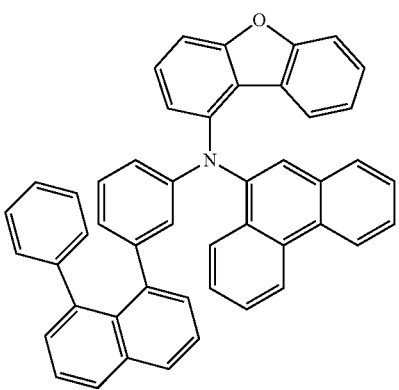
116

117
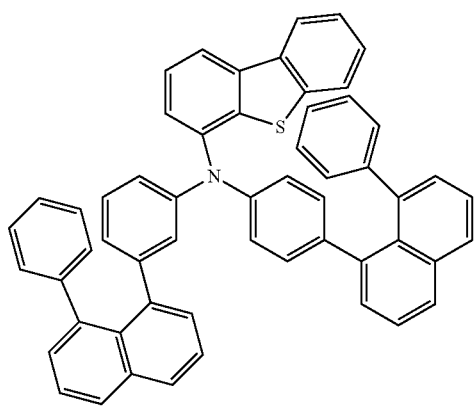
118
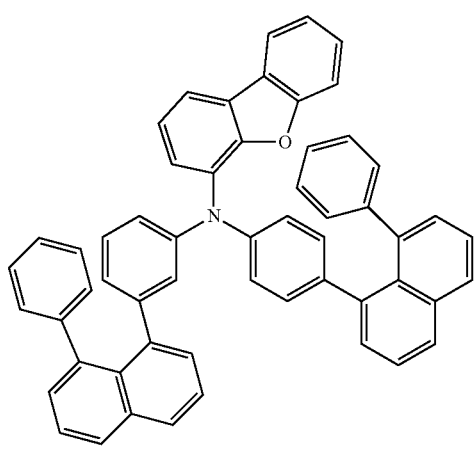
119
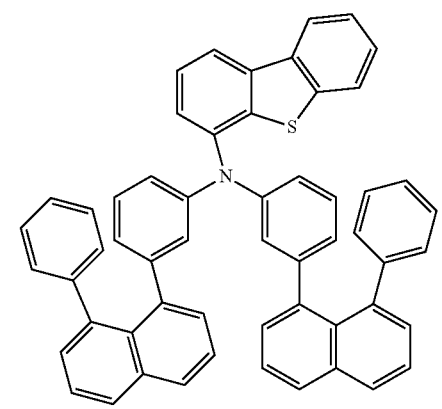
120
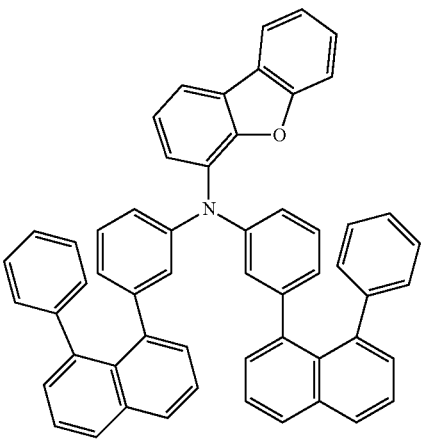
121
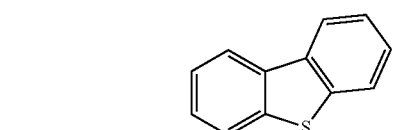
122
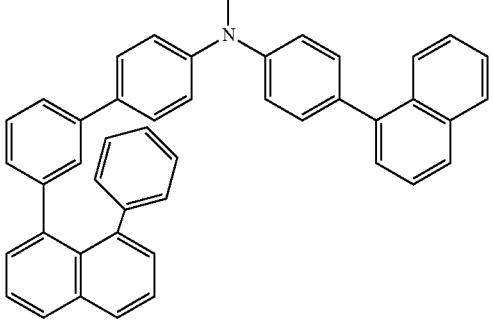
123

124
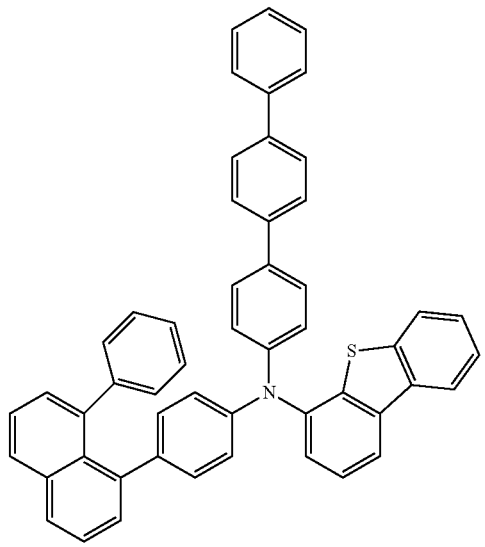
125
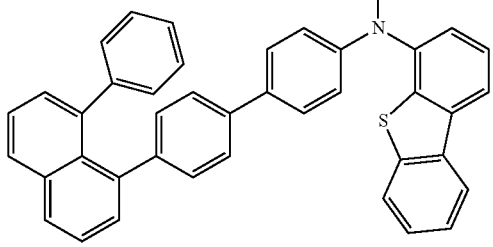
126
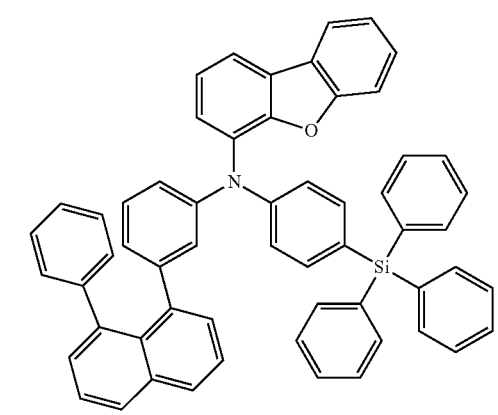
127
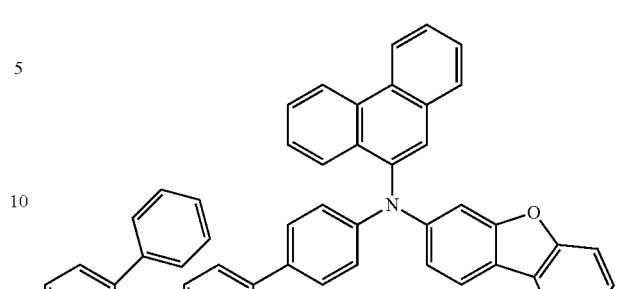
128
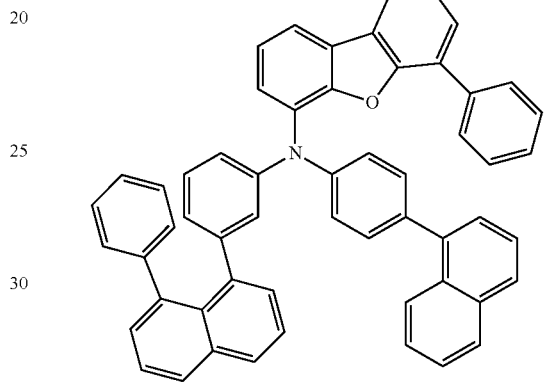
129
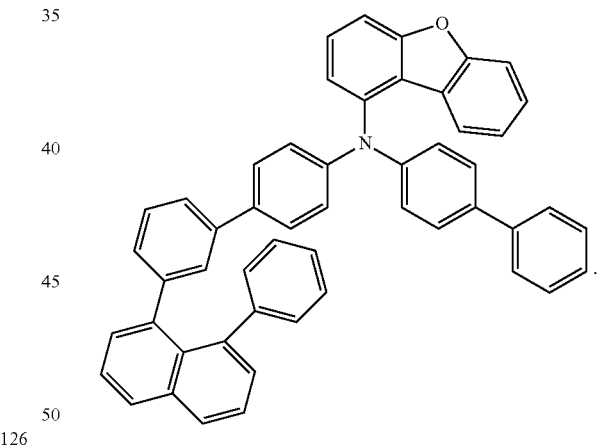
14. An amine compound represented by the following Formula 1:
[Formula 1]
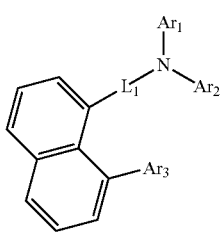

wherein in Formula 1, $Ar_1$ and $Ar_2$ are each independently a substituted or unsubstituted aryl group having 6 to 30 ring carbon atoms, or a substituted or unsubstituted heteroaryl group having 2 to 30 ring carbon atoms, and at least one of $Ar_1$ and $Ar_2$ is a substituted or unsubstituted heteroaryl group having 2 to 30 ring carbon atoms, $Ar_3$ is a substituted or unsubstituted aryl group having 6 to 20 ring carbon atoms, and $L_1$ is a substituted or unsubstituted arylene group having 6 to 30 ring carbon atoms, or a substituted or unsubstituted heteroarylene group having 2 to 30 ring carbon atoms.

\* \* \* \* \*